United States Patent
Ozsolak

(10) Patent No.: US 10,758,558 B2
(45) Date of Patent: Sep. 1, 2020

(54) HYBRID OLIGONUCLEOTIDES AND USES THEREOF

(71) Applicant: Translate Bio MA, Inc., Lexington, MA (US)

(72) Inventor: Fatih Ozsolak, Boston, MA (US)

(73) Assignee: Translate Bio MA, Inc., Lexington, MA (US)

( * ) Notice: Subject to any disclaimer, the term of this patent is extended or adjusted under 35 U.S.C. 154(b) by 0 days.

(21) Appl. No.: 15/550,108

(22) PCT Filed: Feb. 12, 2016

(86) PCT No.: PCT/US2016/017790
§ 371 (c)(1),
(2) Date: Aug. 10, 2017

(87) PCT Pub. No.: WO2016/130943
PCT Pub. Date: Aug. 18, 2016

(65) Prior Publication Data
US 2018/0028557 A1    Feb. 1, 2018

Related U.S. Application Data

(60) Provisional application No. 62/115,754, filed on Feb. 13, 2015.

(51) Int. Cl.
| | | |
|---|---|---|
| C07H 21/02 | (2006.01) | |
| C07H 21/04 | (2006.01) | |
| A61K 31/7105 | (2006.01) | |
| C12N 15/11 | (2006.01) | |
| C12N 15/113 | (2010.01) | |

(52) U.S. Cl.
CPC ........ *A61K 31/7105* (2013.01); *C12N 15/111* (2013.01); *C12N 15/113* (2013.01); *C12N 2310/141* (2013.01); *C12N 2310/152* (2013.01); *C12N 2310/34* (2013.01)

(58) Field of Classification Search
CPC . A61K 31/713; C12N 15/115; C12N 2310/11
See application file for complete search history.

(56) References Cited

U.S. PATENT DOCUMENTS

| | | |
|---|---|---|
| 4,725,677 A | 2/1988 | Köster et al. |
| 5,225,326 A | 7/1993 | Bresser et al. |
| 5,491,133 A | 2/1996 | Walder et al. |
| 5,576,208 A | 11/1996 | Monia et al. |
| 5,580,859 A | 12/1996 | Felgner et al. |
| 5,582,972 A | 12/1996 | Lima et al. |
| 5,623,065 A | 4/1997 | Cook et al. |
| 5,652,355 A | 7/1997 | Metelev et al. |
| 5,661,134 A | 8/1997 | Cook et al. |
| 5,728,527 A | 3/1998 | Singer et al. |
| 5,766,903 A | 6/1998 | Sarnow et al. |
| 5,773,244 A | 6/1998 | Ares et al. |
| 5,866,331 A | 2/1999 | Singer et al. |
| 5,914,396 A | 6/1999 | Cook et al. |
| 5,919,619 A | 7/1999 | Tullis |
| 5,962,332 A | 10/1999 | Singer et al. |
| 5,962,675 A | 10/1999 | Beigelman et al. |
| 5,965,722 A | 10/1999 | Ecker et al. |
| 6,015,710 A | 1/2000 | Shay et al. |
| 6,046,307 A | 4/2000 | Shay et al. |
| 6,107,094 A | 8/2000 | Crooke |
| 6,111,094 A | 8/2000 | Bennet et al. |
| 6,143,881 A | 11/2000 | Metelev et al. |
| 6,146,829 A | 11/2000 | Cook et al. |
| 6,197,944 B1 | 3/2001 | Walder et al. |
| 6,210,892 B1 | 4/2001 | Bennett et al. |
| 6,210,931 B1 | 4/2001 | Feldstein et al. |
| 6,261,836 B1 | 7/2001 | Cech et al. |
| 6,277,981 B1 | 8/2001 | Tu et al. |
| 6,284,458 B1 | 9/2001 | Anderson et al. |
| 6,287,825 B1 | 9/2001 | Weissman et al. |
| 6,291,637 B1 | 9/2001 | Das et al. |
| 6,294,650 B1 | 9/2001 | Shay et al. |
| 6,322,978 B1 | 11/2001 | Kahn et al. |
| 6,326,199 B1 | 12/2001 | Cook et al. |
| 6,346,614 B1 | 2/2002 | Metelev et al. |

(Continued)

FOREIGN PATENT DOCUMENTS

| | | |
|---|---|---|
| CA | 2805791 A1 | 1/2012 |
| EP | 1 044 987 A2 | 10/2000 |

(Continued)

OTHER PUBLICATIONS

Bandiera et al., Genetic variations creating microRNA target sites in the FXN 3'-UTR affect frataxin expression in Friedreich ataxia. PLoS One. 2013;8(1):e54791. doi: 10.1371/journal.pone.0054791. Epub Jan. 30, 2013.
Gooding et al., Oligonucleotide conjugates—Candidates for gene silencing therapeutics. European J Pharmaceutics Biopharmaceutics, 2016;107:321-340.
Lagier-Tourenne et al., Targeted degradation of sense and antisense C9orf72 RNA foci as therapy for ALS and frontotemporal degeneration. Proc Natl Acad Sci U S A. Nov. 19, 2013;110(47):E4530-9. doi: 10.1073/pnas.1318835110. Epub Oct. 29, 2013. Supporting Information.
Lebedeva et al., Phosphorothioate Oligodeoxynucleotides as Inhibitors of Gene Expression: Antisense and Non-Antisense Effects. Applications of Antisense Therapies to Restenosis. 1999;99-118.
Mignone et al., Untranslated regions of mRNAs. Genome Biol. 2002;3(3):REVIEWS0004. Epub Feb. 28, 2002.

(Continued)

*Primary Examiner* — Amy H Bowman
(74) *Attorney, Agent, or Firm* — Wolf, Greenfield & Sacks, P.C.

(57) ABSTRACT

Provided herein are hybrid oligonucleotides comprising a region that promotes cleavage of a nucleic acid and a region that protects a nucleic acid from exonuclease activity. Such hybrid oligonucleotides are useful for modulating the expression of genes. Related compositions and methods are also provided. In some embodiments, methods are provided for treating a disease, such as by administering a hybrid oligonucleotide.

20 Claims, 12 Drawing Sheets

Specification includes a Sequence Listing.

(56) References Cited

U.S. PATENT DOCUMENTS

| | | |
|---|---|---|
| 6,359,124 B1 | 3/2002 | Ecker et al. |
| 6,403,566 B1 | 6/2002 | Wang |
| 6,451,991 B1 | 9/2002 | Martin et al. |
| 6,503,756 B1 | 1/2003 | Freier et al. |
| 6,531,584 B1 | 3/2003 | Cook et al. |
| 6,582,908 B2 | 6/2003 | Fodor et al. |
| 6,602,857 B1 | 8/2003 | Cowsert et al. |
| 6,608,035 B1 | 8/2003 | Agrawal et al. |
| 6,677,445 B1 | 1/2004 | Innis et al. |
| 6,727,355 B2 | 4/2004 | Matsuo et al. |
| 6,753,423 B1 | 6/2004 | Cook et al. |
| 6,831,166 B2 | 12/2004 | Manoharan et al. |
| 6,838,283 B2 | 1/2005 | Bennett et al. |
| 6,858,726 B2 | 2/2005 | Koch et al. |
| 6,919,439 B2 | 7/2005 | Manoharan et al. |
| 7,015,315 B1 | 3/2006 | Cook et al. |
| 7,041,816 B2 | 5/2006 | Ravikumar et al. |
| 7,045,609 B2 | 5/2006 | Metelev et al. |
| 7,399,845 B2 | 7/2008 | Seth et al. |
| 7,687,617 B2 | 3/2010 | Thrue et al. |
| 7,718,625 B2 | 5/2010 | Eichler et al. |
| 7,790,675 B2 | 9/2010 | Scheiber-Mojdehkar et al. |
| 7,879,992 B2 | 2/2011 | Vickers et al. |
| 7,888,012 B2 | 2/2011 | Iversen et al. |
| 7,951,935 B2 * | 5/2011 | Khvorova ............... C07H 21/00 536/24.5 |
| 8,092,992 B2 | 1/2012 | Kuwabara et al. |
| 8,129,515 B2 | 3/2012 | Esau et al. |
| 8,153,602 B1 | 4/2012 | Bennett et al. |
| 8,288,356 B2 | 10/2012 | Obad et al. |
| 8,309,705 B2 | 11/2012 | Zamore et al. |
| 8,361,980 B2 | 1/2013 | Kauppinen et al. |
| 8,404,659 B2 | 3/2013 | Kauppinen et al. |
| 8,415,313 B2 | 4/2013 | Mourich et al. |
| 8,846,639 B2 | 9/2014 | Swayze et al. |
| 8,975,023 B2 | 3/2015 | Okumura et al. |
| 9,580,708 B2 | 2/2017 | Uhlmann et al. |
| 9,593,330 B2 * | 3/2017 | Collard ............... C12N 15/113 |
| 2001/0055758 A1 | 12/2001 | Billing-Medel et al. |
| 2002/0009724 A1 | 1/2002 | Schlegel et al. |
| 2002/0018996 A1 | 2/2002 | Kimura et al. |
| 2002/0160379 A1 | 10/2002 | Cook et al. |
| 2003/0083272 A1 | 5/2003 | Wiederholt et al. |
| 2003/0113914 A1 | 6/2003 | Graham |
| 2003/0125241 A1 | 7/2003 | Wissenbach et al. |
| 2003/0125273 A1 | 7/2003 | Bennett et al. |
| 2003/0125274 A1 | 7/2003 | Gaarde |
| 2003/0125276 A1 | 7/2003 | Bennett et al. |
| 2003/0211606 A1 | 11/2003 | Dobie |
| 2003/0228690 A1 | 12/2003 | Baker et al. |
| 2004/0005565 A1 | 1/2004 | Bennett et al. |
| 2004/0023378 A1 | 2/2004 | Chiang |
| 2004/0023906 A1 | 2/2004 | Dean et al. |
| 2004/0033977 A1 | 2/2004 | Bennett et al. |
| 2004/0038274 A1 | 2/2004 | Cook et al. |
| 2004/0096848 A1 | 5/2004 | Thrue et al. |
| 2004/0097441 A1 | 5/2004 | Dobie |
| 2004/0110153 A1 | 6/2004 | Dong et al. |
| 2004/0115674 A1 | 6/2004 | Knott et al. |
| 2004/0171047 A1 | 9/2004 | Dahl et al. |
| 2004/0209838 A1 | 10/2004 | Monia et al. |
| 2004/0248840 A1 | 12/2004 | Hansen et al. |
| 2005/0014168 A1 | 1/2005 | Erlander et al. |
| 2005/0026160 A1 | 2/2005 | Allerson et al. |
| 2005/0048529 A1 | 3/2005 | McSwiggen |
| 2005/0079614 A1 | 4/2005 | Reinhart et al. |
| 2005/0108783 A1 | 5/2005 | Koike |
| 2005/0112631 A1 | 5/2005 | Piepenburg et al. |
| 2005/0130924 A1 | 6/2005 | Monia et al. |
| 2005/0231216 A1 | 10/2005 | Gozzini |
| 2005/0261217 A1 | 11/2005 | Dobie et al. |
| 2005/0261218 A1 | 11/2005 | Esau et al. |
| 2005/0287539 A1 | 12/2005 | Labourier |
| 2006/0128646 A1 | 6/2006 | Christensen et al. |
| 2006/0205635 A1 | 9/2006 | Corey et al. |
| 2006/0211640 A1 | 9/2006 | Kane |
| 2006/0223098 A1 | 10/2006 | Lane et al. |
| 2006/0269530 A1 | 11/2006 | Clawson et al. |
| 2006/0270624 A1 | 11/2006 | Cook et al. |
| 2007/0032446 A1 | 2/2007 | Cook et al. |
| 2007/0066549 A1 | 3/2007 | Freier et al. |
| 2007/0111963 A1 | 5/2007 | Corey et al. |
| 2007/0123484 A1 | 5/2007 | Bhat et al. |
| 2007/0123485 A1 | 5/2007 | Honigman et al. |
| 2007/0219244 A1 | 9/2007 | Jenssen et al. |
| 2008/0015162 A1 | 1/2008 | Bhanot et al. |
| 2008/0299662 A1 | 12/2008 | Ferrandez |
| 2008/0300142 A1 | 12/2008 | Getts et al. |
| 2009/0082297 A1 | 3/2009 | Lioy et al. |
| 2009/0092988 A1 | 4/2009 | Schwartz et al. |
| 2009/0143326 A1 | 6/2009 | Obad et al. |
| 2009/0155910 A1 | 6/2009 | McGonigle |
| 2009/0156538 A1 | 6/2009 | Dobie |
| 2009/0181916 A1 | 7/2009 | Worm |
| 2009/0203046 A1 | 8/2009 | Ono et al. |
| 2009/0203765 A1 | 8/2009 | Bhanot et al. |
| 2009/0221685 A1 | 9/2009 | Esau et al. |
| 2010/0056768 A1 | 3/2010 | Wengel |
| 2010/0184833 A1 | 7/2010 | De Kimpe et al. |
| 2010/0197762 A1 | 8/2010 | Swayze et al. |
| 2010/0210712 A1 | 8/2010 | Hansen et al. |
| 2010/0249214 A1 | 9/2010 | Brown |
| 2010/0256223 A1 | 10/2010 | Moeller et al. |
| 2010/0285476 A1 | 11/2010 | Rusche et al. |
| 2011/0054012 A1 | 3/2011 | Place et al. |
| 2011/0077286 A1 | 3/2011 | Damha et al. |
| 2011/0172292 A1 * | 7/2011 | Hansen ............... C12N 15/111 514/44 A |
| 2011/0184050 A1 | 7/2011 | De Kimpe et al. |
| 2011/0190222 A1 | 8/2011 | Corey et al. |
| 2011/0190370 A1 | 8/2011 | Ward et al. |
| 2011/0245327 A1 | 10/2011 | Wengel et al. |
| 2011/0251261 A1 | 10/2011 | Burnett et al. |
| 2011/0263687 A1 | 10/2011 | Mattick et al. |
| 2011/0269818 A1 | 11/2011 | Bennett et al. |
| 2011/0287415 A1 | 11/2011 | Fan et al. |
| 2011/0306653 A1 | 12/2011 | Hirao et al. |
| 2012/0052487 A9 | 3/2012 | Khvorova et al. |
| 2012/0065252 A1 | 3/2012 | Schrum et al. |
| 2012/0071418 A1 | 3/2012 | Copeland et al. |
| 2012/0083596 A1 | 4/2012 | Elmen et al. |
| 2012/0157333 A1 | 6/2012 | Kauppinen et al. |
| 2012/0263738 A1 * | 10/2012 | Brown ............... A61K 31/713 424/178.1 |
| 2012/0288869 A1 | 11/2012 | Schwartz et al. |
| 2012/0295952 A1 | 11/2012 | Collard et al. |
| 2012/0322851 A1 | 12/2012 | Hardee et al. |
| 2013/0079505 A1 | 3/2013 | Moeller et al. |
| 2013/0096183 A1 | 4/2013 | Collard et al. |
| 2013/0164846 A1 | 6/2013 | Saestrom |
| 2013/0177909 A1 | 7/2013 | Okumura et al. |
| 2013/0184325 A9 | 7/2013 | Collard et al. |
| 2013/0210918 A1 | 8/2013 | Gottesfeld et al. |
| 2013/0225659 A1 | 8/2013 | Bennett |
| 2013/0244282 A1 | 9/2013 | Schrum et al. |
| 2013/0245099 A1 | 9/2013 | Collard et al. |
| 2013/0280713 A1 | 10/2013 | Park et al. |
| 2014/0128455 A1 | 5/2014 | Zain-Luqman et al. |
| 2014/0187606 A1 | 7/2014 | Collard et al. |
| 2014/0316126 A1 | 10/2014 | Saetrom |
| 2014/0329700 A1 | 11/2014 | Tian et al. |
| 2015/0050738 A1 | 2/2015 | Ozsolak et al. |
| 2015/0152410 A1 | 6/2015 | Krieg et al. |
| 2015/0159160 A1 | 6/2015 | Krieg et al. |
| 2015/0159161 A1 | 6/2015 | Krieg et al. |
| 2015/0191722 A1 | 7/2015 | Krieg et al. |
| 2015/0218560 A1 | 8/2015 | Krieg et al. |
| 2015/0225715 A1 | 8/2015 | Ozsolak |
| 2015/0232844 A1 | 8/2015 | Ozsolak |
| 2015/0232845 A1 | 8/2015 | Ozsolak |
| 2015/0232846 A1 | 8/2015 | Ozsolak |
| 2015/0232847 A1 | 8/2015 | Ozsolak |
| 2015/0247141 A1 | 9/2015 | Uhlmann et al. |
| 2015/0247144 A1 | 9/2015 | Ozsolak |

(56) References Cited

U.S. PATENT DOCUMENTS

| | | |
|---|---|---|
| 2015/0247145 A1 | 9/2015 | Ozsolak |
| 2016/0032273 A1 | 2/2016 | Shahrokh et al. |
| 2018/0055869 A1 | 3/2018 | Ozsolak et al. |

FOREIGN PATENT DOCUMENTS

| | | | |
|---|---|---|---|
| EP | 1 695 979 A2 | 8/2006 | |
| EP | 2246422 | 11/2010 | |
| JP | 4236812 B2 | 3/2009 | |
| JP | 2010-507579 A | 3/2010 | |
| WO | WO 1989/005358 A1 | 6/1989 | |
| WO | WO 1992/001813 A1 | 2/1992 | |
| WO | WO 1993/013121 A1 | 7/1993 | |
| WO | WO 1994/001550 A1 | 1/1994 | |
| WO | WO 1994/002499 A1 | 2/1994 | |
| WO | WO 1994/017093 A1 | 8/1994 | |
| WO | WO 1997/038013 A1 | 10/1997 | |
| WO | WO 1999/010509 A1 | 3/1999 | |
| WO | WO 2000/020645 A1 | 4/2000 | |
| WO | WO 2001/000821 A1 | 1/2001 | |
| WO | WO 2002/022635 A1 | 3/2002 | |
| WO | WO 2005/042018 A2 | 5/2005 | |
| WO | WO 2005/116250 A2 | 12/2005 | |
| WO | WO 2006/108423 A2 | 10/2006 | |
| WO | WO 2007/133812 A2 | 11/2007 | |
| WO | WO 2008/018795 A1 | 2/2008 | |
| WO | WO 2008/029619 A1 | 3/2008 | |
| WO | WO 2008/113832 A2 | 9/2008 | |
| WO | WO 2008/151639 A2 | 12/2008 | |
| WO | WO 2009/032083 A1 | 3/2009 | |
| WO | WO 2009/043353 A2 | 4/2009 | |
| WO | WO 2009/055675 A1 | 4/2009 | |
| WO | WO 2009/090182 A1 | 7/2009 | |
| WO | WO 2009/093384 A1 | 7/2009 | |
| WO | WO 2009/099326 A1 | 8/2009 | |
| WO | WO 2009/124341 A1 | 10/2009 | |
| WO | WO 2010/000665 A1 | 1/2010 | |
| WO | WO 2010/040112 A2 | 4/2010 | |
| WO | WO 2010/093860 A2 | 8/2010 | |
| WO | WO 2010/115993 A1 | 10/2010 | |
| WO | WO 2010/120803 A2 | 10/2010 | |
| WO | WO 2010/120820 A1 | 10/2010 | |
| WO | WO 2010/120969 A1 * | 10/2010 | ........... C12N 15/115 |
| WO | WO 2011/048125 A1 | 4/2011 | |
| WO | WO 2011/053994 A1 | 5/2011 | |
| WO | WO 2011/057350 A1 | 5/2011 | |
| WO | WO 2011/117353 A1 * | 9/2011 | ........... C12N 15/115 |
| WO | WO 2011/139917 A1 | 11/2011 | |
| WO | WO 2011/159836 A2 | 12/2011 | |
| WO | WO 2011/161460 A2 | 12/2011 | |
| WO | WO 2012/024478 A2 | 2/2012 | |
| WO | WO 2012/028961 A2 | 3/2012 | |
| WO | WO 2012/044171 A1 | 4/2012 | |
| WO | WO 2012/050975 A2 | 4/2012 | |
| WO | WO 2012/109476 A2 | 8/2012 | |
| WO | WO 2012/122645 A1 | 9/2012 | |
| WO | WO 2012/138289 A1 | 10/2012 | |
| WO | WO 2012/149478 A2 | 11/2012 | |
| WO | WO 2012/158736 A1 | 11/2012 | |
| WO | WO 2012/162514 A2 | 11/2012 | |
| WO | WO 2012/170771 A1 | 12/2012 | |
| WO | WO 2013/033223 A1 | 3/2013 | |
| WO | WO 2013/039857 A1 | 3/2013 | |
| WO | WO 2013/039861 A2 | 3/2013 | |
| WO | WO 2013/090186 A1 | 6/2013 | |
| WO | WO 2013/101690 A1 | 7/2013 | |
| WO | WO 2013/106496 A1 | 7/2013 | |
| WO | WO 2013/120003 A1 | 8/2013 | |
| WO | WO 2013/130161 A1 | 9/2013 | |
| WO | WO 2013/173599 A1 | 11/2013 | |
| WO | WO 2013/173605 A1 | 11/2013 | |
| WO | WO 2013/173608 A1 | 11/2013 | |
| WO | WO 2013/185067 A1 | 12/2013 | |
| WO | WO 2014/043544 A1 | 3/2014 | |
| WO | WO 2014/076195 A1 | 5/2014 | |
| WO | WO 2014/144942 A2 | 9/2014 | |
| WO | WO 2014/145138 A2 | 9/2014 | |
| WO | WO 2015/020993 A2 | 2/2015 | |
| WO | WO 2015/023939 A1 | 2/2015 | |
| WO | WO 2015/023975 A1 | 2/2015 | |
| WO | WO 2015/034925 A1 | 3/2015 | |
| WO | WO 2016/077837 A1 | 5/2016 | |

OTHER PUBLICATIONS

[No Author Listed] Designing Antisense Oligonucleotides. Integrated DNA Technologies. 2011. 1-16.

[No Author Listed], Anchored Oligo(dT)20 Primer. Invitrogen Life Technologies. Rev. date: Jun. 19 2003. 1 page.

Bidichandani et al., Somatic sequence variation at the Friedreich ataxia locus includes complete contraction of the expanded GAA triplet repeat, significant length variation in erially passaged lymphoblasts and enhanced mutagenesis in the flanking sequence. Hum Mol Genet. Dec. 1999;8(13):2425-36.

Buck et al., Design strategies and performance of custom DNA sequencing primers. Biotechniques. Sep. 1999;27(3):528-36.

Carr et al., Isolation and characterization of the rat thyrotropin beta-subunit gene. Differential regulation of two transcriptional start sites by thyroid hormone. J Biol Chem. Jan. 25, 1987;262(3):981-7.

Carthew et al., Origins and Mechanisms of miRNAs and siRNAs. Cell. Feb. 20, 2009;136(4):642-55. doi: 10.1016/j.cell.2009.01.035. Review.

Chan et al., Heterochromatinization induced by GAA-repeat hyperexpansion in Friedreich's ataxia can be reduced upon HDAC inhibition by vitamin B3. Hum Mol Genet. 2013;22(13):2662-75.

Crooke et al., Kinetic characteristics of *Escherichia coli* RNase H1: cleavage of various antisense oligonucleotide-RNA duplexes. Biochem J. Dec. 1, 1995;312 ( Pt 2):599-608.

Crooke, Antisense drug technology. Principles, strategies, and applications. $2^{nd}$ edition. CRC Press. 2007. 120-123.

Dahl et al., Circle-to-circle amplification for precise and sensitive DNA analysis. Proc Natl Acad Sci U S A. Mar. 30, 2004;101(13):4548-53.

Daughters et al., RNA gain-of-function in spinocerebellar ataxia type 8. PLoS Genet. Aug. 2009;5(8):e1000600. doi: 10.1371/journal.pgen.1000600. Epub Aug. 14, 2009.

Davidson et al., Singles engage the RNA interference pathway. Cell. Aug. 31, 2012;150(5):873-5. doi: 10.1016/j.cell.2012.08.008.

Dinger et al., NRED: a database of long noncoding RNA expression. Nucleic Acids Res. Jan. 2009;37(Database issue):D122-6. doi: 10.1093/nar/gkn617. Epub Oct. 1, 2008.

Ditch et al., Progressive GAA.TTC repeat expansion in human cell lines. PLoS Genet. Oct. 2009;5(10):e1000704. doi: 10.1371/journal.pgen.1000704.

Dominski et al., Identification and characterization by antisense oligonucleotides of exon and intron sequences required for splicing. Mol Cell Biol. Nov. 1994; 14(11): 7445-7454.

Eddy, Non-coding RNA genes and the modern RNA world. Nat Rev Genet. Dec. 2001;2(12):919-29.

Fratczak et al., LNA-modified primers drastically improve hybridization to target RNA and reverse transcription. Biochemistry. Jan. 27, 2009;48(3):514-6. doi: 10.1021/bi8021069.

Frieden et al., Expanding the design horizon of antisense oligonucleotides with alpha-L-LNA. Nucleic Acids Res. Nov. 1, 2003;31(21):6365-72.

Frith et al., A code for transcription initiation in mammalian genomes. Genome Res. Jan. 2008;18(1):1-12.

Genbank Submission; NCBI, Accession No. BX572607.1; 2015.

Genbank Submission; NCBI, Accession No. LA219700. Peng et al., Jun. 7, 2014.

Genbank Submission; NCBI, Accession No. NM_000144.4. Pandey et al., Mar. 15, 2015. 6 pages.

Genbank Submission; NCBI, Accession No. NM_000314.5. Singh et al., Mar. 15, 2015. 9 pages.

Genbank Submission; NCBI, Accession No. NM_002155.4. Khalouei et al., Dec. 11, 2014. 3 pages.

Genbank Submission; NCBI, Accession No. NM_002605.2. Oct. 16, 2017.

(56) References Cited

OTHER PUBLICATIONS

Genbank Submission; NCBI, Accession No. NM_181897.2. Oct. 16, 2017.
Genbank Submission; NCBI, Accession No. U93173.1; Laccone et al., Jan. 5, 1999.
Genbank Submission; NCBI, Accession No. XM_004398354.1. Mar. 31, 2013. 2 pages.
Genbank Submission; NCBI, Accession No. XM_006715245.3; Jun. 6, 2016.
Genbank submission; NCBI; Accession No. NM_01099771.2.; Sep. 1, 2016. Pieragostino et al.
Genbank submission; NCBI; Accession No. NM_013402.4; Oct. 6, 2016. Barman et al.
Genbank submission; NCBI; Accession No. XR_001732682.1; Jun. 6, 2016.
Geneseq Submission; EBI Accession No. AJJ96000. Dec. 28, 2007.
Geneseq Submission; EBI Accession No. AJL53182. Dec. 28, 2007.
Geneseq Submission; EBI Accession No. AXQ92558. Nov. 26, 2009.
Geneseq Submission; EBI Accession No. AYB40768. Jul. 22, 2010.
Gogliotti et al., The DcpS inhibitor RG3039 improves survival, function and motor unit pathologies in two SMA mouse models. Hum Mol Genet. Jun. 4, 2013.
Greiner et al., Identification of a specific inhibitor of the histone methyltransferase SU(VAR)3-9. Nature Chem Biol. Aug. 2005;1(3):143-5.
Hernandez et al., Degradation of nuclease-stabilized RNA oligonucleotides in Mycoplasma-contaminated cell culture media. Nucleic Acid Ther. Feb. 2012;22(1):58-68. doi: 10.1089/nat.2011.0316. Epub Jan. 9, 2012.
Jan et al., Formation, regulation and evolution of Caenorhabditis elegans 3'UTRs. Nature. Jan. 6, 2011;469(7328):97-101. doi:10.1038/nature09616. Epub Nov. 17, 2010.
Janowski et al., Inhibiting gene expression at transcription start sites in chromosomal DNA with antigene RNAs. Nat Chem Biol. Sep. 2005;1(4):216-22. Epub Jul. 31, 2005.
Jepsen et al., Locked nucleic acid: a potent nucleic acid analog in therapeutics and biotechnology. Oligonucleotides. 2004;14(2):130-46. Review.
Johansson et al., Target-specific arrest of mRNA translation by antisense 2'-O-alkyloligoribonucleotides. Nucleic Acids Res. Nov. 11, 1994;22(22):4591-8.
Kierzek et al., The influence of locked nucleic acid residues on the thermodynamic properties of 2'-O-methyl RNA/RNA heteroduplexes. Nucleic Acids Res. Sep. 9, 2005;33(16):5082-93. Print 2005.
Kim, MicroRNA biogenesis: coordinated cropping and dicing. Nat Rev Mol Cell Biol. May 2005;6(5):376-85.
Krützfeldt et al., Silencing of microRNAs in vivo with 'antagomirs'. Nature. Dec. 1, 2005;438(7068):685-9. Epub Oct. 30, 2005.
Kukis et al., Cleavable linkers to enhance selectivity of antibody-targeted therapy of cancer. Cancer Biother Radiopharm. Dec. 2001;16(6):457-67. Review.
Kumari et al., Chromatin remodeling in the noncoding repeat expansion diseases. J Biol Chem. Mar. 20, 2009;284(12):7413-7. doi: 10.1074/jbc.R800026200.
Kurreck et al. Design of antisense oligonucleotides stabilized by locked nucleic acids. Nucleic Acids Res. May 1, 2002; 30(9): 1911-1918.
Larimer et al., Complete genome sequence of the metabolically versatile photosynthetic bacterium Rhodopseudomonas palustris. Nat Biotechnol. Jan. 2004;22(1):55-61. Epub Dec. 14, 2003.
Latorra et al., Design considerations and effects of LNA in PCR primers. Mol Cell Probes. Oct. 2003;17(5):253-9.
Lennox et al., Improved Performance of Anti-miRNA Oligonucleotides Using a Novel Non-Nucleotide Modifier. Mol Ther Nucleic Acids. Aug. 27, 2013;2:e117. doi: 10.1038/mtna.2013.46.
Li et al., Excision of Expanded GAA Repeats Alleviates the Molecular Phenotype of Friedreich's Ataxia. Mol Ther. Jun. 2015;23(6):1055-65. doi:10.1038/mt.2015.41. Epub Mar. 11, 2015.
Li et al., Expression of human frataxin is regulated by transcription factors SRF and TFAP2. PLoS One. Aug. 20, 2010;5(8):e12286. doi: 10.1371/journal.pone.0012286. 8 pages.
Lima et al., Single-stranded siRNAs activate RNAi in animals. Cell. Aug. 31, 2012;150(5):883-94. doi: 10.1016/j.cell.2012.08.014.
Majlessi et al., Advantages of 2'-O-methyl oligoribonucleotide probes for detecting RNA targets. Nucleic Acids Res. May 1, 1998;26(9):2224-9.
Merienne et al., SCA8 CAG/CTG expansions, a tale of two TOXICities: a unique or common case? PLoS Genet. Aug. 2009;5(8):e1000593. doi: 10.1371/journal.pgen.1000593. Epub Aug. 14, 2009.
Minet et al., HIF1A gene transcription is dependent on a core promoter sequence encompassing activating and inhibiting sequences located upstream from the transcription initiation site and cis elements located within the 5'UTR. Biochem Biophys Res Commun. Aug. 2, 1999;261(2):534-40.
Nam et al., Oligo(dT) primer generates a high frequency of truncated cDNAs through internal poly(A) priming during reverse transcription. Proc Natl Acad Sci U S A. Apr. 30, 2002;99(9):6152-6. Epub Apr. 23, 2002.
Nishida et al., Synthesis, RNA selective hybridization and high nuclease resistance of an oligonucleotide containing novel bridged nucleic acid with cyclic urea structure. Chem Commun (Camb). Aug. 7, 2010;46(29):5283-5. doi: 10.1039/c0cc00154f. Epub Jun. 22, 2010.
Ørom et al., LNA-modified oligonucleotides mediate specific inhibition of microRNA function. Gene. May 10, 2006;372:137-41. Epub Feb. 24, 2006.
Paro et al., Extending the frontiers of epigenetic regulation. Curr Opin Genet Dev. Apr. 2010;20(2):107-9. doi: 10.1016/j.gde.2010.03.011.
Petersen et al., LNA: a versatile tool for therapeutics and genomics. TRENDS Biotech. Feb. 2003;21(2):74-81. Review.
Ruan et al., Genome wide full-length transcript analysis using 5' and 3' paired-end-tag next generation sequencing (RNA-PET). Methods Mol Biol. 2012;809:535-62. doi: 10.1007/978-1-61779-376-9_35.
Sankaran, Targeted therapeutic strategies for fetal hemoglobin induction. Hematol Am Soc Hematol Educ Program. 2011;2011:459-65.
Scaringe, Advanced 5'-Silyl-2'-Orthoester Approach to RNA Oligonucleotide Synthesis. Meth Enzym. 2000;317:3-18.
Sciabola et al., Improved nucleic acid descriptors for siRNA efficacy prediction. Nucleic Acids Res. Feb. 1, 2013;41(3):1383-94. doi: 10.1093/nar/gks1191.
Shepard et al., Complex and dynamic landscape of RNA polyadenylation revealed by PAS-Seq. RNA. Apr. 2011;17(4):761-72. doi: 10.1261/rna.2581711. Epub Feb. 22, 2011.
Silahtaroglu et al., FISHing with locked nucleic acids (LNA): evaluation of different LNA/DNA mixmers. Mol Cell Probes. Aug. 2003;17(4):165-9.
Sonenberg et al., Eukaryotic translation initiation factors and regulators. Curr Opin Struct Biol. Feb. 2003;13(1):56-63.
Taylor et al., Antisense oligonucleotides: a systematic high-throughput approach to target validation and gene function determination. Drug Discov Today. Dec. 1999;4(12):562-567.
Vedernikov et al., Hepatitis C virus genotyping using 5' nuclease real-time PCR and probes with oligodeoxyinosine linkers. Mol Gen Micro Virol. Dec. 2009;24(2):200-206.
Vickers et al., Fully modified 2' MOE oligonucleotides redirect polyadenylation. Nucleic Acids Res. Mar. 15, 2001;29(6):1293-9.
Wells, DNA triplexes and Friedreich ataxia. FASEB J. Jun. 2008;22(6):1625-34. doi: 10.1096/fj.07-097857.
Xu et al., Improved Histone Deacetylase Inhibitors as Therapeutics for the Neurodegenerative Disease Friedreich's Ataxia: A New Synthetic Route. Pharmaceuticals (Basel). Dec. 14, 2011;4(12):1578-1590.
Yandim et al., Gene regulation and epigenetics in Friedreich's ataxia. J Neurochem. Aug. 2013;126 Suppl 1:21-42. doi: 10.1111/jnc.12254. Review.
Yoshizawa et al., Nuclease resistance of an extraordinarily thermostable mini-hairpin DNA fragment, d(GCGAAGC) and its application to in vitro protein synthesis. Nucleic Acids Res. Jun. 25, 1994;22(12):2217-21.

(56) References Cited

OTHER PUBLICATIONS

Yu et al., Single-stranded RNAs use RNAi to potently and allele-selectively inhibit mutant huntingtin expression. Cell. Aug. 31, 2012;150(5):895-908. doi: 10.1016/j.cell.2012.08.002.
Zhao et al., Systematic clustering of transcription start site landscapes. PLoS One. 2011;6(8):e23409. doi:10.1371/journal.pone.0023409. Epub Aug. 24, 2011.
Park et al., Effects of different target sites on antisense RNA-mediated regulation of gene expression. BMB Rep. Nov. 2014;47(11):619-24.
Extended European Search Report and Written Opinion for Application No. EP 14835805.4, dated Mar. 22, 2017.
International Search Report and Written Opinion for Application No. PCT/US2014/051331, dated Dec. 5, 2014.
International Preliminary Report on Patentability for Application No. PCT/US2014/051331, dated Feb. 25, 2016.
Extended European Search Report for Application No. EP 16749994.6, dated Aug. 13, 2018.
International Search Report and Written Opinion for Application No. PCT/US2016/017826, dated Jun. 30, 2016.
International Preliminary Report on Patentability for Application No. PCT/US2016/017826, dated Aug. 24, 2017.
[No Author Listed] piRNAdb Accession No. hsa-piR-20450. Retrieved from https://www.pirnadb.org/information/pirna/hsa-piR-20450 on Sep. 17, 2019. 2 pages.
[No Author Listed]The Human Proteome in Liver. The Human Protein Atlas. 2019. Retrieved from https://www.proteinatlast.org/humanproteome/tissue/liver on Sep. 4, 2019. 5 pages.
Alahari et al., Inhibition of expression of the multidrug resistance-associated P-glycoprotein of by phosphorothioate and 5' cholesterol-conjugated phosphorothioate antisense oligonucleotides. Mol Pharmacol. Oct. 1996;50(4):808-19.
Arzumanov et al., Inhibition of HIV-1 Tat-dependent trans activation by steric block chimeric 2'-O-methyl/LNA oligoribonucleotides. Biochemistry. Dec. 4, 2001;40(48):14645-54.
Baker et al., 2'-O-(2-Methoxy)ethyl-modified anti-intercellular adhesion molecule 1 (ICAM-1) oligonucleotides selectively increase the ICAM-1 mRNA level and inhibit formation of the ICAM-1 translation initiation complex in human umbilical vein endothelial cells. J. Biol. Chem. 272(18): 11994-12000.
Chahrour et al., MeCP2, a key contributor to neurological disease, activates and represses transcription. Science. May 30, 2008;320(5880):1224-9.
Cheng et al., Prediction of mRNA polyadenylation sites by support vector machine. Bioinformatics. Oct. 1, 2006;22(19):2320-5.
Cook et al., The use of antisense oligonucleotides to establish autocrine angiotensin growth effects in human neuroblastoma and mesangial cells. Antisense Res Dev. 1992 Fall;2(3):199-210.
Cumming et al., Error bars in experimental biology. J Cell Biol. Apr. 9, 2007;177(1):7-11.
Da Sacco et al., Recent insights and novel bioinformatics tools to understand the role of microRNAs binding to 5' untranslated region. Int J Mol Sci. Dec. 27, 2013;14(1):480-95. doi: 10.3390/ijms14010480.
Dean et al., Inhibition of protein kinase C-alpha expression in human A549 cells by antisense oligonucleotides inhibits induction of intercellular adhesion molecule 1 (ICAM-1) mRNA by phorbol esters. J Biol Chem. Jun. 10, 1994;269(23):16416-24.
Delgado et al., β-Catenin knockdown in liver tumor cells by a cell permeable gamma guanidine-based peptide nucleic acid. Curr Cancer Drug Targets. Oct. 2013;13(8):867-78.
Doyle et al., Inhibition of gene expression inside cells by peptide nucleic acids: effect of mRNA target sequence, mismatched bases, and PNA length. Biochemistry. Jan. 9, 2001;40(1):53-64.
Dragulescu-Andrasi et al., Cell-permeable peptide nucleic acid designed to bind to the 5'-untranslated region of E-cadherin transcript induces potent and sequence-specific antisense effects. J Am Chem Soc. Dec. 20, 2006;128(50):16104-12.
Du et al., Progress toward therapy with antisense-mediated splicing modulation. Curr Opin Mol Ther. Apr. 2009;11(2):116-23.

Fu et al., Mir-144 selectively regulates embryonic alpha-hemoglobin synthesis during primitive erythropoiesis. Blood. Feb. 5, 2009;113(6):1340-9.
Genbank Submission; NCBI, Accession No. AF024710.1 May 20, 2016.
Genbank Submission; NCBI, Accession No. AF095785.1 May 29, 2002.
Genbank Submission; NCBI, Accession No. AF106693. Ristow et al., Jul. 26, 2016.
Genbank Submission; NCBI, Accession No. AF301009.1. Dec. 5, 2000. Lin et al.
Genbank Submission; NCBI, Accession No. J03132.1 Nov. 8, 1994.
Genbank Submission; NCBI, Accession No. NG_009361.1; Salomons et al.; Jun. 20, 2016.
Genbank Submission; NCBI, Accession No. NM_000546.2. Dec. 24, 2006.
Genbank Submission; NCBI, Accession No. NM_021020.1 Sep. 28, 2008.
Genbank Submission; NCBI, Accession No. XM_003826157.2.; Sep. 2, 2014.
Genbank Submission; NCBI, Accession No. XM_016129106.1. Mar. 29, 2016.
Genbank Submission; NCBI, Accession No. XR_001909848.1. Aug. 31, 2016.
Genbank Submission; NCBI, Accession No. NM_007294.3; Orban et al.; May 25, 2016.
Genbank Submission; NCBI, Accession No. NM_199461.3; Miles et al.; Jun. 4, 2016.
Genbank submission; NCBI; Accession No. XM_017012145.1; Jun. 6, 2016.
Genbank Submission; NCBI; Accession No. XR_001759365.1.; Jun. 6, 2016.
Genbank Submission; NCBI, Accession No. NM_000144.4. Pandey et al., Mar. 15, 2015.
Genbank Submission; NCBI, Accession No. NM_000314.5. Singh et al., Mar. 15, 2015.
Genbank Submission; NCBI, Accession No. NM_001161706. Pandey et al., Mar. 15, 2015.
Genbank Submission; NCBI, Accession No. NM_002155.4. Khalouei et al., Dec. 11, 2014.
Genbank Submission; NCBI, Accession No. NM_181425.2. Pandey et al., Mar. 15, 2015.
Genbank Submission; NCBI, Accession No. XM_004398354.1. Mar. 31, 2013.
Ghisolfi et al., Increased Bcl2 expression by antisense oligoribonucleotides targeting the adenine-uridine-rich element motif. Mol Pharmacol. Sep. 2005;68(3):816-21. Epub Jun. 13, 2005.
Goodwin et al., the use of RNase H and poly(A) junction oligonucleotides in the analysis of in vitro polyadenylation reaction products. Nucleic Acids Res. Feb. 25, 1992;20(4):916.
Greenberg et al., Liver-specific expression of the human factor VII gene. Proc Natl Acad Sci U S A. Dec. 19, 1995;92(26):12347-51.
Grünweller et al., Locked nucleic acid oligonucleotides: the next generation of antisense agents? BioDrugs. 2007;21(4):235-43.
Harigai et al., A cis-acting element in the BCL-2 gene controls expression through translational mechanisms. Oncogene. Mar. 21, 1996;12(6):1369-74.
Hendrickson et al., Concordant regulation of translation and mRNA abundance for hundreds of targets of a human microRNA. PLoS Biol. Nov. 2009;7(11):e1000238. doi: 10.1371/journal.pbio.1000238. Epub Nov. 10, 2009.
Houseley et al., RNA-quality control by the exosome. Nat Rev Mol Cell Biol. Jul. 2006;7(7):529-39.
Khalil et al., Many human large intergenic noncoding RNAs associate with chromatin-modifying complexes and affect gene expression. Proc Natl Acad Sci U S A. Jul. 14, 2009;106(28):11667-72.
Ledebur et al., Transcriptional regulation of the intercellular adhesion molecule-1 gene by inflammatory cytokines in human endothelial cells. Essential roles of a variant NF-kappa B site and p65 homodimers. J Biol Chem. Jan. 13, 1995;270(2):933-43.
Lee et al., Global mapping of translation initiation sites in mammalian cells at single-nucleotide resolution. Proc Natl Acad Sci U

(56) References Cited

OTHER PUBLICATIONS

S A. Sep. 11, 2012;109(37):E2424-32. doi: 10.1073/pnas. 1207846109. Epub Aug. 27, 2012.

Lee, Epigenetic regulation by long noncoding RNAs. Science. Dec. 14, 2012;338(6113):1435-9. Review.

Liang et al., B1-induced caspase-independent apoptosis in MCF-7 cells is mediated by down-regulation of Bcl-2 via p53 binding to P2 promoter TATA box. Toxicol Appl Pharmacol. Oct. 1, 2011;256(1):52-61. doi:10.1016/j.taap.2011.07.010. Epub Jul. 23, 2011.

Lim et al., Modulation of survival motor neuron pre-mRNA splicing by inhibition of alternative 3' splice site pairing. J Biol Chem. Nov. 30, 2001;276(48):45476-83. Epub Oct. 2, 2001.

Loh et al., A trans-acting riboswitch controls expression of the virulence regulator PrfA in Listeria monocytogenes. Cell. Nov. 13, 2009;139(4):770-9. doi: 10.1016/j.cell.2009.08.046.

Matsui et al., Promoter RNA links transcriptional regulation of inflammatory pathway genes. Nucleic Acids Res. Dec. 2013; 41(22): 10086-10109.

Miller et al., A TALE nuclease architecture for efficient genome editing. Nat Biotechnol. Feb. 2011;29(2):143-8. doi:10.1038/nbt. 1755. Epub Dec. 22, 2010.

Miraglia et al., Inhibition of interleukin-1 type I receptor expression in human cell-lines by an antisense phosphorothioate oligodeoxynucleotide. Int J Immunopharmacol. Apr. 1996;18(4):227-40.

Monia et al., Antitumor activity of a phosphorothioate antisense oligodeoxynucleotide targeted against C-raf kinase. Nat Med. Jun. 1996;2(6):668-75. Erratum in: Nat Med. Feb. 1999;5(2):127.

Mouritzen et al., Single nucleotide polymorphism genotyping using locked nucleic acid (LNA). Expert Rev Mol Diagn. Jan. 2003;3(1):27-38.

Munroe, Antisense RNA inhibits splicing of pre-mRNA in vitro. EMBO J. Aug. 1998;7(8): 2523-2532.

Ozsolak et al., Comprehensive polyadenylation site maps in yeast and human reveal pervasive alternative polyadenylation. Cell. Dec. 10, 2010;143(6):1018-29. doi: 10.1016/j.cell.2010.11.020.

Paige et al., A temporal chromatin signature in human embryonic stem cells identifies regulators of cardiac development. Cell. Sep. 28, 2012;151(1):221-32. doi:10.1016/j.cell.2012.08.027. Epub Sep. 28, 2013. 20 pages.

Papucci et al., Impact of targeting the adenine- and uracil-rich element of bcl-2 mRNA with oligoribonucleotides on apoptosis, cell cycle, and neuronal differentiation in SHSY-5Y cells. Mol Pharmacol. Feb. 2008;73(2):498-508. Epub Nov. 7, 2007.

Raj et al., Imaging individual mRNA molecules using multiple singly labeled probes. Nat Methods. Oct. 2008;5(10):877-9. doi: 10.1038/nmeth.1253. Epub Sep. 21, 2008.

Rigo et al., Antisense-based therapy for the treatment of spinal muscular atrophy. J Cell Biol. Oct. 1, 2012;199(1):21-5. doi: 10.1083/jcb.201207087.

Rouleau et al., Small antisense oligonucleotides against G-quadruplexes: specific mRNA translational switches. Nucleic Acids Res. Jan. 2015;43(1):595-606. doi: 10.1093/nar/gku1311. Epub Dec. 15, 2014.

Sankaran et al., MicroRNA-15a and -16-1 act via MYB to elevate fetal hemoglobin expression in human trisomy 13. Proc Natl Acad Sci U S A. Jan. 25, 2011;108(4):1519-24.

Simon et al., Recognition of 2'-O-methylated 3'-end of piRNA by the PAZ domain of a Piwi protein. Structure. Feb. 9, 2011;19(2):172-80. doi: 10.1016/j.str.2010.11.015. Epub Jan. 20, 2011.

Skerra, Phosphorothioate primers improve the amplification of DNA sequences by DNA polymerases with proofreading activity. Nucleic Acids Res. Jul. 25, 1992;20(14):3551-4.

Suzuki et al., Diverse transcriptional initiation revealed by fine, large-scale mapping of mRNA start sites. EMBO Rep. May 2001;2(5):388-93.

Swarup et al., Identification and quantification of differentially expressed proteins in plasma of spinocerebellar ataxia type 12. Neurosci Res. Jun. 2012;73(2):161-7. doi: 10.1016/j.neures.2012. 03.002. Epub Mar. 16, 2012.

Taft et al., Tiny RNAs associated with transcription start sites in animals. Nat Genet. May 2009;41(5):572-8. doi: 10.1038/ng.312. Epub Apr. 19, 2009. Erratum in: Nat Genet. Jul. 2009;41(7):859.

Vickers et al., Effects of RNA secondary structure on cellular antisense activity. Nucleic Acids Res. Mar. 15, 2000;28(6):1340-7.

Wahlestedt, Natural antisense and noncoding RNA transcripts as potential drug targets. Drug Discov Today. Jun. 2006;11(11-12):503-8.

Wakita et al., Specific inhibition of hepatitis C virus expression by antisense oligodeoxynucleotides. In vitro model for selection of target sequence. J Biol Chem. May 13, 1994;269(19):14205-10.

Wang et al., Conformationally locked nucleosides. Synthesis and hybridization properties of oligodeoxynucleotides containing 2?,4?-C-bridged 2?-deoxynucleosides. Bioorganic and Medicinal Chemistry Letters, Apr. 19, 1999;9(8):1147-50.

Xiao et al., Novel approaches for gene-specific interference via manipulating actions of microRNAs: examination on the pacemaker channel genes HCN2 and HCN4. J Cell Physiol. Aug. 2007;212(2):285-92. Retraction in: J Cell Physiol. Feb. 2012;227(2):877.

Ye et al., Two novel positive cis-regulatory elements involved in green tissue-specific promoter activity in rice (*Oryza sativa* L ssp.). Plant Cell Rep. Jul. 2012;31(7):1159-72. doi: 10.1007/s00299-012-1238-8. Epub Mar. 3, 2012.

Zhang et al., PolyA_DB: a database for mammalian mRNA polyadenylation. Nucleic Acids Res. Jan. 1, 2005;33(Database issue):D116-20.

EP 14835805.4, Mar. 22, 2017, Extended European Search Report.
PCT/US2014/051331, Dec. 5, 2014, International Search Report and Written Opinion.
PCT/US2014/051331, Feb. 25, 2016, International Preliminary Report on Patentability.
EP 16749994.6, Aug. 13, 2018, Extended European Search Report.
PCT/US2016/017826, Jun. 30, 2016, International Search Report and Written Opinion.
PCT/US2016/017826, Aug. 24, 2017, International Preliminary Report on Patentability.

* cited by examiner

```
   1  UGCCCAGCCCGUUUUAAGGACAUUAAGGACAUUAGGCCAAGACCCAGCUUCAUUAUGCAGGUCUGAGGUCUGUUUUUGUGUGUGUUGUUUAUUUU     200
      UUUUAUUCCUGCUUUUUGAGUUGACAGUUGGGCUAUGUGCUAUGUAGACAGUGGCUAUGCACAUGAAUGAUGUGCCCCUUGCCCCUACCUUGCC
 201  UAUGGAAGAUUUUUCGAUUGUCGGAUUUCCUCCUCACAUGAUAUCCCUUAUGCUUUAUAAUGUCUUUAUAAUGCUAUACUGCAAUAACUUUAAAA     400
      AAGCAAAAAUAAUAAGAAGAAAAAUUCCAGGAGGGCAAAAAUGAACAAGUCUUUCAUCUUUAUGAAGGAUUAUGCUUUAGAAGAGACGAAGAGC
 401  UGGUCAACCUGCUCUACACUCCAUGUCUGAUCUCUAAAUGAGGUAGUCUACAAAUGAUGCCUUAUCAGGUCUUAAGUAAAGCUACUUGAGCUC     600
      UUUUAGCAUUGAAGUGCGAAAGCAACACGGGAAGCAACUCACUGGGAAGCAUUGUUCUGACAAUCAUUUGUCACUGGCCUGCACUGGGUCCAGGAG
                                                                                        miR-129-5p
 601  ACCUAGUGCUGUCUCCCACAUAUUCACAGUGUCUGAGUUUUCAAUUUACAAAGGUAAUGGAAUCAGCUGCUACAAGAAUGCA     800
      AAAAAAUCUUCCAAAGACAAGAAAAAAGCCGUUUGUCAAUGACGAGUAGCGAGAUAACGGAGAUGAUCAAACAAAAUCAUGGCAGCGUGCCUUG
 801  UAAACAUGAAGGGCAGACCUGCAGUAAGUCAGGCCGUGGCUGUUGUAAAGAGAGCCCUGGUCUGGAAUGAUAUGUCCAGCAUAUGUCAAAGUGUG     1000
      ACAAGUUCCAAACUGCUGAGUUAGCCUGGACCAAAUGAGAGAGCACAGUUGUGUCUUAGCAAAUGCUGAAUUCCCAGCAUCAGUGGUCAACC
1001  UAACAGGCUAGUCUCUAAUCCCUAUUGGGUAGAUGAUGGGAGAGACAAAGAACAGUUUUUAAGCAGUUUAAGCUGAAACAUUGUGGUGCCCUAUCGU     1200
      GAUUUCAGUUGAAUCAUGUGAAAAUUAGCAUGGUCUUGGGCCGCGUGCCGGUGCCACCUGGACAUAUCCUCCAGCUAAUUCCCCAAGGAGCUGAU
1201  CACCUGAGGUCAGGAGUUCAAGACCAGCCUGGCCAACAUGAUGAAAACCCCGUCUCUACUAAAAAUACAAAAAUUAGCCGGGCAUGGUGGCGCCUG     1400
      UAUCCCAGCUACUCGGGAGGCUGAAGCAGGAGAAUCGCUUGAACCCAGGAGGCUUGAUCGAGCCGAGAUCGCGCCAUUGCACUCCACGUAACCUGGU
1401  GACUGAGGCAAAACUCCGUCUCAAAAUAAUUAACAAUAACAAUAAUAAUAGCCAUCCCUUUAUUGUACCUGGUACCUUAUGUAUCGUAUUAUACCACAU miR-17
      miR-106a
      miR-106b
      miR-20b
      miR-20a
      miR-519d
      miR-93
                                                                                      miR-410
1601  UACCUCAUUUUAAUUUACUGCACUUUAUAUCAAGGACUCCAGGACUCAGGAGCUGUGGGUACCUUAUGCUCAGUUAUGCUCAAAGUUAUAUUUUC     1600
      UUACUUAAAGAAGGAUUAUAGUGGCUGGGCAUGUCGGGCCAUGGUAGCCGUGUAAUCCUGGUACCCAGGAGACGGAAUCGCUUGACCCCAGGC
      GGAGGAGGUUACAGUGAGCCGAGAUCGUGCCAGAUCGGCGACACUGCAGCCUGGGCGACCGAGACUCCGUCUCAAAAAAAAAAAAAGGGUUUAUAUAAGAAGUUGUAUU     1800
```

FIG. 1B

```
      miR-222
      miR-221
1801  AAUAUGUAGCAAAGGCUUUCCAAGGUGCAUUAAGUCAUGGGAGCAGUGGCAUAUACCUAUAGUCCAGCUGCACAGGAG
      GCUGAGACAGGAGCAUUGCCUUCAGCCAGGAAUUGGAGACAGCCGAACAGCCUAUCUCUUAAAAAAAGAAAAAACCUAUAUA   2000
                                                          miR-590-3p
2001  AUAAAACAGUAUAAACAAAAGCUAAAUAGGAGUAAAAAAUAUUUUCGAAAUAAAAAAUAUUGGAGUUGUGAAUGUGGCAAAUGUUAAGUCCAGUAGGCCAGUG
      CCAGUGAGAAAAUAAAAAACAUCUAAUGUGAAGUUUGCAUCGUACAUGUGCCUUCACUGAAAGUUUCACUCCACUAGACUUAGAACUCGGUGACA   2200

2201  UGAUGUACUCCCUUAUCUGGACACAGAGGUAUGCAAAAAGAGGUAUGCAGUGGCAGUCUGCACAAAGUGGAAGAAUCUCGGCCUAUAGGGGUC
      CUUGUGGGCCCAGCCUUCAGCCCUAUCAGGCCUAUUUAACUUUCAUUUGUAUACUCCUCAUUUGGUUUGAUAUCUGUUCCAAGGCAGUGGAGAUCCCCAUUUA   2400

2401  AGGAAGAAAAGGGCCUGGCACCUGGCUCAUGCCCUGUAAUCCCAGCACUUUGGGAGGCCGAGGCUGGGCGGAUCGAGGUCAAGAGAUCACCUGAGGUCAAGACCA
      GCCUGGCCAACAUGGCAAAUCCCGUCUCUACUAAAAAAUACAAAAAUUGGCCGGGCGUGGUGGCGUGUGCCUGUAAUCCCAGCUACUCAGGAGGCUGA   2600

2601  GGCAGGAGAAUCGCUUGAACCUGGGAGGUGGAGGUUGCAGUGAGCCGAGAUCACCAUCACUGCACUCCAGCCUGGGCCAACAGAGCCAUACUCCGUCUCAAA
      UAAAUAAAUAAAUAAAUAAAGGACUUCAAACAGCAGCCAGGGAACAGCUUGAGAAUCAAAAUCAUAUUGUCGAAGAACUGGAAAGUACCACUGU   2800

2801  GUGUACCAAUAGCCUCCCCACCACUGGGCACCUAUGGCGGAAGGAUGUCCAGUCAUGUCCUCCAGGAGCGAGCGAGUUCCAGGAAAAGGUUA
      UUAAAUAUUCACUGUAACUGGAGGAGUGAGGAAAUGCAAUCUUAGACAAACUUAGAAAACAUAUGACCCCCCUAUUUUUUGAGACAGGAUCUCA   3000

3001  CUUUGGCACUCAGGCUGGAGUGCAGUGGCACAAUCAUAGCUCACUGCACCUCGACACCUCCCUUGGGGCUCAAGUGAUCCCCCACCGGCCUGGCCACCCAUA
      GCUGGCUAAUUUGUCUAUUUUUUGUAGAGAUGGGGUUUCACCAUGUUAGCCCAGGCUGUCUCAACACUUAGCUCCUUGAGGUGGUAGAACCUCAGCCACAGA   3200

3201  CCAAGAUGCUGGGAUUACAGGUGUGUGCCACAGUGCCCACAGCGUUCCACAGGUGGUACAACUGCUAUAAAGCUUCUUUCUGAUAUUUUCAGUCUAUUUCACUUGAUUGCUCAGUGUAUGAUACAAAUACACAAUUAGCUCGUAUUUGAUCCUGAUUCCCAUAGGCACAUGAGA
                                                                                                             miR-329
                                                                                                             miR-362-3p
3401  AAAUAAAAUGUUCUGGCCAUGACUUAUUUAGCUCUCUGGAAUUGAGGAAUGAGGUGUAAAAAGAAGAGGAAAUGAGGAUCACAAAUUUAGA
                                                                                   miR-136
3601  AUUUAAUCGAACUCGCUCUCUACUCUUGUGUUGUAGAACACUGACAGUGGCCUCCUACUGGUUUUUUUUAAUCUAUAAAUGGAGAUAUCUAACAUGUUG
      AGCCUGGCCCCACUGCAAAGCACUCCUGACUCCAGUGAUGAGUACUCAGUCUCGAUCAACUAUUCAUAUUCCACAUUG   3600
           miR-26b
           miR-26a
           miR-1297
3601  GAGGACUUCCUCCCAAAUGGAUGCGGAUCUCCCUACCUGAACUUCAACCUAAACAAAUACCAGUUGACUUACUCGUAUUGAUCCCUG
      GAACCAUUUAUCCUGUGCUUACCAUGCUUUAUUUGAUCUCUUUCAUACCUUCAAAACUAUUUAGCCAAUUUAAAAUUUGACAGUUGCCAUUA   3800
```

FIG. 1C

```
3801 AAUAUAGGUUUACAAUAUGCUUUAUCCAGUAUACCUGCCCAAAUUCUGACAGAUGCUUUUGCACCUCUAAGGAAGACCCAUGUUCAUAGUGAUGG   4000
     AGUUUGUGUGGACUACCAUGCGGUUGCCAAGGUUGCCAAGAAAUGCGUUUAAAGUCACACUACUAGGAGAAAGUAAUUUAGUCCGUCCAGUUG
     miR-455-5p
4001 GAUCCUUGGCACAUAGUUAUCUCUGCUAGAACAAACUAAACAGCCAGGAGACAAGAGGGCAAAGUUUGCUCUGUGAGUUUUAGUCCGUCCAGGCU   4200
     UAAAUUAUGCUGUCAAAUCGACGAUCUGGGCCUCACUAUAGAGUUCAUGAAAUGCCUUUUGUGUAUAGAGACAGAGUCUUGCUCUGUGAGUCCAG
4201 GGAGUGCAGUGGCAGUGGCUCUCAAAUCGACGAUCUGGGCCUCACUAUAGAGUUCAUGAAAUGCCAAUUCUCCUGGGUUCAAGCGAUUCUCCUGCCU   4400
     GCCACCACACCCGGCUAAUUUUUGUAUAGAGACGGGUUCACCAUGCCAGGCUAAUUCUUGAACUCCUGACCUCAAGUGAUCAAUCCACCUGCCU
4401 CCGCCCUCCAAAGUGCUGGGAUUACAGGCGUGAGCCACCAGGCCCUUUGGAAGUCUAAUCCCGCAUCCGCUACAGAGACAGAAUCCAAGACUGGAG   4600
     UGCAUCCCGAAGUCACCUGACUCAGUGCCCCUUUGGAAGUUUAAGGAAGCAAGCCGAAGAUUUAUUAGACAGAAUCCAAGAAUCCAAGCUCAUAU
4601 GUUCCAUCUUCUCUGGCUGUAUAGGCCAGCAGAUAAAAUUGGCCUCCAAACACUUCUCCUGUGAAUGUUAUGAGCGCUCCAGGAGUACUAGUGCAAGCAAG   4800
     AACAUCAGCACCAGCAGUAAACCUAAGCUUCAAACAUCUGUGAUCUUCCUGUGAAUGUUAUGAGCGCUCCAGGAGUACUAGUGCAAG
4801 AAGGGCCUCUGCUGUUCUUUGAGGACAUUAACCGGUAAAAUUGACCUUGACCUUGAGUUCGAGUUAGAGGUCCAGUUAAGCCUCCUGGACACGGUUG   5000
     CUCACCUGUAAUCCCAGGUGAGGCUGAGCGCUACUGGGAAUCCGAGGCUGAGGAAUUGCCUGAACAUGGUAAAACCCGCCU
5001 CUACUAAAAAUACAAAAAUAGCUGGGCGAUGUGGCACACACCUGCCUCAGCUACUCCAAUGCCUUAUCCCAGGAGGCUGAGGAGGAAUGCUUGAGGCUUGAGCUAAAGGUGUGG   5200
     GAGGCAGUGAGCCAGGAUUACACCACUGCACUCCAGCCUGGGUGACAAGCCAUAUCCUACCGACUCUAUGAUGCUAUGCUAUGUCUUAAG
5201 UGUAAAGGUGGCUAAAUAUAUAGAAAAUCCUAAGACUGAUUUCCAAUAUCCCCAAGCAGAGAUAAUACAAUGAAGUGAAUACACAGAUUGUCCAA   5400
     AAGAAAAUGCUUAAGCUAGCUACGUGAUCUACAGUAUCUGUACACAGGACAUUUCAGAAUACUAGGAAGUGAAUGUACUAGUAGUUGGAGUCAGAUUUCU
5401 CUGUAAGCGUCCUAGGCCAUUGAGACUGCACCUGACAUCCGCUGGAUUUCUAGCAGGUUUGCACUAUCCAGGUUGGAGCAUUGGAAGUGCCACUGACAGUAUG   5600
     CAAACCGUCCAGAGCAUUACCUGACUUGCUGCUGGAUCCUGUGCCAGUCCAGCAUGUUUUCACUGGAUGGAACUCAGUAAGUUCACCGGAAAGUUUCACCUUAAAUCUG
5601 CCCCUCUCCUGCCCGGUCCCAGAGCCUUCCCGUCCAUCAGGCUGCCAUCAUUUUCACCUGGAGGAGCUUUCCACCUUCUCCUCCCUUUUCUCUCCCCCAU   5800
     CAUCUAGCUACACAGUCCAGGGUAAGCUCAGAAAGGCAAUCUGUCAGAAGGACAAUCUGAGACACUAGCCAAUUCAGAGUUCCUAGCCCUGAAAAAAUG
5801 UGCUUUUUCUGACUACUCAGAUUGGCCACACUGUCUGCUAUUUCAGGGCUCUCGUGAUGGCUCUCCACAUUUGGACCAAUCCCACUCUCCUUGACCCAUUUGAUCCCUUGCCAAUCCCAAAAUCCCC   6000
     AGAUCCUAAGUCGUCUCGCUAUGUUCACGGGCACUGUGUGAUAUUCCAGGCUCUCGUUCCAGUGAUGCGGCCUUGGUCGUUCCCUGAUGUGCCCUGAUUGGACCAUCUGCAAUCCCCGGGGUA
6001 GAUUCUACCCUGAAAAUGUCCGAAAAAUGUUCGACCAGCCUGCGGCAGCCUUGCCACACCCCACUACACUACACUUUUGGACCCUUGAUGUCCUGGCAUCGAGCCAUUCCCACGGGGUACC   6200
     AUGUUUGUCUCUUGGCCAGCACCUACACCAUGCCCGGCGGACGAGGCUAGGAGGACCUCCCUGCCCUCCUGCGAGGACUAGCCAAUGCCAUCUCCUGCCCUGGGGUA
```

FIG. 1D

HYBRID OLIGONUCLEOTIDES AND USES THEREOF

CROSS-REFERENCE TO RELATED APPLICATIONS

This application is a national stage filing under U.S.C. § 371 of PCT International Application No. PCT/US2016/017790, with an international filing date of Feb. 12, 2016, which claims the benefit under 35 U.S.C. § 119(e) of U.S. Provisional Application No. U.S. 62/115,754, entitled "HYBRID OLIGONUCLEOTIDES AND USES THEREOF", filed on Feb. 13, 2015, the contents of each of which are incorporated herein by reference in its entirety.

FIELD OF THE INVENTION

The invention relates in part to oligonucleotide based compositions, as well as methods of using oligonucleotide based compositions to modulate gene expression.

BACKGROUND OF THE INVENTION

A considerable portion of human diseases can be treated by selectively altering protein and/or RNA levels of disease-associated transcription units. Such methods typically involve blocking translation of mRNAs or causing degradation of target RNAs. However, additional approaches for modulating gene expression are desirable, including methods for increasing expression levels of genes.

SUMMARY OF THE INVENTION

According to some aspects of the invention, compositions are provided that comprise one or more oligonucleotides that promote cleavage (e.g., via endonuclease activity) of a target nucleic acid at one position while protecting the nucleic acid from cleavage (e.g., via exonuclease activity) at another position. Such compositions are useful for selectively alternating the structure of a target nucleic acid. For example, in some embodiments, compositions provided herein are useful for selectively processing an RNA (e.g., mRNA) to remove one or more portions of the target RNA, such as, for example, an expanded repeat region or an miRNA interacting region or other regulatory region. In some embodiments, removal of these portion(s) stabilizes the target RNA and/or increases steady state levels of the target RNA in cells. In instances where the target RNA encodes a protein, increases in steady state levels of the RNA in cells have been found to result in a concomitant increase in corresponding protein levels. Accordingly, in some embodiments, methods for targeted design of oligonucleotides are provided that can be used to alter protein and/or RNA levels and/or the structure of transcription units in a targeted and specific manner. In some embodiments, hybrid oligonucleotides are provided that combine both protecting and targeted RNA degrading characteristics.

In some embodiments, a single stranded oligonucleotide is provided comprising a region that promotes cleavage of a first target nucleic acid (e.g., a gapmer region) and a region that protects a second nucleic acid from exonuclease activity (e.g., a steric blocking region, a mixmer region), in which the first and second nucleic acid are adjacent to each other (e.g., adjacent regions on a target RNA). In some embodiments, it has been discovered that such "hybrid" oligonucleotides are useful for selectively cleaving a portion of an RNA (such as a portion of an mRNA), while protecting the end exposed by the cleavage event from further degradation by exonucleases. In some embodiments, the result of this selective cleavage and the protection of the resultant cleaved RNA is an increase in the level of cleaved RNA in the cell. Such oligonucleotides are useful, e.g., to selectively remove an undesirable portion of an RNA, such as a portion containing a repeat region and/or a region containing several regulatory sequences.

Accordingly, in some embodiments, a single stranded oligonucleotide is provided, comprising a region that promotes cleavage of a first target nucleic acid (e.g., a gapmer region) and a region that protects a second nucleic acid from exonuclease activity (e.g., a mixmer region), where the first and second nucleic acid are adjacent to each other (e.g., adjacent regions on a target RNA).

It is also contemplated that the region that promotes cleavage (e.g., a mixmer) and the protective region (e.g., a gapmer) may be contained within separate oligonucleotides, which may be comprised within a composition and optionally connected via a linker.

In some aspects, a composition is provided comprising:
(i) a first single stranded oligonucleotide having the general formula:

$(X_m^1\text{-}X_n^2\text{-}X_o^3)$, wherein each instance of $X^1$, $X^3$ is independently a modified or unmodified nucleotide, wherein m and o are independently integers in a range of 1 to 10, reflecting the number of instances of $X^1$ and $X^3$, respectively, linked consecutively together through internucleotide linkages, wherein each instance of $X^2$ is a deoxyribonucleotide, wherein n is an integer in a range of 6 to 20, reflecting the number of instances of $X^2$ linked consecutively together through internucleotide linkages; and
(ii) a second single stranded oligonucleotide of 4 to 40 nucleotides in length having the general formula:

$(X_p^4\text{-}X_q^5)_r$, wherein each instance of $X^4$ is a modified or unmodified nucleotide, wherein each instance of $X^5$ is a deoxyribonucleotide, wherein p and q are independently 0 or 1, reflecting the number of instances of $X^4$ and $X^5$, respectively, wherein at least one of $X^4$ and $X^5$ is present in each instance of the unit, $(X_p^4\text{-}X_q^5)$, wherein r is an integer from 2 to 20 reflecting the number of instances of the unit, $(X_p^4\text{-}X_q^5)$, linked together through internucleotide linkages, wherein the second single stranded oligonucleotide does not contain a sequence of more than 2, more than 3, more than 4, or more than 5 consecutive deoxyribonucleotides, and wherein the symbol "-" denotes an internucleotide linkage.

In some embodiments, the first single stranded oligonucleotide and the second single stranded oligonucleotide are complementary to adjacent sites of a target RNA. In some embodiments, the RNA is an mRNA.

In some embodiments, the first single stranded oligonucleotide is covalently linked to the second single stranded oligonucleotide. In some embodiments, the first single stranded oligonucleotide is linked to the second single stranded oligonucleotide through an internucleotide linkage in the following orientation:

$5'(X_m^1\text{-}X_n^2\text{-}X_o^3)\text{-}(X_p^4\text{-}X_q^5)_r 3'$.

In some embodiments, the first oligonucleotide comprises a region of complementarity that is complementary with a portion of the 3' UTR of a target mRNA. In some embodiments, the portion of the 3' UTR of a target mRNA is 5' to one or more miRNA binding elements of the target mRNA.

In some embodiments, the portion of the 3' UTR of a target mRNA is 5' to a repeat region of the target mRNA. In some embodiments, the repeat region comprises repeating CUG triplets. In some embodiments, the 3' UTR is in a range of 10 nucleotides to 30000 nucleotides in length.

In some embodiments, the first single stranded oligonucleotide is linked to the second single stranded oligonucleotide through an internucleotide linkage in the following orientation.

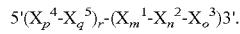

$5'(X_p^4-X_q^5)_r-(X_m^1-X_n^2-X_o^3)3'$.

In some embodiments, the first oligonucleotide comprises a region of complementarity that is complementary with a portion of the 5' UTR of a target mRNA. In some embodiments, the portion of the 5' UTR of a target mRNA is 3' to a repeat region of the target mRNA. In some embodiments, the repeat region comprises repeating CGG, CCG, or CUG triplets.

In some embodiments, at least one of $X^1$, $X^3$ or $X^4$ is a 2'-modified nucleotide. In some embodiments, the 2'-modified nucleotide is a 2'-O,4'-C— bridged nucleotide. In some embodiments, the 2'-modified nucleotide is a 2'-O,4'-C— methylene bridged nucleotide.

In some embodiments, the composition comprises at least one $X^4$ that is a 2'-modified nucleotide. In some embodiments, the a 2'-modified nucleotide is a 2'-O-methyl nucleotide.

In some embodiments, the composition comprises at least one $X^4$ that is a 2'-O-methyl nucleotide, wherein at least one of $X^1$ or $X^3$ is a 2'-O,4'-C— methylene bridged nucleotide.

In some embodiments, the nucleotides of $X^1$, $X^3$ and/or $X^4$ are ribonucleotides.

In some embodiments, the first single stranded oligonucleotide and the second single stranded oligonucleotide are complementary to adjacent sites of a FXN mRNA. In some embodiments, the adjacent sites of the FXN mRNA are located within the 3' UTR of the FXN mRNA.

In other aspects, a method of modulating gene expression in a cell is provided, the method comprising delivering to a cell a composition as described herein, such as in any one of the embodiments above. In some embodiments, modulating gene expression is upregulation gene expression.

In another aspect, a method of modulating gene expression in a subject is provided, the method comprising delivering to a cell a composition as described herein, such as in any one of the embodiments above. In some embodiments, modulating gene expression is upregulation gene expression.

In other aspects, a method of treating a disease or condition associated with decreased gene expression is provided, the method comprising delivering to a cell a composition as described herein, such as in any one of the embodiments above. In some embodiments, the decreased gene expression is decreased FXN expression and wherein the subject has Friedreich's ataxia.

In some aspects, a single stranded oligonucleotide of 8 to 50 nucleotides in length is provided, the oligonucleotide comprising a gapmer region and a mixmer region. In some embodiments, the gapmer region is complementary with at least 5 contiguous nucleotides of an RNA and the mixmer region is complementary with a region adjacent to the at least 5 contiguous nucleotides. In some embodiments, the RNA is an mRNA. In some embodiments, the gapmer region is complementary with at least 5 contiguous nucleotides of a 5' UTR or a 3' UTR of the mRNA. In some embodiments, the gapmer region is complementary with at least 5 contiguous nucleotides of an RNA and mixmer region is complementary with a region adjacent to the at least 5 contiguous nucleotides. In some embodiments, the RNA is an mRNA. In some embodiments, the gapmer region is complementary with at least 5 contiguous nucleotides of a 5' UTR or a 3' UTR of the mRNA. In some embodiments, the gapmer region is complementary with at least 5 contiguous nucleotides of the 3' UTR of the mRNA. In some embodiments, the portion of the 3' UTR of the mRNA is 5' to one or more miRNA binding elements of the mRNA. In some embodiments, the at least 5 contiguous nucleotides of the 3' UTR of the mRNA is 5' to a repeat region of the mRNA. In some embodiments, the repeat region comprises repeating CUG triplets. In some embodiments, the 3' UTR is in a range of 10 nucleotides to 30000 nucleotides in length. In some embodiments, the gapmer region is complementary with at least 5 contiguous nucleotides of the 5' UTR of the mRNA. In some embodiments, the at least 5 contiguous nucleotides of the 5' UTR of the mRNA is 3' to a repeat region of the mRNA. In some embodiments, the repeat region comprises repeating CGG, CCG, or CUG triplets. In some embodiments, the mRNA is a FXN mRNA. In some embodiments, the gapmer region is complementary with at least 5 contiguous nucleotides of a 3' UTR of the FXN mRNA.

In other aspects, a single stranded oligonucleotide is provided comprising the general formula (A)-(B), wherein:
(A) comprises the formula 5'-$X_1$-$X_2$-$X_3$-3', wherein $X_2$ is 6 to 20 deoxyribonucleotides and $X_1$ and $X_3$ are each independently 1-10 modified nucleotides; and
(B) comprises 5 to 20 nucleotides that when hybridized with a target nucleic acid protect the target nucleic acid from exonuclease mediated degradation in the region of hybridization.

In some embodiments, B contains one or more of the following modification patterns:
(a) (X)Xxxxxx, (X)xXxxxx, (X)xxXxxx, (X)xxxXxx, (X)xxxxXx and (X)xxxxxX,
(b) (X)XXxxxx, (X)XxXxxx, (X)XxxXxx, (X)XxxxXx, (X)XxxxxX, (X)xXXxxx, (X)xXxXxx, (X)xXxxXx, (X)xXxxxX, (X)xxXXxx, (X)xxXxXx, (X)xxXxxX, (X)xxxXXx, (X)xxxXxX and (X)xxxxXX,
(c) (X)XXXxxx, (X)xXXXxx, (X)xxXXXx, (X)xxxXXX, (X)XXxXxx, (X)XXxxXx, (X)XXxxxX, (X)xXXxXx, (X)xXXxxX, (X)xxXXxX, (X)XxXXxx, (X)xXxXXx, (X)xXxxXX, (X)XxXxXx, (X)XxXxxX (X)xXxXxX, (X)xXxxXX, (X)xxXxXx, (X)xXxxXx and (X)XxXxXx,
(d) (X)xxXXX, (X)xXxXXX, (X)xXXxXX, (X)xXXXxX, (X)xXXXXx, (X)XxxXXX, (X)XxXxXX, (X)XxXXxX, (X)XxXXXx, (X)XXxxXX, (X)XXxXxX, (X)XXxXXx, (X)XXXxxX, (X)XXXxXx, and (X)XXXXxx,
(e) (X)xXXXXX, (X)XxXXXX, (X)XXxXXX, (X)XXXxXX, (X)XXXXxX and (X)XXXXXx, and
(f) XXXXXX, XxXXXXX, XXxXXXX, XXXxXXX, XXXXxXX, XXXXXxX and XXXXXXx, wherein X denotes a modified nucleotide, (X) denotes an optional modified nucleotide, and x denotes a DNA or RNA nucleotide.

In some embodiments, A is complementary with at least 5 contiguous nucleotides of an RNA and B is complementary with a region adjacent to the at least 5 contiguous nucleotides. In some embodiments, the RNA is an mRNA. In some embodiments, A is complementary with at least 5 contiguous nucleotides of a 5' UTR or a 3' UTR of the mRNA. In some embodiments, A is complementary with at least 5 contiguous nucleotides of the 3' UTR of the mRNA. In some embodiments, the portion of the 3' UTR of the mRNA is 5' to one or more miRNA binding elements of the mRNA. In some embodiments, the at least 5 contiguous nucleotides of the 3' UTR of the mRNA is 5' to a repeat region of the mRNA. In some embodiments, the repeat region comprises repeating CUG triplets. In some embodiments, the 3' UTR is in a range of 10 nucleotides to 30000 nucleotides in length. In some embodiments, A is complementary with at least 5 contiguous nucleotides of the 5' UTR of the mRNA. In some embodiments, the at least 5 contiguous nucleotides of the 5' UTR of the mRNA is 3' to a repeat region of the mRNA. In some embodiments, the repeat region comprises repeating CGG, CCG, or CUG triplets. In some embodiments, the mRNA is a FXN mRNA. In some embodiments, A is complementary with at least 5 contiguous nucleotides of a 3' UTR of the FXN mRNA.

In other aspects, a method of modulating gene expression in a cell is provided, the method comprising delivering to a cell an oligonucleotide as described herein, such as in any one of the embodiments above. In some embodiments, modulating gene expression is upregulation gene expression.

In another aspects, a method of modulating gene expression in a subject is provided, the method comprising delivering to a cell an oligonucleotide as described herein, such as in any one of the embodiments above. In some embodiments, modulating gene expression is upregulation gene expression.

In other aspects, a method of treating a disease or condition associated with decreased gene expression is provided, the method comprising delivering to a cell an oligonucleotide as described herein, such as in any one of the embodiments above. In some embodiments, the decreased gene expression is decreased FXN expression and wherein the subject has Friedreich's ataxia.

Yet other aspects provide a single stranded oligonucleotide having a sequence as set for in Table 3 or 5. In other aspects, a method of modulating gene expression in a cell is provided, the method comprising delivering to a cell a single stranded oligonucleotide having a sequence as set for in Table 3 or 5.

The details of one or more embodiments of the invention are set forth in the description below. Other features or advantages of the present invention will be apparent from the following drawings and detailed description of several embodiments, and also from the appending claims.

BRIEF DESCRIPTION OF THE DRAWINGS

The following drawings form part of the present specification and are included to further demonstrate certain aspects of the present disclosure, which can be better understood by reference to one or more of these drawings in combination with the detailed description of specific embodiments presented herein.

FIGS. 1B, 1C, and 1D are diagrams showing the location of conserved miRNA binding sites in the 3'UTR of FXN (SEQ ID NO: 25).

DETAILED DESCRIPTION OF THE INVENTION

Figure 1A:
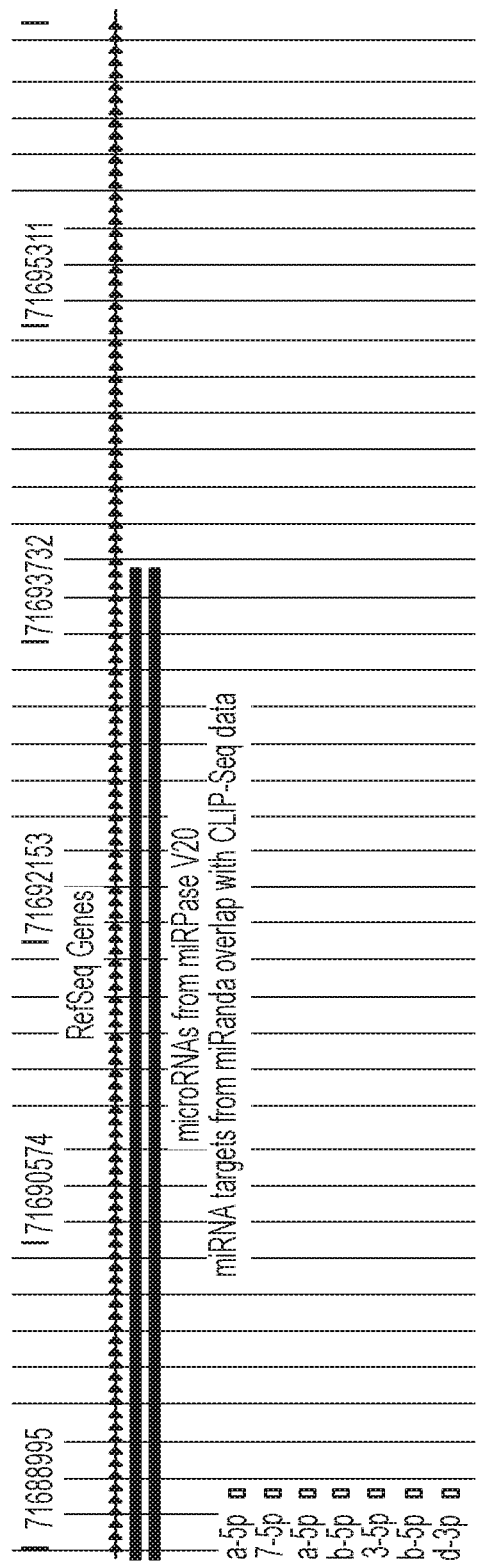
FIG. 1A is a diagram showing the 3'UTR of FXN and miRNA binding sites included in the 3'UTR.

Aspects of the invention relate to compositions are provided that comprise one or more oligonucleotides that promote cleavage (e.g., via endonuclease activity) of a target nucleic acid at one position while protecting the nucleic acid from cleavage (e.g., via exonuclease activity) at another position. In some embodiments, a single stranded oligonucleotide comprising a region that promotes cleavage of a first target nucleic acid (e.g., a gapmer region) and a region that protects a second nucleic acid from exonuclease activity (e.g., a protecting region), where the first and second nucleic acid are adjacent to each other (e.g., adjacent regions on a target RNA). As described herein, it has been discovered that treatment of cells with oligonucleotides containing a cleavage region and a protection region resulted in an increase in gene expression. Without wishing to be bound by theory, it is believed that these "hybrid" oligos allow for selective cleavage of a portion of an RNA (such as a portion of a 5' UTR or 3'UTR of an mRNA), while protecting the end exposed by the cleavage event from further degradation by exonucleases. In some embodiments, oligos designed in this manner can be of various lengths (e.g., 14-30 nucleotides in length).

In some embodiments, instead of one "hybrid" oligonucleotide that has a protecting portion (e.g., mixmer) and a cleavage promoting portion (e.g., gapmer) covalently attached, separate oligonucleotides having such portions can be used together to achieve similar protection against RNA degradation (e.g., via gapmer cleavage) on one or both sides of a cut site. In some embodiments, such oligonucleotides can be combined in various ratios depending on oligonucleotide efficacy, in vivo distribution and other factors. Each oligonucleotide (e.g., mixmer and gapmer oligonucleotides) may be administered at the same time or sequentially.

Oligonucleotides

Aspects of the disclosure relate to single stranded oligonucleotides. In some embodiments, a composition is provided comprising a first single stranded oligonucleotide containing a cleavage promoting region (such as a gapmer region) and a second oligonucleotide containing an protecting region (e.g., a steric hindrance region such as a mixmer region that provides protection from exonucleases). In some embodiments, a single stranded oligonucleotide is provided comprising a cleavage promoting region (such as a gapmer region) and an protecting region (e.g., a steric hindrance region such as a mixmer region that provides protection from exonucleases).

In some embodiments, an protecting oligonucleotide or a protecting region thereof described herein may be a mixmer or comprise a mixmer sequence pattern. In some embodiments, the "mixmer," may comprise both naturally and non-naturally occurring nucleotides or comprise at least two different types of non-naturally occurring nucleotides, for example. In some embodiments, the mixmer may contain one or more modified nucleotides, such that they have a higher binding affinity than unmodified oligonucleotides and may be used to specifically bind a target molecule, e.g., to block a binding site on the target molecule. Generally, a protecting oligonucleotide or a protecting region thereof does not recruit an RNAse to the target molecule and thus does not promote cleavage of the target molecule.

In some embodiments, a protecting oligonucleotide (e.g., mixmer) comprises or consists of a repeating pattern of nucleotide analogues and naturally occurring nucleotides, or one type of nucleotide analogue and a second type of nucleotide analogue. However, it is to be understood that the protecting oligonucleotides need not comprise a repeating pattern and may instead comprise any arrangement of nucleotide analogues and naturally occurring nucleotides or any arrangement of one type of nucleotide analogue and a second type of nucleotide analogue. It is to be understood that a pattern, in general, refers to a pattern of modifications or lack thereof, and not to a pattern of A, T, C, G, or U nucleotides. The repeating pattern, may, for example be every second or every third nucleotide is a nucleotide analogue, such as LNA or, and the remaining nucleotides are naturally occurring nucleotides, such as DNA, or are a 2' substituted nucleotide analogue such as 2'-O-methyl, 2'MOE or 2' fluoro analogues, or any other nucleotide analogues described herein. It is recognised that the repeating pattern of nucleotide analogues, such as LNA units, or 2'-O-methyl, 2'MOE or 2' fluoro analogues, may be combined with nucleotide analogues at fixed positions—e.g. at the 5' or 3' termini.

In some embodiments, a protecting oligonucleotide does not comprise a region of more than 5, more than 4, more than 3, or more than 2 consecutive naturally occurring nucleotides, such as DNA nucleotides. In some embodiments, a protecting oligonucleotide comprises at least a region consisting of at least two consecutive nucleotide analogues, such as at least two consecutive LNAs. In some embodiments, a protecting oligonucleotide comprises at least a region consisting of at least three consecutive nucleotide analogue units, such as at least three consecutive LNAs.

In some embodiments, a protecting oligonucleotide does not comprise a region of more than 7, more than 6, more than 5, more than 4, more than 3, or more than 2 consecutive nucleotide analogues, such as LNAs. It is to be understood that the LNA units may be replaced with other nucleotide analogues, such as those referred to herein.

In some embodiments, a protecting oligonucleotide comprises at least one nucleotide analogue in one or more of six consecutive nucleotides. The substitution pattern for the nucleotides may be selected from the group consisting of Xxxxxx, xXxxxx, xxXxxx, xxxXxx, xxxxXx and xxxxxX, wherein "X" denotes a nucleotide analogue, such as an LNA, and "x" denotes a naturally occurring nucleotide, such as DNA or RNA.

In some embodiments, a protecting oligonucleotide comprises at least two nucleotide analogues in one or more of six consecutive nucleotides. The substitution pattern for the nucleotides may be selected from the group consisting of XXxxxx, XxXxxx, XxxXxx, XxxxXx, XxxxxX, xXXxxx, xXxXxx, xXxxXx, xXxxxX, xxXXxx, xxXxXx, xxXxxX, xxxXXx, xxxXxX and xxxxXX, wherein "X" denotes a nucleotide analogue, such as an LNA, and "x" denotes a naturally occurring nucleotide, such as DNA or RNA. In some embodiments, the substitution pattern for the nucleotides may be selected from the group consisting of XxXxxx, XxxXxx, XxxxXx, XxxxxX, xXxXxx, xXxxXx, xXxxxX, xxXxXx, xxXxxX and xxxXxX. In some embodiments, the substitution pattern is selected from the group consisting of xXxXxx, xXxxXx, xXxxxX, xxXxXx, xxXxxX and xxxXxX. In some embodiments, the substitution pattern is selected from the group consisting of xXxXxx, xXxxXx and xxXxXx. In some embodiments, the substitution pattern for the nucleotides is xXxXxx.

In some embodiments, a protecting oligonucleotide comprises at least three nucleotide analogues in one or more of six consecutive nucleotides. The substitution pattern for the nucleotides may be selected from the group consisting of XXXxxx, xXXXxx, xxXXXx, xxxXXX, XXxXxx, XXxxXx, XXxxxX, xXXxXx, xXXxxX, xxXXxX, XxXXxx, XxxXXx, XxxxXX, xXxXXx, xXxxXX, xxXxXX, xXxXxX and XxXxXx, wherein "X" denotes a nucleotide analogue, such as an LNA, and "x" denotes a naturally occurring nucleotide, such as DNA or RNA. In some embodiments, the substitution pattern for the nucleotides is selected from the group consisting of XXxXxx, XXxxXx, XXxxxX, xXXxXx, xXXxxX, xxXXxX, XxXXxx, XxxXXx, XxxxXX, xXxXXx, xXxxXX, xxXxXX, xXxXxX and XxXxXx. In some embodiments, the substitution pattern for the nucleotides is selected from the group consisting of xXXxXx, xXXxxX, xxXXxX, xXxXXx, xXxxXX and xXxXxX. n some embodiments, the substitution pattern for the nucleotides is xXxXxX or XxXxXx. In some embodiments, the substitution pattern for the nucleotides is xXxXxX.

In some embodiments, a protecting oligonucleotide comprises at least four nucleotide analogues in one or more of six consecutive nucleotides. The substitution pattern for the nucleotides may be selected from the group consisting of xXXXX, xXxXXX, xXXxXX, xXXXxX, xXXXXx, XxxXXX, XxXxXX, XxXXxX, XxXXXx, XXxxXX, XXxXxX, XXxXXx, XXXxxX, XXXxXx and XXXXxx, wherein "X" denotes a nucleotide analogue, such as an LNA, and "x" denotes a naturally occuring nucleotide, such as DNA or RNA.

In some embodiments, a protecting oligonucleotide comprises at least five nucleotide analogues in one or more of six consecutive nucleotides. The substitution pattern for the nucleotides may be selected from the group consisting of xXXXXX, XxXXXX, XXxXXX, XXXxXX, XXXXxX and XXXXXx, wherein "X" denotes a nucleotide analogue, such as an LNA, and "x" denotes a naturally occurring nucleotide, such as DNA or RNA.

The oligonucleotide may comprise a nucleotide sequence having one or more of the following modification patterns.

(a) (X)Xxxxxx, (X)xXxxxx, (X)xxXxxx, (X)xxxXxx, (X)xxxxXx and (X)xxxxxX, (b) (X)XXxxxx, (X)XxXxxx, (X)XxxXxx, (X)XxxxXx, (X)XxxxxX, (X)xXXxxx, (X)xXxXxx, (X)xXxxXx, (X)xXxxxX, (X)xxXXxx, (X)xxXxXx, (X)xxXxxX, (X)xxxXXx, (X)xxxXxX and (X)xxxxXX, (c) (X)XXXxxx, (X)xXXXxx, (X)xxXXXx, (X)xxxXXX, (X)XXxXxx, (X)XXxxXx, (X)XXxxxX, (X)xXXxXx, (X)xXxXxx, (X)xXxxXx, (X)xXxxXxX, (X)XxXxxx, (X)XxxXXx (X)XxxxXX, (X)xXxXXx, (X)xXxxXX, (X)xxXxXX, (X)xXxXxX and (X)XxXxXx, (d) (X)xxXXX, (X)xXxXXX, (X)xXXxXX, (X)xXXXxX, (X)xXXXXx, (X)XxxXXX, (X)XxXxXX, (X)XxXXxX, (X)XxXXXx, (X)XXxXXx, (X)XXxxXX, (X)XXxXxX, (X)XXXxxX, (X)XXXxXx, and (X)XXXXxx, (e) (X)xXXXXX, (X)XxXXXX, (X)XXxXXX, (X)XXXxXX, (X)XXXXxX and (X)XXXXXx, and (f) XXXXXX, XxXXXXX, XXxXXXX, XXXxXXX, XXXXxXX, XXXXXxX and XXXXXXx, in which "X" denotes a nucleotide analogue, (X) denotes an optional nucleotide analogue, and "x" denotes a DNA or RNA nucleotide unit. Each of the above listed patterns may appear one or more times within an oligonucleotide, alone or in combination with any of the other disclosed modification patterns.

In some embodiments, a protecting oligonucleotide contains a modified nucleotide, e.g., an LNA, at the 5' end. In some embodiments, a protecting oligonucleotide contains a modified nucleotide, e.g., an LNA, at the first two positions, counting from the 5' end.

In some embodiments, a protecting oligonucleotide (e.g., mixmer) is incapable of recruiting RNAseH. Oligonucleotides that are incapable of recruiting RNAseH are well known in the literature, in example see WO2007/112754, WO2007/112753, or PCT/DK2008/000344. Protecting oligonucleotides may be designed to comprise a mixture of affinity enhancing nucleotide analogues, such as in non-limiting example LNA nucleotides and 2'-O-methyl nucleotides. In some embodiments, a protecting oligonucleotide comprises modified internucleoside linkages (e.g., phosphorothioate internucleoside linkages or other linkages) between at least two, at least three, at least four, at least five or more nucleotides.

In some embodiments, a protecting oligonucleotide or protecting region of an oligonucleotide is 4 to 40 nucleotides (e.g., 4 to 40, 4 to 35, 4 to 30, 4 to 25, 4 to 20, 4 to 15, 4 to 10, 5 to 40, 5 to 35, 5 to 30, 5 to 25, 5 to 20, 5 to 15, or 5 to 10), in length having the general formula:

$$(X_p^4 - X_q^5)_r,$$

wherein each instance of $X^4$ is a modified or unmodified nucleotide described herein (e.g., a modified or unmodified ribonucleotide described herein), wherein each instance of $X^5$ is a deoxyribonucleotide, wherein p and q are independently 0 or 1, reflecting the number of instances of $X^4$ and $X^5$, respectively, wherein at least one of $X^4$ and $X^5$ is present in each instance of the unit, $(X_p^4 - X_q^5)$, wherein r is an integer from 2 to 20 reflecting the number of instances of the unit, $(X_p^4 - X_q^5)$, linked together through internucleotide linkages, wherein the protecting oligonucleotide or region does not contain a sequence of more than 5 consecutive deoxyribonucleotides, and wherein the symbol "-" denotes an internucleotide linkage.

A protecting oligonucleotide (e.g., mixmer) may be produced using any method known in the art or described herein. Representative U.S. patents, U.S. patent publications, and PCT publications that teach the preparation of protecting oligonucleotides include U.S. patent publication Nos. US20060128646, US20090209748, US20090298916, US20110077288, and US20120322851, and U.S. Pat. No. 7,687,617.

In some embodiments, a cleavage promoting oligonucleotide or cleavage promoting region of an oligonucleotide has a sequence following the general formula:

$$(X_m^1 - X_n^2 - X_o^3),$$

wherein each instance of $X^1$, $X^3$ is independently a modified or unmodified nucleotide described herein (e.g., a modified or unmodified ribonucleotide described herein), wherein m and o are independently integers in a range of 1 to 10 (e.g., 1 to 10, 2 to 10, 3 to 10, 4 to 10, 5 to 10, 6 to 10, 7 to 10, 1 to 9, 2 to 9, 3 to 9, 4 to 9, 5 to 9, 6 to 9, 7 to 9, 1 to 8, 2 to 8, 3 to 8, 4 to 8, 5 to 8, 6 to 8, 7 to 8, 1 to 7, 2 to 7, 3 to 7, 4 to 7, 5 to 7, 1 to 6, 2 to 6, 3 to 6, or 4 to 6) reflecting the number of instances of $X^1$ and $X^3$, respectively, linked consecutively together through internucleotide linkages, wherein each instance of $X^2$ is a deoxyribonucleotide, wherein n is an integer in a range of 6 to 20 (e.g., 6 to 20, 6 to 15, 6 to 10, 7 to 20, 7 to 15, or 7 to 10), reflecting the number of instances of $X^2$ linked consecutively together through internucleotide linkages. The deoxyribonucleotides of $X^2$ may be substituted with, e.g., C4'-substituted nucleotides, acyclic nucleotides, or arabino-configured nucleotides.

In some embodiments, a cleavage promoting oligonucleotide or a region thereof described herein may be a gapmer or comprise a gapmer sequence pattern. A gapmer generally has the formula 5'-X-Y-Z-3', with X and Z as flanking regions around a gap region Y. In some embodiments, the Y region is a contiguous stretch of nucleotides, e.g., a region of at least 6 DNA nucleotides, which are capable of recruiting an RNAse, such as RNAseH. Without wishing to be bound by theory, it is thought that the gapmer binds to the target nucleic acid, at which point an RNAse is recruited and can then cleave the target nucleic acid. In some embodiments, the Y region is flanked both 5' and 3' by regions X and Z comprising high-affinity modified nucleotides, e.g., 1-6 modified nucleotides for each of X and Z independently. Exemplary modified oligonucleotides include, but are not limited to, 2' MOE or 2'OMe or Locked Nucleic Acid bases (LNA). The flanks X and Z may be have a of length 1-20 nucleotides independently for each of X and Z, preferably 1-8 nucleotides independently for each of X and Z and even more preferred 1-5 nucleotides independently for each of X and Z. The flanks X and Z may be of similar length or of dissimilar lengths. The gap-segment Y may be a nucleotide sequence of length 5-20 nucleotides, preferably 6-12 nucleotides and even more preferred 6-10 nucleotides. In some aspects, the gap region of the gapmer oligonucleotides of the invention may contain modified nucleotides known to be acceptable for efficient RNase H action in addition to DNA nucleotides, such as C4'-substituted nucleotides, acyclic nucleotides, and arabino-configured nucleotides. In some embodiments, the gap region comprises one or more unmodified internucleosides. In some embodiments, one or both flanking regions each independently comprise one or more phosphorothioate internucleoside linkages (e.g., phosphorothioate internucleoside linkages or other linkages) between at least two, at least three, at least four, at least five or more nucleotides. In some embodiments, the gap region and two flanking regions each independently comprise modified internucleoside linkages (e.g., phosphorothioate internucleoside linkages or other linkages) between at least two, at least three, at least four, at least five or more nucleotides.

A gapmer may be produced using any method known in the art or described herein. Representative U.S. patents, U.S. patent publications, and PCT publications that teach the preparation of gapmers include, but are not limited to, U.S. Pat. Nos. 5,013,830; 5,149,797; 5,220,007; 5,256,775; 5,366,878; 5,403,711; 5,491,133; 5,565,350; 5,623,065; 5,652,355; 5,652,356; 5,700,922; 5,898,031; 7,432,250; and 7,683,036; U.S. patent publication Nos. US20090286969, US20100197762, and US20110112170; and PCT publication Nos. WO2008049085 and WO2009090182, each of which is herein incorporated by reference in its entirety.

In some embodiments, oligonucleotides having different functions are linked together. For example, in some embodiments, a protecting (e.g., mixmer) oligonucleotide or region described herein is covalently linked to a cleavage promoting (e.g., gapmer) oligonucleotide or region as described herein. The covalent linkage may be a single internucleotide linkage as described herein (e.g., a phosphorothioate internucleotide linkage) or a series of nucleotides (e.g., one or more modified or unmodified nucleotides described herein, with modified or unmodified internucleotide linkages). It is to be understood that oligonucleotides (e.g., a protecting oligonucleotide (e.g., mixmer) and cleavage promoting oligonucleotide (e.g., gapmer)) may be linked in any orientation to one another, e.g., the protecting oligonucleotide may be 5' to the cleavage promoting oligonucleotide or the cleavage promoting oligonucleotide may be 5' to the protecting oligonucleotide. The orientation may depend, in part, upon the region of a target RNA to be cleaved and the adjacent region to be protected from exonucleases.

In some embodiments, a composition is provided comprising a protecting oligonucleotide (e.g., mixmer) and a cleavage promoting oligonucleotide (e.g., gapmer). In some embodiments, such oligonucleotides can be combined in various ratios depending on oligonucleotide efficacy, in vivo distribution and other factors. In some embodiments, the protecting oligonucleotide is present in a ratio of 10000:1, 5000:1, 1000:1, 500:1, 100:1, 10:1, 5:1, or 2:1 to the cleavage promoting oligonucleotide. In some embodiments, the cleavage promoting oligonucleotide is present in a ratio of 10000:1, 5000:1, 1000:1, 500:1, 100:1, 10:1, 5:1, or 2:1 to the protecting oligonucleotide. In some embodiments, a protecting oligonucleotide (e.g., mixmer) is administered to a cell prior to administration of a cleavage promoting oligonucleotide. In some embodiments, the protecting oligonucleotide (e.g., mixmer) is administered in an amount that is 10000 times, 5000 times, 1000 times, 500 times, 100 times, 10 times, 5 times, or 2 times the amount of the cleavage promoting oligonucleotide that is subsequently administered. In some embodiments, the cleavage promoting oligonucleotide is administered in an amount that is 10000 times, 5000 times, 1000 times, 500 times, 100 times, 10 times, 5 times, or 2 times the amount of the protecting oligonucleotide that is administered.

In some embodiments, a gapmer oligonucleotide or gapmer region of an oligonucleotide provided herein is complementary to a region of a target RNA. In some embodiments, a mixmer oligonucleotide or mixmer region of an oligonucleotide provided herein is complementary to a region adjacent to the region of complementarity of the gapmer oligonucleotide or gapmer region. In some embodiments, a gapmer is flanked on both sides by mixmers which may or may not be covalently linked to the gapmer.

In some embodiments, the region of complementarity of a cleaving promoting oligonucleotide or region is complementary with at least 5 to 15, 8 to 15, 8 to 30, 8 to 40, or 10 to 50, or 5 to 50, or 5 to 40 bases, e.g., 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 consecutive nucleotides of a target RNA described herein. In some embodiments, the region of complementarity is complementary with at least 5 or at least 8 consecutive nucleotides of a target RNA described herein. In some embodiments, oligonucleotide comprises a region of complementarity that hybridizes with an RNA transcript, or a portion thereof, said portion having a length of about 5 to 40, or about 8 to 40, or about 5 to 15, or about 5 to 30, or about 5 to 40, or about 5 to 50 contiguous nucleotides.

In some embodiments, the region of complementarity of a cleavage protecting oligonucleotide or region is complementary with at least 5 to 15, 8 to 15, 8 to 30, 8 to 40, or 10 to 50, or 5 to 50, or 5 to 40 bases, e.g., 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 consecutive nucleotides of a region adjacent to the region of complementarity of the cleavage promoting oligonucleotide or region. As used herein, "adjacent to" includes the instance of no nucleotides separating the two regions of complementarity in a target nucleic acid, and the instance of up to 1000 nucleotides (e.g., no more than 500 nucleotides, no more than 400 nucleotides, no more than 300 nucleotides, no more than 200 nucleotides, no more than 100 nucleotides, no more than 50 nucleotides, no more than 40 nucleotides, no more than 30 nucleotides, no more than 20 nucleotides, no more than 10 nucleotides, no more than 5 nucleotides, no more than 4 nucleotides, no more than 3 nucleotides, no more than 2 nucleotides, or no more than 1 nucleotide) separating two regions of complementarity in a target nucleic acid.

Complementary, as the term is used in the art, refers to the capacity for precise pairing between two nucleotides. For example, if a nucleotide at a certain position of an oligonucleotide is capable of hydrogen bonding with a nucleotide at the same position of a target nucleic acid (e.g., an RNA transcript, DNA strand), then the oligonucleotide and the target nucleic acid are considered to be complementary to each other at that position. The oligonucleotide and the target nucleic acid are complementary to each other when a sufficient number of corresponding positions in each molecule are occupied by nucleotides that can hydrogen bond with each other through their bases. Thus, "complementary" is a term which is used to indicate a sufficient degree of complementarity or precise pairing such that stable and specific binding occurs between the oligonucleotide and its target nucleic acid. For example, if a base at one position of an oligonucleotide is capable of hydrogen bonding with a base at the corresponding position of a target nucleic acid, then the bases are considered to be complementary to each other at that position. 100% complementarity is not required.

The oligonucleotide or region thereof may be at least 80% complementary to (optionally one of at least 85%, 90%, 91%, 92%, 93%, 94%, 95%, 96%, 97%, 98%, 99% or 100% complementary to) the consecutive nucleotides of a target nucleic acid. In some embodiments the oligonucleotide or region thereof may contain 1, 2 or 3 base mismatches compared to the portion of the consecutive nucleotides of a target nucleic acid. In some embodiments the oligonucleotide or region thereof may have up to 3 mismatches over 15 bases, or up to 2 mismatches over 10 bases.

It is understood in the art that a complementary nucleotide sequence need not be 100% complementary to that of its target nucleic acid to be specifically hybridizable or specific for a target nucleic acid. In some embodiments, a complementary nucleic acid sequence for purposes of the present disclosure is specifically hybridizable or specific for the target nucleic when binding of the sequence to the target nucleic acid (e.g., RNA transcript) results in increased expression of a target gene and there is a sufficient degree of complementarity to avoid non-specific binding of the sequence to non-target sequences under conditions in which avoidance of non-specific binding is desired, e.g., under physiological conditions in the case of in vivo assays or therapeutic treatment, and in the case of in vitro assays, under conditions in which the assays are performed under suitable conditions of stringency.

The target RNA may be any type of RNA known in the art or described herein, including mRNAs, polyA-containing RNAs (coding or noncoding), synthetic RNAs and noncoding RNAs such as long noncoding RNAs, pre-microRNAs, and microRNAs.

In some embodiments, the RNA is an mRNA having a 5' and 3' UTR. In some embodiments, the mRNA has at least one (e.g., one, two, three, four, five, six, seven, eight, nine, ten or more) miRNA binding sites in the 5' and/or 3'UTR. In some embodiments, the 5' UTR is at least 200 nucleotides, 300 nucleotides, 400 nucleotides, 500 nucleotides, 600 nucleotides, 700 nucleotides, 800 nucleotides, 900 nucleotides, 1000 nucleotides, 2000 nucleotides, 3000 nucleotides, 4000 nucleotides, 5000 nucleotides, 6000 nucleotides, 7000 nucleotides, 8000 nucleotides, 9000 nucleotides, or 10000 nucleotides in length. In some embodiments, the 3' UTR is at least 200 nucleotides, 300 nucleotides, 400 nucleotides, 500 nucleotides, 600 nucleotides, 700 nucleotides, 800 nucleotides, 900 nucleotides, 1000 nucleotides, 2000 nucleotides, 3000 nucleotides, 4000 nucleotides, 5000 nucleotides, 6000 nucleotides, 7000 nucleotides, 8000 nucleotides, 9000 nucleotides, or 10000 nucleotides in length. In some embodiments the 5' and/or 3' UTR comprise one or more regulatory sequences (e.g., miRNA binding sites or other sequences that regulate, e.g., stability, localization, or translation of the RNA). In some embodiments, the gapmer oligonucleotide or gapmer region is complementary to a sequence within the 5' or 3' UTR of the target mRNA. In some embodiments, the 5' and/or 3' UTR are present in an isoform of the target RNA that is correlated with reduced expression of the target RNA (see, e.g., Miura et al. Widespread and extensive lengthening of 3' UTRs in the mammalian brain. Genome Res. 2013 May; 23(5):812-25; and Barrett et al. Regulation of eukaryotic gene expression by the untranslated gene regions and other non-coding elements. Cellular and Molecular Life Sciences. 2012, 69(21):3613-3634).

In some embodiments, an oligonucleotide described herein comprises a synthetic cap or polyA-tail, e.g., to increase efficiency of translation, RNA half-life and/or function within cells. In some embodiments, the oligonucleotide comprises 2, 3, 4, 5, 6, 7, 8, 9, 10 or more of a repeated nucleotide such as T, A, C, or G. Synthetic caps are known in the art. Exemplary synthetic caps include, but are not limited to, N7-Methyl-Guanosine-5'-Triphosphate-5'-Guanosine, Guanosine-5'-Triphosphate-5'-Guanosine, N7-Methyl-3'-O-Methyl-Guanosine-5'-Triphosphate-5'-Guanosine (see, e.g., products available from TrilinkBiotech), and N7-benzylated dinucleoside tetraphosphate analogs (see, e.g., Grudzien et al. Novel cap analogs for in vitro synthesis of mRNAs with high translational efficiency. RNA. 2004 September; 10(9): 1479-1487).

In some embodiments, the target RNA is an mRNA expressed by a target gene described herein. Exemplary target genes and RNAs (such as mRNAs) of target genes are provided in Table 1. In some embodiments, the target gene may be a target gene listed in Table 1, such as ABCA1, APOA1, ATP2A2, BDNF, FXN, HBA2, HBB, HBD, HBE1, HBG1, HBG2, SMN, UTRN, PTEN, MECP2, FOXP3, NFE2L2 (NRF2), THRB, NR1H4 (FXR), HAMP, ADIPOQ, PRKAA1, PRKAA2, PRKAB1, PRKAB2, PRKAG1, PRKAG2, or PRKAG3. In some embodiments, the gapmer oligonucleotide or gapmer region is complementary to a sequence within the 5' or 3' UTR of an mRNA of a target gene provided in Table 1. In some embodiments, the target gene is FXN (e.g., human FXN) and the gapmer oligonucleotide or gapmer region is complementary to a sequence within the 3' UTR of a FXN mRNA (e.g., a human FXN mRNA).

TABLE 1

Non-limiting examples of RNA transcripts for certain genes

| GENE SYMBOL | MRNA | SPECIES | GENE NAME |
|---|---|---|---|
| ABCA1 | NM_013454 | Mus musculus | ATP-binding cassette, sub-family A (ABC1), member 1 |
| ABCA1 | NM_005502 | Homo sapiens | ATP-binding cassette, sub-family A (ABC1), member 1 |
| ABCA4 | NM_007378 | Mus musculus | ATP-binding cassette, sub-family A (ABC1), member 4 |
| ABCA4 | NM_000350 | Homo sapiens | ATP-binding cassette, sub-family A (ABC1), member 4 |
| ABCB11 | NM_003742 | Homo sapiens | ATP-binding cassette, sub-family B (MDR/TAP), member 11 |
| ABCB11 | NM_021022 | Mus musculus | ATP-binding cassette, sub-family B (MDR/TAP), member 11 |
| ABCB4 | NM_018850 | Homo sapiens | ATP-binding cassette, sub-family B (MDR/TAP), member 4 |
| ABCB4 | NM_000443 | Homo sapiens | ATP-binding cassette, sub-family B (MDR/TAP), member 4 |
| ABCB4 | NM_018849 | Homo sapiens | ATP-binding cassette, sub-family B (MDR/TAP), member 4 |
| ABCB4 | NM_008830 | Mus musculus | ATP-binding cassette, sub-family B (MDR/TAP), member 4 |
| ABCG5 | NM_022436 | Homo sapiens | ATP-binding cassette, sub-family G (WHITE), member 5 |
| ABCG5 | NM_031884 | Mus musculus | ATP-binding cassette, sub-family G (WHITE), member 5 |
| ABCG8 | NM_026180 | Mus musculus | ATP-binding cassette, sub-family G (WHITE), member 8 |
| ABCG8 | NM_022437 | Homo sapiens | ATP-binding cassette, sub-family G (WHITE), member 8 |

TABLE 1-continued

Non-limiting examples of RNA transcripts for certain genes

| GENE SYMBOL | MRNA | SPECIES | GENE NAME |
| --- | --- | --- | --- |
| ADIPOQ | NM_009605 | Mus musculus | adiponectin, C1Q and collagen domain containing |
| ADIPOQ | NM_004797 | Homo sapiens | adiponectin, C1Q and collagen domain containing |
| ALB | NM_000477 | Homo sapiens | albumin |
| ALB | NM_009654 | Mus musculus | albumin |
| APOA1 | NM_000039 | Homo sapiens | apolipoprotein A-I |
| APOA1 | NM_009692 | Mus musculus | apolipoprotein A-I |
| APOE | NM_009696 | Mus musculus | apolipoprotein E |
| APOE | XM_001724655 | Homo sapiens | hypothetical LOC100129500; apolipoprotein E |
| APOE | XM_001722911 | Homo sapiens | hypothetical LOC100129500; apolipoprotein E |
| APOE | XM_001724653 | Homo sapiens | hypothetical LOC100129500; apolipoprotein E |
| APOE | NM_000041 | Homo sapiens | hypothetical LOC100129500; apolipoprotein E |
| APOE | XM_001722946 | Homo sapiens | hypothetical LOC100129500; apolipoprotein E |
| ATP2A2 | NM_009722 | Mus musculus | ATPase, Ca++ transporting, cardiac muscle, slow twitch 2 |
| ATP2A2 | NM_001110140 | Mus musculus | ATPase, Ca++ transporting, cardiac muscle, slow twitch 2 |
| ATP2A2 | NM_001135765 | Homo sapiens | ATPase, Ca++ transporting, cardiac muscle, slow twitch 2 |
| ATP2A2 | NM_170665 | Homo sapiens | ATPase, Ca++ transporting, cardiac muscle, slow twitch 2 |
| ATP2A2 | NM_001681 | Homo sapiens | ATPase, Ca++ transporting, cardiac muscle, slow twitch 2 |
| BCL2L11 | NM_006538 | Homo sapiens | BCL2-like 11 (apoptosis facilitator) |
| BCL2L11 | NM_207002 | Homo sapiens | BCL2-like 11 (apoptosis facilitator) |
| BCL2L11 | NM_138621 | Homo sapiens | BCL2-like 11 (apoptosis facilitator) |
| BCL2L11 | NM_207680 | Mus musculus | BCL2-like 11 (apoptosis facilitator) |
| BCL2L11 | NM_207681 | Mus musculus | BCL2-like 11 (apoptosis facilitator) |
| BCL2L11 | NM_009754 | Mus musculus | BCL2-like 11 (apoptosis facilitator) |
| BDNF | NM_001143816 | Homo sapiens | brain-derived neurotrophic factor |
| BDNF | NM_001143815 | Homo sapiens | brain-derived neurotrophic factor |
| BDNF | NM_001143814 | Homo sapiens | brain-derived neurotrophic factor |
| BDNF | NM_001143813 | Homo sapiens | brain-derived neurotrophic factor |
| BDNF | NM_001143812 | Homo sapiens | brain-derived neurotrophic factor |
| BDNF | NM_001143806 | Homo sapiens | brain-derived neurotrophic factor |
| BDNF | NM_001143811 | Homo sapiens | brain-derived neurotrophic factor |
| BDNF | NM_001143805 | Homo sapiens | brain-derived neurotrophic factor |
| BDNF | NM_001143810 | Homo sapiens | brain-derived neurotrophic factor |
| BDNF | NM_001709 | Homo sapiens | brain-derived neurotrophic factor |
| BDNF | NM_170735 | Homo sapiens | brain-derived neurotrophic factor |
| BDNF | NM_170734 | Homo sapiens | brain-derived neurotrophic factor |
| BDNF | NM_170733 | Homo sapiens | brain-derived neurotrophic factor |
| BDNF | NM_170732 | Homo sapiens | brain-derived neurotrophic factor |

TABLE 1-continued

Non-limiting examples of RNA transcripts for certain genes

| GENE SYMBOL | MRNA | SPECIES | GENE NAME |
|---|---|---|---|
| BDNF | NM_170731 | *Homo sapiens* | brain-derived neurotrophic factor |
| BDNF | NM_001143809 | *Homo sapiens* | brain-derived neurotrophic factor |
| BDNF | NM_001143807 | *Homo sapiens* | brain-derived neurotrophic factor |
| BDNF | NM_001143808 | *Homo sapiens* | brain-derived neurotrophic factor |
| BDNF | NM_007540 | *Mus musculus* | brain derived neurotrophic factor |
| BDNF | NM_001048141 | *Mus musculus* | brain derived neurotrophic factor |
| BDNF | NM_001048142 | *Mus musculus* | brain derived neurotrophic factor |
| BDNF | NM_001048139 | *Mus musculus* | brain derived neurotrophic factor |
| BRCA1 | NM_009764 | *Mus musculus* | breast cancer 1 |
| BRCA1 | NM_007296 | *Homo sapiens* | breast cancer 1, early onset |
| BRCA1 | NM_007300 | *Homo sapiens* | breast cancer 1, early onset |
| BRCA1 | NM_007297 | *Homo sapiens* | breast cancer 1, early onset |
| BRCA1 | NM_007303 | *Homo sapiens* | breast cancer 1, early onset |
| BRCA1 | NM_007298 | *Homo sapiens* | breast cancer 1, early onset |
| BRCA1 | NM_007302 | *Homo sapiens* | breast cancer 1, early onset |
| BRCA1 | NM_007299 | *Homo sapiens* | breast cancer 1, early onset |
| BRCA1 | NM_007304 | *Homo sapiens* | breast cancer 1, early onset |
| BRCA1 | NM_007294 | *Homo sapiens* | breast cancer 1, early onset |
| BRCA1 | NM_007305 | *Homo sapiens* | breast cancer 1, early onset |
| BRCA1 | NM_007295 | *Homo sapiens* | breast cancer 1, early onset |
| CD274 | NM_014143 | *Homo sapiens* | CD274 molecule |
| CD274 | NM_021893 | *Mus musculus* | CD274 antigen |
| CEP290 | NM_025114 | *Homo sapiens* | centrosomal protein 290 kDa |
| CEP290 | NM_146009 | *Mus musculus* | centrosomal protein 290 |
| CFTR | NM_000492 | *Homo sapiens* | cystic fibrosis transmembrane conductance regulator (ATP-binding cassette sub-family C, member 7) |
| CFTR | NM_021050 | *Mus musculus* | cystic fibrosis transmembrane conductance regulator homolog |
| EPO | NM_000799 | *Homo sapiens* | erythropoietin |
| EPO | NM_007942 | *Mus musculus* | erythropoietin |
| F7 | NM_000131 | *Homo sapiens* | coagulation factor VII (serum prothrombin conversion accelerator) |
| F7 | NM_019616 | *Homo sapiens* | coagulation factor VII (serum prothrombin conversion accelerator) |
| F7 | NM_010172 | *Mus musculus* | coagulation factor VII |
| F8 | NM_019863 | *Homo sapiens* | coagulation factor VIII, procoagulant component |
| F8 | NM_000132 | *Homo sapiens* | coagulation factor VIII, procoagulant component |
| F8 | NM_001161373 | *Mus musculus* | coagulation factor VIII |
| F8 | NM_001161374 | *Mus musculus* | coagulation factor VIII |
| F8 | NM_007977 | *Mus musculus* | coagulation factor VIII |
| FLI1 | NM_002017 | *Homo sapiens* | Friend leukemia virus integration 1 |

TABLE 1-continued

Non-limiting examples of RNA transcripts for certain genes

| GENE SYMBOL | MRNA | SPECIES | GENE NAME |
|---|---|---|---|
| FLI1 | NM_001167681 | Homo sapiens | Friend leukemia virus integration 1 |
| FLI1 | NM_008026 | Mus musculus | Friend leukemia integration 1 |
| FMR1 | NM_008031 | Mus musculus | fragile X mental retardation syndrome 1 homolog |
| FMR1 | NM_002024 | Homo sapiens | fragile X mental retardation 1 |
| FNDC5 | NM_001171941 | Homo sapiens | fibronectin type III domain containing 5 |
| FNDC5 | NM_153756 | Homo sapiens | fibronectin type III domain containing 5 |
| FNDC5 | NM_001171940 | Homo sapiens | fibronectin type III domain containing 5 |
| FNDC5 | NM_027402 | Mus musculus | fibronectin type III domain containing 5 |
| FOXP3 | NM_054039 | Mus musculus | forkhead box P3 |
| FOXP3 | NM_001114377 | Homo sapiens | forkhead box P3 |
| FOXP3 | NM_014009 | Homo sapiens | forkhead box P3 |
| FXN | NM_001161706 | Homo sapiens | frataxin |
| FXN | NM_181425 | Homo sapiens | frataxin |
| FXN | NM_000144 | Homo sapiens | frataxin |
| FXN | NM_008044 | Mus musculus | frataxin |
| GCH1 | NM_008102 | Mus musculus | GTP cyclohydrolase 1 |
| GCH1 | NM_000161 | Homo sapiens | GTP cyclohydrolase 1 |
| GCH1 | NM_001024070 | Homo sapiens | GTP cyclohydrolase 1 |
| GCH1 | NM_001024071 | Homo sapiens | GTP cyclohydrolase 1 |
| GCH1 | NM_001024024 | Homo sapiens | GTP cyclohydrolase 1 |
| GCK | NM_010292 | Mus musculus | glucokinase |
| GCK | NM_000162 | Homo sapiens | glucokinase (hexokinase 4) |
| GCK | NM_033508 | Homo sapiens | glucokinase (hexokinase 4) |
| GCK | NM_033507 | Homo sapiens | glucokinase (hexokinase 4) |
| GLP1R | NM_021332 | Mus musculus | glucagon-like peptide 1 receptor; similar to glucagon-like peptide-1 receptor |
| GLP1R | XM_001471951 | Mus musculus | glucagon-like peptide 1 receptor; similar to glucagon-like peptide-1 receptor |
| GLP1R | NM_002062 | Homo sapiens | glucagon-like peptide 1 receptor |
| GRN | NM_002087 | Homo sapiens | granulin |
| GRN | NM_008175 | Mus musculus | granulin |
| HAMP | NM_021175 | Homo sapiens | hepcidin antimicrobial peptide |
| HAMP | NM_032541 | Mus musculus | hepcidin antimicrobial peptide |
| HBA2 | NM_000517 | Homo sapiens | hemoglobin, alpha 2; hemoglobin, alpha 1 |
| HBA2 | NM_000558 | Homo sapiens | hemoglobin, alpha 2; hemoglobin, alpha 1 |
| HBB | NM_000518 | Homo sapiens | hemoglobin, beta |
| HBB | XM_921413 | Mus musculus | hemoglobin beta chain complex |
| HBB | XM_903245 | Mus musculus | hemoglobin beta chain complex |
| HBB | XM_921395 | Mus musculus | hemoglobin beta chain complex |

TABLE 1-continued

Non-limiting examples of RNA transcripts for certain genes

| GENE SYMBOL | MRNA | SPECIES | GENE NAME |
|---|---|---|---|
| HBB | XM_903244 | *Mus musculus* | hemoglobin beta chain complex |
| HBB | XM_903246 | *Mus musculus* | hemoglobin beta chain complex |
| HBB | XM_909723 | *Mus musculus* | hemoglobin beta chain complex |
| HBB | XM_921422 | *Mus musculus* | hemoglobin beta chain complex |
| HBB | XM_489729 | *Mus musculus* | hemoglobin beta chain complex |
| HBB | XM_903242 | *Mus musculus* | hemoglobin beta chain complex |
| HBB | XM_903243 | *Mus musculus* | hemoglobin beta chain complex |
| HBB | XM_921400 | *Mus musculus* | hemoglobin beta chain complex |
| HBD | NM_000519 | *Homo sapiens* | hemoglobin, delta |
| HBE1 | NM_005330 | *Homo sapiens* | hemoglobin, epsilon 1 |
| HBG1 | NM_000559 | *Homo sapiens* | hemoglobin, gamma A |
| HBG2 | NM_000184 | *Homo sapiens* | hemoglobin, gamma G |
| HPRT1 | NM_000194 | *Homo sapiens* | hypoxanthine phosphoribosyltransferase 1 |
| IDO1 | NM_008324 | *Mus musculus* | indoleamine 2,3-dioxygenase 1 |
| IDO1 | NM_002164 | *Homo sapiens* | indoleamine 2,3-dioxygenase 1 |
| IGF1 | NM_001111284 | *Homo sapiens* | insulin-like growth factor 1 (somatomedin C) |
| IGF1 | NM_001111285 | *Homo sapiens* | insulin-like growth factor 1 (somatomedin C) |
| IGF1 | NM_001111283 | *Homo sapiens* | insulin-like growth factor 1 (somatomedin C) |
| IGF1 | NM_000618 | *Homo sapiens* | insulin-like growth factor 1 (somatomedin C) |
| IGF1 | NM_001111274 | *Mus musculus* | insulin-like growth factor 1 |
| IGF1 | NM_010512 | *Mus musculus* | insulin-like growth factor 1 |
| IGF1 | NM_184052 | *Mus musculus* | insulin-like growth factor 1 |
| IGF1 | NM_001111276 | *Mus musculus* | insulin-like growth factor 1 |
| IGF1 | NM_001111275 | *Mus musculus* | insulin-like growth factor 1 |
| IL10 | NM_000572 | *Homo sapiens* | interleukin 10 |
| IL10 | NM_010548 | *Mus musculus* | interleukin 10 |
| IL6 | NM_031168 | *Mus musculus* | interleukin 6 |
| IL6 | NM_000600 | *Homo sapiens* | interleukin 6 (interferon, beta 2) |
| KCNMA1 | NM_002247 | *Homo sapiens* | potassium large conductance calcium-activated channel, subfamily M, alpha member 1 |
| KCNMA1 | NM_001161352 | *Homo sapiens* | potassium large conductance calcium-activated channel, subfamily M, alpha member 1 |
| KCNMA1 | NM_001014797 | *Homo sapiens* | potassium large conductance calcium-activated channel, subfamily M, alpha member 1 |
| KCNMA1 | NM_001161353 | *Homo sapiens* | potassium large conductance calcium-activated channel, subfamily M, alpha member 1 |
| KCNMA1 | NM_010610 | *Mus musculus* | potassium large conductance calcium-activated channel, subfamily M, alpha member 1 |
| KCNMB1 | NM_031169 | *Mus musculus* | potassium large conductance calcium-activated channel, subfamily M, beta member 1 |

TABLE 1-continued

Non-limiting examples of RNA transcripts for certain genes

| GENE SYMBOL | MRNA | SPECIES | GENE NAME |
|---|---|---|---|
| KCNMB1 | NM_004137 | *Homo sapiens* | potassium large conductance calcium-activated channel, subfamily M, beta member 1 |
| KCNMB2 | NM_028231 | *Mus musculus* | potassium large conductance calcium-activated channel, subfamily M, beta member 2 |
| KCNMB2 | NM_005832 | *Homo sapiens* | potassium large conductance calcium-activated channel, subfamily M, beta member 2 |
| KCNMB2 | NM_181361 | *Homo sapiens* | potassium large conductance calcium-activated channel, subfamily M, beta member 2 |
| KCNMB3 | NM_171829 | *Homo sapiens* | potassium large conductance calcium-activated channel, subfamily M beta member 3 |
| KCNMB3 | NM_171828 | *Homo sapiens* | potassium large conductance calcium-activated channel, subfamily M beta member 3 |
| KCNMB3 | NM_001163677 | *Homo sapiens* | potassium large conductance calcium-activated channel, subfamily M beta member 3 |
| KCNMB3 | NM_014407 | *Homo sapiens* | potassium large conductance calcium-activated channel, subfamily M beta member 3 |
| KCNMB3 | NM_171830 | *Homo sapiens* | potassium large conductance calcium-activated channel, subfamily M beta member 3 |
| KCNMB3 | XM_001475546 | *Mus musculus* | potassium large conductance calcium-activated channel, subfamily M, beta member 3 |
| KCNMB3 | XM_912348 | *Mus musculus* | potassium large conductance calcium-activated channel, subfamily M, beta member 3 |
| KCNMB4 | NM_021452 | *Mus musculus* | potassium large conductance calcium-activated channel, subfamily M, beta member 4 |
| KCNMB4 | NM_014505 | *Homo sapiens* | potassium large conductance calcium-activated channel, subfamily M, beta member 4 |
| KLF1 | NM_010635 | *Mus musculus* | Kruppel-like factor 1 (erythroid) |
| KLF1 | NM_006563 | *Homo sapiens* | Kruppel-like factor 1 (erythroid) |
| KLF4 | NM_010637 | *Mus musculus* | Kruppel-like factor 4 (gut) |
| KLF4 | NM_004235 | *Homo sapiens* | Kruppel-like factor 4 (gut) |
| LAMA1 | NM_005559.3 | *Homo sapiens* | laminin, alpha 1 |
| LAMA1 | NM_008480.2 | *Mus musculus* | laminin, alpha 1 |
| LDLR | NM_000527 | *Homo sapiens* | low density lipoprotein receptor |
| LDLR | NM_010700 | *Mus musculus* | low density lipoprotein receptor |
| MBNL1 | NM_021038.3, NM_020007.3, NM_207293.1, NM_207294.1, NM_207295.1, NM_207296.1, NM_207297.1 | *Homo sapiens* | muscleblind-like splicing regulator 1 |
| MBNL1 | NM_001253708.1, NM_001253709.1, NM_001253710.1, NM_001253711.1, NM_001253713.1, NM_020007.3 | *Mus musculus* | muscleblind-like 1 (*Drosophila*) |
| MECP2 | NM_010788 | *Mus musculus* | methyl CpG binding protein 2 |
| MECP2 | NM_001081979 | *Mus musculus* | methyl CpG binding protein 2 |

TABLE 1-continued

Non-limiting examples of RNA transcripts for certain genes

| GENE SYMBOL | MRNA | SPECIES | GENE NAME |
| --- | --- | --- | --- |
| MECP2 | NM_001110792 | Homo sapiens | methyl CpG binding protein 2 (Rett syndrome) |
| MECP2 | NM_004992 | Homo sapiens | methyl CpG binding protein 2 (Rett syndrome) |
| MERTK | NM_006343.2 | Homo sapiens | MER proto-oncogene, tyrosine kinase |
| MERTK | NM_008587.1 | Mus musculus | c-mer proto-oncogene tyrosine kinase |
| MSX2 | NM_013601 | Mus musculus | similar to homeobox protein; homeobox, msh-like 2 |
| MSX2 | XM_001475886 | Mus musculus | similar to homeobox protein; homeobox, msh-like 2 |
| MSX2 | NM_002449 | Homo sapiens | msh homeobox 2 |
| MYBPC3 | NM_008653 | Mus musculus | myosin binding protein C, cardiac |
| MYBPC3 | NM_000256 | Homo sapiens | myosin binding protein C, cardiac |
| NANOG | NM_024865 | Homo sapiens | Nanog homeobox pseudogene 8; Nanog homeobox |
| NANOG | XM_001471588 | Mus musculus | similar to Nanog homeobox; Nanog homeobox |
| NANOG | NM_028016 | Mus musculus | similar to Nanog homeobox; Nanog homeobox |
| NANOG | NM_001080945 | Mus musculus | similar to Nanog homeobox; Nanog homeobox |
| NF1 | NM_000267 | Homo sapiens | neurofibromin 1 |
| NF1 | NM_001042492 | Homo sapiens | neurofibromin 1 |
| NF1 | NM_001128147 | Homo sapiens | neurofibromin 1 |
| NF1 | NM_010897 | Mus musculus | neurofibromatosis 1 |
| NKX2-1 | NM_001079668 | Homo sapiens | NK2 homeobox 1 |
| NKX2-1 | NM_003317 | Homo sapiens | NK2 homeobox 1 |
| NKX2-1 | XM_002344771 | Homo sapiens | NK2 homeobox 1 |
| NKX2-1 | NM_009385 | Mus musculus | NK2 homeobox 1 |
| NKX2-1 | NM_001146198 | Mus musculus | NK2 homeobox 1 |
| PAH | NM_008777 | Mus musculus | phenylalanine hydroxylase |
| PAH | NM_000277 | Homo sapiens | phenylalanine hydroxylase |
| PTEN | NM_000314 | Homo sapiens | phosphatase and tensin homolog; phosphatase and tensin homolog pseudogene 1 |
| PTEN | NM_177096 | Mus musculus | phosphatase and tensin homolog |
| PTEN | NM_008960 | Mus musculus | phosphatase and tensin homolog |
| PTGS2 | NM_011198 | Mus musculus | prostaglandin-endoperoxide synthase 2 |
| PTGS2 | NM_000963 | Homo sapiens | prostaglandin-endoperoxide synthase 2 (prostaglandin G/H synthase and cyclooxygenase) |
| RB1 | NM_009029 | Mus musculus | retinoblastoma 1 |
| RB1 | NM_000321 | Homo sapiens | retinoblastoma 1 |
| RPS14 | NM_020600 | Mus musculus | predicted gene 6204; ribosomal protein S14 |
| RPS14 | NM_001025071 | Homo sapiens | ribosomal protein S14 |
| RPS14 | NM_005617 | Homo sapiens | ribosomal protein S14 |
| RPS14 | NM_001025070 | Homo sapiens | ribosomal protein S14 |
| RPS19 | XM_204069 | Mus musculus | predicted gene 4327; predicted gene 8683; similar to 40S ribosomal protein S19; predicted gene 4510; predicted gene 13143; |

TABLE 1-continued

Non-limiting examples of RNA transcripts for certain genes

| GENE SYMBOL | MRNA | SPECIES | GENE NAME |
| --- | --- | --- | --- |
| RPS19 | XM_991053 | Mus musculus | predicted gene 9646; ribosomal protein S19; predicted gene 9091; predicted gene 6636; predicted gene 14072 predicted gene 4327; predicted gene 8683; similar to 40S ribosomal protein S19; predicted gene 4510; predicted gene 13143; predicted gene 9646; ribosomal protein S19; predicted gene 9091; predicted gene 6636; predicted gene 14072 |
| RPS19 | XM_905004 | Mus musculus | predicted gene 4327; predicted gene 8683; similar to 40S ribosomal protein S19; predicted gene 4510; predicted gene 13143; predicted gene 9646; ribosomal protein S19; predicted gene 9091; predicted gene 6636; predicted gene 14072 |
| RPS19 | XM_001005575 | Mus musculus | predicted gene 4327; predicted gene 8683; similar to 40S ribosomal protein S19; predicted gene 4510; predicted gene 13143; predicted gene 9646; ribosomal protein S19; predicted gene 9091; predicted gene 6636; predicted gene 14072 |
| RPS19 | NM_023133 | Mus musculus | predicted gene 4327; predicted gene 8683; similar to 40S ribosomal protein S19; predicted gene 4510; predicted gene 13143; predicted gene 9646; ribosomal protein S19; predicted gene 9091; predicted gene 6636; predicted gene 14072 |
| RPS19 | XM_994263 | Mus musculus | predicted gene 4327; predicted gene 8683; similar to 40S ribosomal protein S19; predicted gene 4510; predicted gene 13143; predicted gene 9646; ribosomal protein S19; predicted gene 9091; predicted gene 6636; predicted gene 14072 |
| RPS19 | XM_001481027 | Mus musculus | predicted gene 4327; predicted gene 8683; similar to 40S ribosomal protein S19; predicted gene 4510; predicted gene 13143; predicted gene 9646; ribosomal protein S19; predicted gene 9091; predicted gene 6636; predicted gene 14072 |
| RPS19 | XM_913504 | Mus musculus | predicted gene 4327; predicted gene 8683; similar to 40S ribosomal protein S19; predicted gene 4510; predicted gene 13143; predicted gene 9646; ribosomal protein S19; predicted gene 9091; predicted gene 6636; predicted gene 14072 |
| RPS19 | XM_001479631 | Mus musculus | predicted gene 4327; predicted gene 8683; similar to 40S ribosomal protein S19; predicted gene 4510; predicted gene 13143; predicted gene 9646; ribosomal protein S19; predicted gene 9091; predicted gene 6636; predicted gene 14072 |
| RPS19 | XM_902221 | Mus musculus | predicted gene 4327; predicted gene 8683; similar to 40S ribosomal protein S19; predicted gene 4510; predicted gene 13143; predicted gene 9646; ribosomal protein S19; predicted gene 9091; predicted gene 6636; predicted gene 14072 |
| RPS19 | XM_893968 | Mus musculus | predicted gene 4327; predicted gene 8683; similar to 40S ribosomal protein S19; predicted gene 4510; predicted gene 13143; predicted gene 9646; ribosomal protein S19; predicted gene 9091; predicted gene 6636; predicted gene 14072 |
| RPS19 | NM_001022 | Homo sapiens | ribosomal protein S19 pseudogene 3; ribosomal protein S19 |
| SCARB1 | NM_016741 | Mus musculus | scavenger receptor class B, member 1 |
| SCARB1 | NM_001082959 | Homo sapiens | scavenger receptor class B, member 1 |
| SCARB1 | NM_005505 | Homo sapiens | scavenger receptor class B, member 1 |
| SERPINF1 | NM_011340 | Mus musculus | serine (or cysteine) peptidase inhibitor, clade F, member 1 |

TABLE 1-continued

Non-limiting examples of RNA transcripts for certain genes

| GENE SYMBOL | MRNA | SPECIES | GENE NAME |
|---|---|---|---|
| SERPINF1 | NM_002615 | Homo sapiens | serpin peptidase inhibitor, clade F (alpha-2 antiplasmin, pigment epithelium derived factor), member 1 |
| SIRT1 | NM_001159590 | Mus musculus | sirtuin 1 (silent mating type information regulation 2, homolog) 1 (S. cerevisiae) |
| SIRT1 | NM_019812 | Mus musculus | sirtuin 1 (silent mating type information regulation 2, homolog) 1 (S. cerevisiae) |
| SIRT1 | NM_001159589 | Mus musculus | sirtuin 1 (silent mating type information regulation 2, homolog) 1 (S. cerevisiae) |
| SIRT1 | NM_012238 | Homo sapiens | sirtuin (silent mating type information regulation 2 homolog) 1 (S. cerevisiae) |
| SIRT1 | NM_001142498 | Homo sapiens | sirtuin (silent mating type information regulation 2 homolog) 1 (S. cerevisiae) |
| SIRT6 | NM_016539 | Homo sapiens | sirtuin (silent mating type information regulation 2 homolog) 6 (S. cerevisiae) |
| SIRT6 | NM_001163430 | Mus musculus | sirtuin 6 (silent mating type information regulation 2, homolog) 6 (S. cerevisiae) |
| SIRT6 | NM_181586 | Mus musculus | sirtuin 6 (silent mating type information regulation 2, homolog) 6 (S. cerevisiae) |
| SMAD7 | NM_005904 | Homo sapiens | SMAD family member 7 |
| SMAD7 | NM_001042660 | Mus musculus | MAD homolog 7 (Drosophila) |
| SMN1 | NM_000344.3 | Homo sapiens | Survival Motor Neuron 1 |
| SMN1 | NM_022874.2 | Homo sapiens | Survival Motor Neuron 1 |
| SMN2 | NM_017411.3 NM_022875.2 NM_022876.2 NM_022877.2 | Homo sapiens | Survival Motor Neuron 2 |
| SSPN | NM_001135823.1, NM_005086.4 | Homo sapiens | sarcospan |
| SSPN | NM_010656.2 | Homo sapiens | sarcospan |
| ST7 | NM_021908 | Homo sapiens | suppression of tumorigenicity 7 |
| ST7 | NM_018412 | Homo sapiens | suppression of tumorigenicity 7 |
| STAT3 | NM_213660 | Mus musculus | similar to Stat3B; signal transducer and activator of transcription 3 |
| STAT3 | XM_001474017 | Mus musculus | similar to Stat3B; signal transducer and activator of transcription 3 |
| STAT3 | NM_213659 | Mus musculus | similar to Stat3B; signal transducer and activator of transcription 3 |
| STAT3 | NM_011486 | Mus musculus | similar to Stat3B; signal transducer and activator of transcription 3 |
| STAT3 | NM_213662 | Homo sapiens | signal transducer and activator of transcription 3 (acute-phase response factor) |
| STAT3 | NM_003150 | Homo sapiens | signal transducer and activator of transcription 3 (acute-phase response factor) |
| STAT3 | NM_139276 | Homo sapiens | signal transducer and activator of transcription 3 (acute-phase response factor) |
| UTRN | NM_007124 | Homo sapiens | utrophin |
| UTRN | NM_011682 | Mus musculus | utrophin |
| NFE2L2 | NM_001145412.2, NM_001145413.2, NM_006164.4 | Homo sapiens | nuclear factor, erythroid 2-like 2 |
| NFE2L2 | NM_010902.3 | Mus musculus | nuclear factor, erythroid 2-like 2 |
| ACTB | NM_001101.3 | Homo sapiens | actin, beta |
| ACTB | NM_007393.3 | Mus musculus | actin, beta |
| ANRIL | NR_003529.3, NR_047532.1, NR_047533.1, NR_047534.1, NR_047535.1, NR_047536.1, NR_047538.1, NR_047539.1, NR_047540.1, | Homo sapiens | CDKN2B antisense RNA 1 (also called CDKN2B) |

TABLE 1-continued

Non-limiting examples of RNA transcripts for certain genes

| GENE SYMBOL | MRNA | SPECIES | GENE NAME |
|---|---|---|---|
| | NR_047541.1, NR_047542.1, NR_047543.1 | | |
| HOTAIR | NR_003716.3, NR_047517.1, NR_047518.1 | Homo sapiens | HOX transcript antisense RNA |
| HOTAIR | NR_047528.1 | Mus musculus | HOX transcript antisense RNA |
| DINO | JX993265 | Homo sapiens | Damage Induced NOncoding |
| DINO | JX993266 | Mus musculus | Damage Induced NOncoding |
| HOTTIP | NR_037843.3 | Homo sapiens | HOXA distal transcript antisense RNA |
| HOTTIP | NR_110441.1, NR_110442.1 | Mus musculus | Hoxa distal transcript antisense RNA |
| NEST | NR_104124.1 | Homo sapiens | Homo sapiens IFNG antisense RNA 1 (IFNG-AS1), transcript variant 1, long non-coding RNA. |
| NEST | NR_104123.1 | Mus musculus | Theiler's murine encephalomyelitis virus persistence candidate gene 1 |
| THRB | NM_000461.4 | Homo sapiens | thyroid hormone receptor, beta |
| THRB | NM_001128176.2 | Homo sapiens | thyroid hormone receptor, beta |
| THRB | NM_001128177.1 | Homo sapiens | thyroid hormone receptor, beta |
| THRB | NM_001252634.1 | Homo sapiens | thyroid hormone receptor, beta |
| THRB | NM_001113417.1 | Mus musculus | thyroid hormone receptor, beta |
| THRB | NM_009380.3 | Mus musculus | thyroid hormone receptor, beta |
| NR1H4 | NM_001206977.1 | Homo sapiens | nuclear receptor subfamily 1, group H, member 4 |
| NR1H4 | NM_001206978.1 | Homo sapiens | nuclear receptor subfamily 1, group H, member 4 |
| NR1H4 | NM_001206979.1 | Homo sapiens | nuclear receptor subfamily 1, group H, member 4 |
| NR1H4 | NM_001206992.1 | Homo sapiens | nuclear receptor subfamily 1, group H, member 4 |
| NR1H4 | NM_001206993.1 | Homo sapiens | nuclear receptor subfamily 1, group H, member 4 |
| NR1H4 | NM_005123.3 | Homo sapiens | nuclear receptor subfamily 1, group H, member 4 |
| NR1H4 | NM_001163504.1 | Mus musculus | nuclear receptor subfamily 1, group H, member 4 |
| NR1H4 | NM_001163700.1 | Mus musculus | nuclear receptor subfamily 1, group H, member 4 |
| NR1H4 | NM_009108.2 | Mus musculus | nuclear receptor subfamily 1, group H, member 4 |
| PRKAA1 | NM_006251.5 | Homo sapiens | protein kinase, AMP-activated, alpha 1 catalytic subunit |
| PRKAA1 | NM_206907.3 | Homo sapiens | protein kinase, AMP-activated, alpha 1 catalytic subunit |
| PRKAA1 | NM_001013367.3 | Mus musculus | protein kinase, AMP-activated, alpha 1 catalytic subunit |
| PRKAA2 | NM_006252.3 | Homo sapiens | protein kinase, AMP-activated, alpha 2 catalytic subunit |
| PRKAA2 | NM_178143.2 | Mus musculus | protein kinase, AMP-activated, alpha 2 catalytic subunit |
| PRKAB1 | NM_006253.4 | Homo sapiens | protein kinase, AMP-activated, beta 1 non-catalytic subunit |
| PRKAB1 | NM_031869.2 | Mus musculus | protein kinase, AMP-activated, beta 1 non-catalytic subunit |
| PRKAB2 | NM_005399.4 | Homo sapiens | protein kinase, AMP-activated, beta 2 non-catalytic subunit |
| PRKAB2 | NM_182997.2 | Mus musculus | protein kinase, AMP-activated, beta 2 non-catalytic subunit |
| PRKAG1 | NM_001206709.1 | Homo sapiens | protein kinase, AMP-activated, gamma 1 non-catalytic subunit |
| PRKAG1 | NM_001206710.1 | Homo sapiens | protein kinase, AMP-activated, gamma 1 non-catalytic subunit |
| PRKAG1 | NM_002733.4 | Homo sapiens | protein kinase, AMP-activated, gamma 1 non-catalytic subunit |

TABLE 1-continued

Non-limiting examples of RNA transcripts for certain genes

| GENE SYMBOL | MRNA | SPECIES | GENE NAME |
|---|---|---|---|
| PRKAG1 | NM_016781.2 | *Mus musculus* | protein kinase, AMP-activated, gamma 1 non-catalytic subunit |
| PRKAG2 | NM_001040633.1 | *Homo sapiens* | protein kinase, AMP-activated, gamma 2 non-catalytic subunit |
| PRKAG2 | NM_001304527.1 | *Homo sapiens* | protein kinase, AMP-activated, gamma 2 non-catalytic subunit |
| PRKAG2 | NM_001304531.1 | *Homo sapiens* | protein kinase, AMP-activated, gamma 2 non-catalytic subunit |
| PRKAG2 | NM_016203.3 | *Homo sapiens* | protein kinase, AMP-activated, gamma 2 non-catalytic subunit |
| PRKAG2 | NM_024429.1 | *Homo sapiens* | protein kinase, AMP-activated, gamma 2 non-catalytic subunit |
| PRKAG2 | NM_001170555.1 | *Mus musculus* | protein kinase, AMP-activated, gamma 2 non-catalytic subunit |
| PRKAG2 | NM_001170556.1 | *Mus musculus* | protein kinase, AMP-activated, gamma 2 non-catalytic subunit |
| PRKAG2 | NM_145401.2 | *Mus musculus* | protein kinase, AMP-activated, gamma 2 non-catalytic subunit |
| PRKAG3 | NM_017431.2 | *Homo sapiens* | protein kinase, AMP-activated, gamma 3 non-catalytic subunit |
| PRKAG3 | NM_153744.3 | *Mus musculus* | protein kinase, AMP-activated, gamma 3 non-catalytic subunit |

In some embodiments, a target RNA comprises a triplet repeat region or other repeat sequences (e.g., Alu Repeats, mammalian-wide interspersed repeats, LINEs, SINEs, etc.). In some embodiments, the triplet repeat is selected from the group consisting of GAA, CTG, CGG, and CCG. In some embodiments, the length of the repeat is 10 to 50 repeats, 25 to 100 repeats, 50 to 150 repeats, 100 to 500 repeats, 100 to 1000 repeats or more. In some embodiments, the length of the repeat is at least 10, at least 25, at least 50, at least 100, at least 150, at least 250, at least 500 or more.

Oligonucleotides disclosed herein may target the repeat region or a sequence occurring at a position adjacent to the repeat region, e.g., in order to cleave the repeat region away from the rest of the target RNA. In some embodiments, if the repeat region is within the 5' portion of target RNA (e.g., the 5' UTR), then the cleavage promoting oligonucleotide or region is complementary to a region within 10, 20, 30, 40, 50, 100, 200, 300, 400, 500 or 1000 nucleotides from the 3' end of the repeat region and the protecting oligonucleotide or region is complementary to a region that is 3' of the region complementary to the cleavage promoting oligonucleotide or region. In some embodiments, if the repeat region is within the 3' portion of target RNA (e.g., the 3' UTR), then the cleavage promoting oligonucleotide or region is complementary to a region within 10, 20, 30, 40, 50, 100, 200, 300, 400, 500 or 1000 nucleotides from the 5' end of the repeat region and the protecting oligonucleotide or region is complementary to a region that is 5' of the region complementary to the cleavage promoting oligonucleotide or region. In some embodiments, oligonucleotides may have a cleavage promoting portion (e.g., a gapmer) targeting a repeat region and a protecting portion (e.g., a mixmer) targeting an adjacent non-repeat region. Such oligonucleotides may also be particularly advantageous where the repeat region occurs elsewhere within the genome of a cell harboring the gene.

In some embodiments, an oligonucleotide comprises a sequence represented by the formula $(X_1X_2X_3)_n$, in which X is any nucleotide, and in which n is 4-20. In some embodiments, an oligonucleotide comprises a sequence represented by the formula $(X_1X_2X_3X_4)_n$, in which X is any nucleotide, and in which n is 4-20. In some embodiments, $X_1X_2X_3X_4$ is CCCC or GGGG. In some embodiments, an oligonucleotide comprises a sequence represented by the formula $(X_1X_2X_3X_4X_5)_n$, in which X is any nucleotide, and in which n is 4-20. In some embodiments, $X_1X_2X_3X_4X_5$ is ATTCT or AGAAT. In some embodiments, the oligonucleotide includes non-repeat sequences on one or both sides of the repeat sequence that are complementary to sequences adjacent to the repeat region in its genomic context.

Any RNA containing repeat regions may be targeted using the oligonucleotides and methods disclosed herein. In some embodiments, the target gene is selected from the group consisting of: DMPL, FMR1, AFF2/FMR3, and DIP2B. Further information regarding these genes and their associated diseases is provided in Table 2 below.

TABLE 2

Repeat expansion genes and related diseases

| Disorder | Affected Gene | Repeat | Repeat Location | Normal Repeat No. | Symptomatic Repeat No. | OMIM No. |
|---|---|---|---|---|---|---|
| Myotonic dystrophy type 1 | DMPL | CTG | 3' UTR | 5-37 | >50->2000 | 160900 |
| Fragile X syndrome | FMR1 | CGG | 5' UTR | 6-52 | ~55->2000 | 309550 |
| (FRAXE) Mental Retardation | AFF2/FMR3 | CCG | 5' end | 6-25 | >200 | 309548 |

TABLE 2-continued

Repeat expansion genes and related diseases

| Disorder | Affected Gene | Repeat | Repeat Location | Normal Repeat No. | Symptomatic Repeat No. | OMIM No. |
|---|---|---|---|---|---|---|
| (FRA12A) Mental Retardation | DIP2B | CGG | 5' UTR | 6-23 | | 136630 |

Oligonucleotides or regions thereof may also comprise any one or more of the following characteristics.

Oligonucleotides or regions thereof provided herein may have a sequence that does not contain guanosine nucleotide stretches (e.g., 3 or more, 4 or more, 5 or more, 6 or more consecutive guanosine nucleotides). In some embodiments, oligonucleotides having guanosine nucleotide stretches may have increased non-specific binding and/or off-target effects, compared with oligonucleotides that do not have guanosine nucleotide stretches.

Oligonucleotides or regions thereof provided herein may have a sequence that has less than a threshold level of sequence identity with every sequence of nucleotides, of equivalent length, that map to a genomic position encompassing or in proximity to an off-target gene. For example, an oligonucleotide may be designed to ensure that it does not have a sequence that maps to genomic positions encompassing or in proximity with all known genes (e.g., all known protein coding genes) other than a target gene. The threshold level of sequence identity may be 50%, 60%, 70%, 80%, 85%, 90%, 95%, 99% or 100% sequence identity.

Oligonucleotides or regions thereof provided herein may have a sequence that is has greater than 30% G-C content, greater than 40% G-C content, greater than 50% G-C content, greater than 60% G-C content, greater than 70% G-C content, or greater than 80% G-C content. The oligonucleotide may have a sequence that has up to 100% G-C content, up to 95% G-C content, up to 90% G-C content, or up to 80% G-C content. In some embodiments in which the oligonucleotide is 8 to 10 nucleotides in length, all but 1, 2, 3, 4, or 5 of the nucleotides are cytosine or guanosine nucleotides. In some embodiments, the sequence of the mRNA to which the oligonucleotide is complementary comprises no more than 3 nucleotides selected from adenine and uracil.

Oligonucleotides or regions thereof provided herein may be complementary to a target RNA of multiple different species (e.g., human, mouse, rat, rabbit, goat, monkey, etc.). Oligonucleotides having these characteristics may be tested in vivo or in vitro for efficacy in multiple species (e.g., human and mouse). This approach also facilitates development of clinical candidates for treating human disease by selecting a species in which an appropriate animal exists for the disease.

In some embodiments, the oligonucleotide is 7, 8, 9, 10, 11, 12, 13, 14, 15, 16, 17, 18, 19, 20, 21, 22, 23, 24, 25, 26, 27, 28, 29, 30, 35, 40, 45, 50 or more nucleotides in length. In a preferred embodiment, the oligonucleotide is 8 to 30 nucleotides in length.

Base pairings may include both canonical Watson-Crick base pairing and non-Watson-Crick base pairing (e.g., Wobble base pairing and Hoogsteen base pairing). It is understood that for complementary base pairings, adenosine-type bases (A) are complementary to thymidine-type bases (T) or uracil-type bases (U), that cytosine-type bases (C) are complementary to guanosine-type bases (G), and that universal bases such as 3-nitropyrrole or 5-nitroindole can hybridize to and are considered complementary to any A, C, U, or T. Inosine (I) has also been considered in the art to be a universal base and is considered complementary to any A, C, U or T.

In some embodiments, any one or more thymidine (T) nucleotides (or modified nucleotide thereof) or uridine (U) nucleotides (or a modified nucleotide thereof) in a sequence provided herein, including a sequence provided in the sequence listing, may be replaced with any other nucleotide suitable for base pairing (e.g., via a Watson-Crick base pair) with an adenosine nucleotide. In some embodiments, any one or more thymidine (T) nucleotides (or modified nucleotide thereof) or uridine (U) nucleotides (or a modified nucleotide thereof) in a sequence provided herein, including a sequence provided in the sequence listing, may be suitably replaced with a different pyrimidine nucleotide or vice versa. In some embodiments, any one or more thymidine (T) nucleotides (or modified nucleotide thereof) in a sequence provided herein, including a sequence provided in the sequence listing, may be suitably replaced with a uridine (U) nucleotide (or a modified nucleotide thereof) or vice versa.

In some embodiments, GC content of the oligonucleotide or region thereof is preferably between about 30-60%. Contiguous runs of three or more Gs or Cs may not be preferable in some embodiments. Accordingly, in some embodiments, the oligonucleotide or region thereof does not comprise a stretch of three or more guanosine nucleotides.

It is to be understood that any oligonucleotide provided herein can be excluded.

In some embodiments, it has been found that oligonucleotides disclosed herein may increase expression of a target gene (e.g., FXN) by at least about 50% (i.e. 150% of normal or 1.5 fold), or by about 2 fold to about 5 fold. In some embodiments, expression may be increased by at least about 15 fold, 20 fold, 30 fold, 40 fold, 50 fold or 100 fold, or any range between any of the foregoing numbers.

The oligonucleotides or regions thereof described herein may be modified, e.g., comprise a modified sugar moiety, a modified internucleoside linkage, a modified nucleotide and/or combinations thereof. In addition, the oligonucleotides or regions thereof may exhibit one or more of the following properties: are not immune stimulatory; are nuclease resistant; have improved cell uptake compared to unmodified oligonucleotides; are not toxic to cells or mammals; or have improved endosomal exit.

Any of the oligonucleotides or regions thereof disclosed herein may be linked to one or more other oligonucleotides disclosed herein by a linker, e.g., a cleavable linker.

Oligonucleotides or regions thereof of the invention can be stabilized against nucleolytic degradation such as by the incorporation of a modification, e.g., a nucleotide modification. For example, nucleic acid sequences of the invention may include a phosphorothioate at least the first, second, or third internucleoside linkage at the 5' or 3' end of the nucleotide sequence. As another example, the nucleic acid sequence can include a 2'-modified nucleotide, e.g., a 2'-deoxy, 2'-deoxy-2'-fluoro, 2'-O-methyl, 2'-O-methoxyethyl (2'-O-MOE), 2'-O-aminopropyl (2'-O-AP), 2'-O-dimethylaminoethyl (2'-O-DMAOE), 2'-O-dimethylaminopropyl (2'-O-DMAP), 2'-O-dimethylaminoethyloxyethyl (2'-O-DMAEOE), or 2'-O—N-methylacetamido (2'-O-NMA). As another example, the nucleic acid sequence can include at least one 2'-O-methyl-modified nucleotide, and in some embodiments, all of the nucleotides include a 2'-O-methyl modification. In some embodiments, the nucleic acids are "locked," i.e., comprise nucleic acid analogues in which the ribose ring is "locked" by a methylene bridge connecting the 2'-O atom and the 4'-C atom.

Any of the modified chemistries or formats of oligonucleotides or regions thereof described herein can be combined with each other, and that one, two, three, four, five, or more different types of modifications can be included within the same molecule.

In some embodiments, an oligonucleotide may comprise one or more modified nucleotides (also referred to herein as nucleotide analogs). In some embodiments, the oligonucleotide may comprise at least one ribonucleotide, at least one deoxyribonucleotide, and/or at least one bridged nucleotide. In some embodiments, the oligonucleotide may comprise a bridged nucleotide, such as a locked nucleic acid (LNA) nucleotide, a constrained ethyl (cEt) nucleotide, or an ethylene bridged nucleic acid (ENA) nucleotide. Examples of such nucleotides are disclosed herein and known in the art. In some embodiments, the oligonucleotide comprises a nucleotide analog disclosed in one of the following United States Patent or Patent Application Publications: U.S. Pat. Nos. 7,399,845, 7,741,457, 8,022,193, 7,569,686, 7,335,765, 7,314,923, 7,335,765, and 7,816,333, US 20110009471, the entire contents of each of which are incorporated herein by reference for all purposes. The oligonucleotide may have one or more 2' O-methyl nucleotides.

Often the oligonucleotide has one or more nucleotide analogues. For example, the oligonucleotide may have at least one nucleotide analogue that results in an increase in $T_m$ of the oligonucleotide in a range of 1° C., 2° C., 3° C., 4° C., or 5° C. compared with an oligonucleotide that does not have the at least one nucleotide analogue. The oligonucleotide may have a plurality of nucleotide analogues that results in a total increase in $T_m$ of the oligonucleotide in a range of 2° C., 3° C., 4° C., 5° C., 6° C., 7° C., 8° C., 9° C., 10° C., 15° C., 20° C., 25° C., 30° C., 35° C., 40° C., 45° C. or more compared with an oligonucleotide that does not have the nucleotide analogue.

The oligonucleotide or region thereof may be of up to 50 nucleotides in length in which 2 to 10, 2 to 15, 2 to 16, 2 to 17, 2 to 18, 2 to 19, 2 to 20, 2 to 25, 2 to 30, 2 to 40, 2 to 45, or more nucleotides of the oligonucleotide or region thereof are nucleotide analogues. The oligonucleotide or region thereof may be of 8 to 30 nucleotides in length in which 2 to 10, 2 to 15, 2 to 16, 2 to 17, 2 to 18, 2 to 19, 2 to 20, 2 to 25, 2 to 30 nucleotides of the oligonucleotide or region thereof are nucleotide analogues. The oligonucleotide or region thereof may be of 8 to 15 nucleotides in length in which 2 to 4, 2 to 5, 2 to 6, 2 to 7, 2 to 8, 2 to 9, 2 to 10, 2 to 11, 2 to 12, 2 to 13, 2 to 14 nucleotides of the oligonucleotide or region thereof are nucleotide analogues. Optionally, the oligonucleotides or regions thereof may have every nucleotide except 1, 2, 3, 4, 5, 6, 7, 8, 9, or 10 nucleotides modified.

The oligonucleotide or region thereof (e.g., mixmer) may consist entirely of bridged nucleotides (e.g., LNA nucleotides, cEt nucleotides, ENA nucleotides). The oligonucleotide or region thereof may comprise alternating deoxyribonucleotides and 2'-fluoro-deoxyribonucleotides. The oligonucleotide or region thereof may comprise alternating deoxyribonucleotides and 2'-O-methyl nucleotides. The oligonucleotide or region thereof may comprise alternating deoxyribonucleotides and ENA nucleotide analogues. The oligonucleotide or region thereof may comprise alternating deoxyribonucleotides and LNA nucleotides. The oligonucleotide or region thereof may comprise alternating LNA nucleotides and 2'-O-methyl nucleotides. The oligonucleotide or region thereof may have a 5' nucleotide that is a bridged nucleotide (e.g., a LNA nucleotide, cEt nucleotide, ENA nucleotide). The oligonucleotide or region thereof may have a 5' nucleotide that is a deoxyribonucleotide.

The oligonucleotide or region thereof (e.g., gapmer) may comprise deoxyribonucleotides flanked by at least one bridged nucleotide (e.g., a LNA nucleotide, cEt nucleotide, ENA nucleotide) on each of the 5' and 3' ends of the deoxyribonucleotides. The oligonucleotide or region thereof may comprise deoxyribonucleotides flanked by 1, 2, 3, 4, 5, 6, 7, 8 or more bridged nucleotides (e.g., LNA nucleotides, cEt nucleotides, ENA nucleotides) on each of the 5' and 3' ends of the deoxyribonucleotides. The 3' position of the oligonucleotide or region thereof may have a 3' hydroxyl group. The 3' position of the oligonucleotide or region thereof may have a 3' thiophosphate.

The oligonucleotide may be conjugated with a label. For example, the oligonucleotide may be conjugated with a biotin moiety, cholesterol, Vitamin A, folate, sigma receptor ligands, aptamers, peptides, such as CPP, hydrophobic molecules, such as lipids, ASGPR or dynamic polyconjugates and variants thereof at its 5' or 3' end.

Preferably the oligonucleotide or region thereof comprises one or more modifications comprising: a modified sugar moiety, and/or a modified internucleoside linkage, and/or a modified nucleotide and/or combinations thereof. It is not necessary for all positions in a given oligonucleotide to be uniformly modified, and in fact more than one of the modifications described herein may be incorporated in a single oligonucleotide or even at within a single nucleoside within an oligonucleotide.

In some embodiments, the oligonucleotide or region thereof comprises at least one nucleotide modified at the 2' position of the sugar, preferably a 2'-O-alkyl, 2'-O-alkyl-O-alkyl or 2'-fluoro-modified nucleotide. In other preferred embodiments, RNA modifications include 2'-fluoro, 2'-amino and 2' O-methyl modifications on the ribose of pyrimidines, abasic residues or an inverted base at the 3' end of the RNA. Such modifications are routinely incorporated into oligonucleotides and these oligonucleotides have been shown to have a higher Tm (i.e., higher target binding affinity) than 2'-deoxyoligonucleotides against a given target.

A number of nucleotide modifications have been shown to make the oligonucleotide into which they are incorporated more resistant to nuclease digestion than the native oligodeoxynucleotide; these modified oligos survive intact for a longer time than unmodified oligonucleotides. Specific examples of modified oligonucleotides include those comprising modified backbones, for example, modified internucleoside linkages such as phosphorothioates, phosphotriesters, methyl phosphonates, short chain alkyl or cycloalkyl intersugar linkages or short chain heteroatomic or heterocyclic intersugar linkages. In some embodiments, oligonucleotides may have phosphorothioate backbones; heteroatom backbones, such as methylene(methylimino) or MMI backbones; amide backbones (see De Mesmaeker et al. Acc. Chem. Res. 1995, 28:366-374); morpholino backbones (see Summerton and Weller, U.S. Pat. No. 5,034,506); or peptide nucleic acid (PNA) backbones (wherein the phosphodiester backbone of the oligonucleotide is replaced with a polyamide backbone, the nucleotides being bound directly or indirectly to the aza nitrogen atoms of the polyamide backbone, see Nielsen et al., Science 1991, 254, 1497). Phosphorus-containing linkages include, but are not limited to, phosphorothioates, chiral phosphorothioates, phosphorodithioates, phosphotriesters, aminoalkylphosphotriesters, methyl and other alkyl phosphonates comprising 3'alkylene phosphonates and chiral phosphonates, phosphinates, phosphoramidates comprising 3'-amino phosphoramidate and aminoalkylphosphoramidates, thionophosphoramidates, thionoalkylphosphonates, thionoalkylphosphotriesters, and boranophosphates having normal 3'-5' linkages, 2'-5' linked analogs of these, and those having inverted polarity wherein the adjacent pairs of nucleoside units are linked 3'-5' to 5'-3' or 2'-5' to 5'-2'; see U.S. Pat. Nos. 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455, 233; 5,466,677; 5,476,925; 5,519,126; 5,536,821; 5,541,306; 5,550,111; 5,563, 253; 5,571,799; 5,587,361; and 5,625,050.

Morpholino-based oligomeric compounds are described in Dwaine A. Braasch and David R. Corey, Biochemistry, 2002, 41(14), 4503-4510); Genesis, volume 30, issue 3, 2001; Heasman, J., Dev. Biol., 2002, 243, 209-214; Nasevicius et al., Nat. Genet., 2000, 26, 216-220; Lacerra et al., Proc. Natl. Acad. Sci., 2000, 97, 9591-9596; and U.S. Pat. No. 5,034,506, issued Jul. 23, 1991. In some embodiments, the morpholino-based oligomeric compound is a phosphorodiamidate morpholino oligomer (PMO) (e.g., as described in Iverson, Curr. Opin. Mol. Ther., 3:235-238, 2001; and Wang et al., J. Gene Med., 12:354-364, 2010; the disclosures of which are incorporated herein by reference in their entireties).

Cyclohexenyl nucleic acid oligonucleotide mimetics are described in Wang et al., J. Am. Chem. Soc., 2000, 122, 8595-8602.

Modified oligonucleotide backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These comprise those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S and CH2 component parts; see U.S. Pat. Nos. 5,034,506; 5,166,315; 5,185,444; 5,214,134; 5,216,141; 5,235,033; 5,264, 562; 5, 264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; and 5,677,439, each of which is herein incorporated by reference.

Modified oligonucleotides are also known that include oligonucleotides that are based on or constructed from arabinonucleotide or modified arabinonucleotide residues. Arabinonucleosides are stereoisomers of ribonucleosides, differing only in the configuration at the 2'-position of the sugar ring. In some embodiments, a 2'-arabino modification is 2'-F arabino. In some embodiments, the modified oligonucleotide is 2'-fluoro-D-arabinonucleic acid (FANA) (as described in, for example, Lon et al., Biochem., 41:3457-3467, 2002 and Min et al., Bioorg. Med. Chem. Lett., 12:2651-2654, 2002; the disclosures of which are incorporated herein by reference in their entireties). Similar modifications can also be made at other positions on the sugar, particularly the 3' position of the sugar on a 3' terminal nucleoside or in 2'-5' linked oligonucleotides and the 5' position of 5' terminal nucleotide.

PCT Publication No. WO 99/67378 discloses arabinonucleic acids (ANA) oligomers and their analogues for improved sequence specific inhibition of gene expression via association to complementary messenger RNA.

Other preferred modifications include ethylene-bridged nucleic acids (ENAs) (e.g., International Patent Publication No. WO 2005/042777, Morita et al., Nucleic Acid Res., Suppl 1:241-242, 2001; Surono et al., Hum. Gene Ther., 15:749-757, 2004; Koizumi, Curr. Opin. Mol. Ther., 8:144-149, 2006 and Horie et al., Nucleic Acids Symp. Ser (Oxf), 49:171-172, 2005; the disclosures of which are incorporated herein by reference in their entireties). Preferred ENAs include, but are not limited to, 2'-O,4'-C-ethylene-bridged nucleic acids.

Examples of LNAs are described in WO/2008/043753 and include compounds of the following general formula.

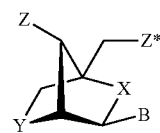

where X and Y are independently selected among the groups —O—,
—S—, —N(H)—, N(R)—, —CH$_2$— or —CH— (if part of a double bond),
—CH$_2$—O—, —CH$_2$—S—, —CH$_2$—N(H)—, —CH$_2$—N(R)—, —CH$_2$—CH$_2$— or —CH$_2$—CH— (if part of a double bond),
—CH=CH—, where R is selected from hydrogen and C$_{1-4}$-alkyl; Z and Z* are independently selected among an internucleoside linkage, a terminal group or a protecting group; B constitutes a natural or non-natural nucleotide base moiety; and the asymmetric groups may be found in either orientation.

In some embodiments, the LNA used in the oligonucleotides described herein comprises at least one LNA unit according any of the formulas

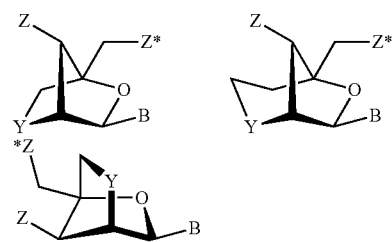

wherein Y is —O—, —S—, —NH—, or N(R$^H$); Z and Z* are independently selected among an internucleoside linkage, a terminal group or a protecting group; B constitutes a natural or non-natural nucleotide base moiety, and RH is selected from hydrogen and $C_{1-4}$-alkyl.

In some embodiments, the Locked Nucleic Acid (LNA) used in the oligonucleotides described herein comprises at least one Locked Nucleic Acid (LNA) unit according any of the formulas shown in Scheme 2 of PCT/DK2006/000512.

In some embodiments, the LNA used in the oligomer of the invention comprises internucleoside linkages selected from —O—P(O)$_2$—O—, —O—P(O,S)—O—, —O—P(S)$_2$—O—, —S—P(O)$_2$—O—, —S—P(O,S)—O—, —S—P(S)$_2$—O—, —O—P(O)$_2$—S—, —O—P(O,S)—S—, —S—P(O)$_2$—S—, —O—PO(R$^H$)—O—, O—PO (OCH$_3$)—O—, —O—PO(NR$^H$)—O—, —O—PO (OCH$_2$CH$_2$S—R)—O—, —O—PO(BH$_3$)—O—, —O—PO (NHR$^H$)—O—, —O—P(O)$_2$—NR$^H$—, —NR$^H$—P(O)$_2$—O—, —NR$^H$—CO—O—, where R$^H$ is selected from hydrogen and $C_{1-4}$-alkyl.

Specifically preferred LNA units are shown below:

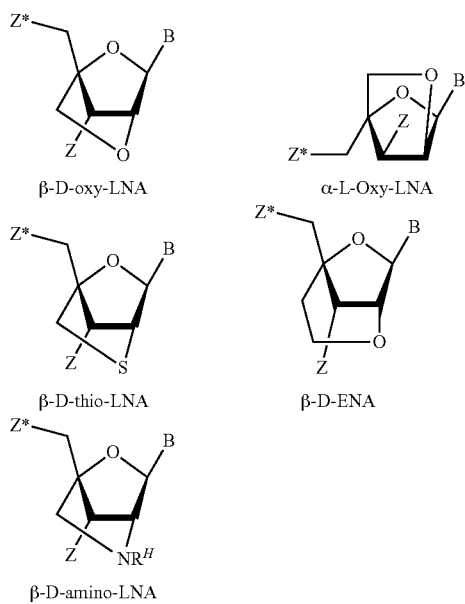

β-D-oxy-LNA

α-L-Oxy-LNA

β-D-thio-LNA

β-D-ENA

β-D-amino-LNA

The term "thio-LNA" comprises a locked nucleotide in which at least one of X or Y in the general formula above is selected from S or —CH$_2$—S—. Thio-LNA can be in both beta-D and alpha-L-configuration.

The term "amino-LNA" comprises a locked nucleotide in which at least one of X or Y in the general formula above is selected from —N(H)—, N(R)—, CH$_2$—N(H)—, and —CH$_2$—N(R)— where R is selected from hydrogen and $C_{1-4}$-alkyl. Amino-LNA can be in both beta-D and alpha-L-configuration.

The term "oxy-LNA" comprises a locked nucleotide in which at least one of X or Y in the general formula above represents —O— or —CH$_2$—O—. Oxy-LNA can be in both beta-D and alpha-L-configuration.

The term "ena-LNA" comprises a locked nucleotide in which Y in the general formula above is —CH$_2$—O— (where the oxygen atom of —CH$_2$—O— is attached to the 2'-position relative to the base B).

LNAs are described in additional detail herein.

One or more substituted sugar moieties can also be included, e.g., one of the following at the 2' position: OH, SH, SCH$_3$, F, OCN, OCH$_3$ OCH$_3$, OCH$_3$ O(CH$_2$)n CH$_3$, O(CH$_2$)n NH$_2$ or O(CH$_2$)n CH$_3$ where n is from 1 to about 10; C1 to C10 lower alkyl, alkoxyalkoxy, substituted lower alkyl, alkaryl or aralkyl; Cl; Br; CN; CF$_3$; OCF$_3$; O-, S-, or N-alkyl; O-, S-, or N-alkenyl; SOCH$_3$; SO$_2$ CH$_3$; ONO$_2$; NO$_2$; N$_3$; NH2; heterocycloalkyl; heterocycloalkaryl; aminoalkylamino; polyalkylamino; substituted silyl; an RNA cleaving group; a reporter group; an intercalator; a group for improving the pharmacokinetic properties of an oligonucleotide; or a group for improving the pharmacodynamic properties of an oligonucleotide and other substituents having similar properties. A preferred modification includes 2'-methoxyethoxy [2'-O—CH$_2$CH$_2$OCH$_3$, also known as 2'-O-(2-methoxyethyl)] (Martin et al, Helv. Chim. Acta, 1995, 78, 486). Other preferred modifications include 2'-methoxy (2'-O—CH$_3$), 2'-propoxy (2'-OCH$_2$ CH$_2$CH$_3$) and 2'-fluoro (2'-F). Similar modifications may also be made at other positions on the oligonucleotide, particularly the 3' position of the sugar on the 3' terminal nucleotide and the 5' position of 5' terminal nucleotide. Oligonucleotides may also have sugar mimetics such as cyclobutyls in place of the pentofuranosyl group.

Oligonucleotides can also include, additionally or alternatively, nucleobase (often referred to in the art simply as "base") modifications or substitutions. As used herein, "unmodified" or "natural" nucleobases include adenine (A), guanine (G), thymine (T), cytosine (C) and uracil (U). Modified nucleobases include nucleobases found only infrequently or transiently in natural nucleic acids, e.g., hypoxanthine, 6-methyladenine, 5-Me pyrimidines, particularly 5-methylcytosine (also referred to as 5-methyl-2' deoxycytosine and often referred to in the art as 5-Me-C), 5-hydroxymethylcytosine (HMC), glycosyl HMC and gentobiosyl HMC, isocytosine, pseudoisocytosine, as well as synthetic nucleobases, e.g., 2-aminoadenine, 2-(methylamino)adenine, 2-(imidazolylalkyl)adenine, 2-(aminoalkylamino)adenine or other heterosubstituted alkyladenines, 2-thiouracil, 2-thiothymine, 5-bromouracil, 5-hydroxymethyluracil, 5-propynyluracil, 8-azaguanine, 7-deazaguanine, N6 (6-aminohexyl)adenine, 6-aminopurine, 2-aminopurine, 2-chloro-6-aminopurine and 2,6-diaminopurine or other diaminopurines. See, e.g., Kornberg, "DNA Replication," W. H. Freeman & Co., San Francisco, 1980, pp 75-'7'7; and Gebeyehu, G., et al. Nucl. Acids Res., 15:4513 (1987)). A "universal" base known in the art, e.g., inosine, can also be included. 5-Me-C substitutions have been shown to increase nucleic acid duplex stability by 0.6-1.2° C. (Sanghvi, in Crooke, and Lebleu, eds., Antisense Research and Applications, CRC Press, Boca Raton, 1993, pp. 276-278) and may be used as base substitutions.

It is not necessary for all positions in a given oligonucleotide to be uniformly modified, and in fact more than one of the modifications described herein may be incorporated in a single oligonucleotide or even at within a single nucleoside within an oligonucleotide.

In some embodiments, both a sugar and an internucleoside linkage, i.e., the backbone, of the nucleotide units are replaced with novel groups. The base units are maintained for hybridization with an appropriate nucleic acid target compound. One such oligomeric compound, an oligonucleotide mimetic that has been shown to have excellent hybridization properties, is referred to as a peptide nucleic acid (PNA). In PNA compounds, the sugar-backbone of an oligonucleotide is replaced with an amide containing backbone, for example, an aminoethylglycine backbone. The nucleobases are retained and are bound directly or indirectly to aza nitrogen atoms of the amide portion of the backbone. Representative United States patents that teach the preparation of PNA compounds include, but are not limited to, U.S.

Pat. Nos. 5,539,082; 5,714,331; and 5,719,262, each of which is herein incorporated by reference. Further teaching of PNA compounds can be found in Nielsen et al, Science, 1991, 254, 1497-1500.

Oligonucleotides can also include one or more nucleobase (often referred to in the art simply as "base") modifications or substitutions. As used herein, "unmodified" or "natural" nucleobases comprise the purine bases adenine (A) and guanine (G), and the pyrimidine bases thymine (T), cytosine (C) and uracil (U). Modified nucleobases comprise other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudo-uracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylquanine and 7-methyladenine, 8-azaguanine and 8-azaadenine, 7-deazaguanine and 7-deazaadenine and 3-deazaguanine and 3-deazaadenine. In some embodiments, a cytosine is substituted with a 5-methylcytosine. In some embodiments, an oligonucleotide has 2, 3, 4, 5, 6, 7, or more cytosines substituted with a 5-methylcytosines. In some embodiments, an oligonucleotide does not have 2, 3, 4, 5, 6, 7, or more consecutive 5-methylcytosines. In some embodiments, an LNA cytosine nucleotide is replaced with an LNA 5-methylcytosine nucleotide.

Further, nucleobases comprise those disclosed in U.S. Pat. No. 3,687,808, those disclosed in "The Concise Encyclopedia of Polymer Science And Engineering", pages 858-859, Kroschwitz, ed. John Wiley & Sons, 1990; those disclosed by Englisch et al., Angewandle Chemie, International Edition, 1991, 30, page 613, and those disclosed by Sanghvi, Chapter 15, Antisense Research and Applications," pages 289-302, Crooke, and Lebleu, eds., CRC Press, 1993. Certain of these nucleobases are particularly useful for increasing the binding affinity of the oligomeric compounds of the invention. These include 5-substituted pyrimidines, 6-azapyrimidines and N-2, N-6 and 0-6 substituted purines, comprising 2-aminopropyladenine, 5-propynyluracil and 5-propynylcytosine. 5-methylcytosine substitutions have been shown to increase nucleic acid duplex stability by 0.6-1.2<0>C (Sanghvi, et al., eds, "Antisense Research and Applications," CRC Press, Boca Raton, 1993, pp. 276-278) and are presently preferred base substitutions, even more particularly when combined with 2'-O-methoxyethyl sugar modifications. Modified nucleobases are described in U.S. Pat. No. 3,687,808, as well as U.S. Pat. Nos. 4,845,205; 5,130,302; 5,134,066; 5,175, 273; 5, 367,066; 5,432,272; 5,457,187; 5,459,255; 5,484,908; 5,502,177; 5,525,711; 5,552,540; 5,587,469; 5,596,091; 5,614,617; 5,750,692, and 5,681,941, each of which is herein incorporated by reference.

In some embodiments, the oligonucleotides are chemically linked to one or more moieties or conjugates that enhance the activity, cellular distribution, or cellular uptake of the oligonucleotide. For example, one or more oligonucleotides, of the same or different types, can be conjugated to each other; or oligonucleotides can be conjugated to targeting moieties with enhanced specificity for a cell type or tissue type. Such moieties include, but are not limited to, lipid moieties such as a cholesterol moiety (Letsinger et al., Proc. Natl. Acad. Sci. USA, 1989, 86, 6553-6556), cholic acid (Manoharan et al., Bioorg. Med. Chem. Let., 1994, 4, 1053-1060), a thioether, e.g., hexyl-S— tritylthiol (Manoharan et al, Ann. N. Y. Acad. Sci., 1992, 660, 306-309; Manoharan et al., Bioorg. Med. Chem. Let., 1993, 3, 2765-2770), a thiocholesterol (Oberhauser et al., Nucl. Acids Res., 1992, 20, 533-538), an aliphatic chain, e.g., dodecandiol or undecyl residues (Kabanov et al., FEBS Lett., 1990, 259, 327-330; Svinarchuk et al., Biochimie, 1993, 75, 49-54), a phospholipid, e.g., di-hexadecyl-rac-glycerol or triethylammonium 1,2-di-O-hexadecyl-rac-glycero-3-H-phosphonate (Manoharan et al., Tetrahedron Lett., 1995, 36, 3651-3654; Shea et al., Nucl. Acids Res., 1990, 18, 3777-3783), a polyamine or a polyethylene glycol chain (Mancharan et al., Nucleosides & Nucleotides, 1995, 14, 969-973), or adamantane acetic acid (Manoharan et al., Tetrahedron Lett., 1995, 36, 3651-3654), a palmityl moiety (Mishra et al., Biochim. Biophys. Acta, 1995, 1264, 229-237), or an octadecylamine or hexylamino-carbonyl-t oxycholesterol moiety (Crooke et al., J. Pharmacol. Exp. Ther., 1996, 277, 923-937). See also U.S. Pat. Nos. 4,828,979; 4,948,882; 5,218,105; 5,525,465; 5,541,313; 5,545,730; 5,552, 538; 5,578,717, 5,580,731; 5,580,731; 5,591,584; 5,109,124; 5,118,802; 5,138,045; 5,414,077; 5,486, 603; 5,512,439; 5,578,718; 5,608,046; 4,587,044; 4,605,735; 4,667,025; 4,762, 779; 4,789,737; 4,824,941; 4,835,263; 4,876,335; 4,904,582; 4,958,013; 5,082, 830; 5,112,963; 5,214,136; 5,082,830; 5,112,963; 5,214,136; 5, 245,022; 5,254,469; 5,258,506; 5,262,536; 5,272,250; 5,292,873; 5,317,098; 5,371,241, 5,391, 723; 5,416,203, 5,451,463; 5,510,475; 5,512,667; 5,514,785; 5, 565,552; 5,567,810; 5,574,142; 5,585,481; 5,587,371; 5,595,726; 5,597,696; 5,599,923; 5,599, 928 and 5,688,941, each of which is herein incorporated by reference.

These moieties or conjugates can include conjugate groups covalently bound to functional groups such as primary or secondary hydroxyl groups. Conjugate groups of the invention include intercalators, reporter molecules, polyamines, polyamides, polyethylene glycols, polyethers, groups that enhance the pharmacodynamic properties of oligomers, and groups that enhance the pharmacokinetic properties of oligomers. Typical conjugate groups include cholesterols, lipids, phospholipids, biotin, phenazine, folate, phenanthridine, anthraquinone, acridine, fluoresceins, rhodamines, coumarins, and dyes. Groups that enhance the pharmacodynamic properties, in the context of this invention, include groups that improve uptake, enhance resistance to degradation, and/or strengthen sequence-specific hybridization with the target nucleic acid. Groups that enhance the pharmacokinetic properties, in the context of this invention, include groups that improve uptake, distribution, metabolism or excretion of the compounds of the present invention. Representative conjugate groups are disclosed in International Patent Application No. PCT/US92/09196, filed Oct. 23, 1992, and U.S. Pat. No. 6,287,860, which are incorporated herein by reference. Conjugate moieties include, but are not limited to, lipid moieties such as a cholesterol moiety, cholic acid, a thioether, e.g., hexyl-5-tritylthiol, a thiocholesterol, an aliphatic chain, e.g., dodecandiol or undecyl residues, a phospholipid, e.g., di-hexadecyl-rac-glycerol or triethylammonium1,2-di-O-hexadecyl-rac-glycero-3-H-phosphonate, a polyamine or a polyethylene glycol chain, or adamantane acetic acid, a palmityl moiety, or an octadecylamine or hexylamino-carbonyl-oxy cholesterol moiety. See, e.g., U.S. Pat. Nos. 4,828,979; 4,948,882; 5,218,105; 5,525,465; 5,541,313; 5,545,730; 5,552,538; 5,578,717; 5,580,731; 5,580,731; 5,591,584; 5,109,124; 5,118,802; 5,138,045; 5,414,077; 5,486,603; 5,512,439; 5,578,718; 5,608,046; 4,587,044; 4,605,735; 4,667,025;

4,762,779; 4,789,737; 4,824,941; 4,835,263; 4,876,335; 4,904,582; 4,958,013; 5,082,830; 5,112,963; 5,214,136; 5,082,830; 5,112,963; 5,214,136; 5,245,022; 5,254,469; 5,258,506; 5,262,536; 5,272,250; 5,292,873; 5,317,098; 5,371,241; 5,391,723; 5,416,203; 5,451,463; 5,510,475; 5,512,667; 5,514,785; 5,565,552; 5,567,810; 5,574,142; 5,585,481; 5,587,371; 5,595,726; 5,597,696; 5,599,923; 5,599,928 and 5,688,941.

In some embodiments, oligonucleotide modification includes modification of the 5' or 3' end of the oligonucleotide. In some embodiments, the 3' end of the oligonucleotide comprises a hydroxyl group or a thiophosphate. It should be appreciated that additional molecules (e.g. a biotin moiety or a fluorophor) can be conjugated to the 5' or 3' end of the oligonucleotide. In some embodiments, the oligonucleotide comprises a biotin moiety conjugated to the 5' nucleotide.

In some embodiments, the oligonucleotide or region thereof comprises locked nucleic acids (LNA), ENA modified nucleotides, 2'-O-methyl nucleotides, or 2'-fluoro-deoxyribonucleotides. In some embodiments, the oligonucleotide or region thereof comprises alternating deoxyribonucleotides and 2'-fluoro-deoxyribonucleotides. In some embodiments, the oligonucleotide or region thereof comprises alternating deoxyribonucleotides and 2'-O-methyl nucleotides. In some embodiments, the oligonucleotide or region thereof comprises alternating deoxyribonucleotides and ENA modified nucleotides. In some embodiments, the oligonucleotide or region thereof comprises alternating deoxyribonucleotides and locked nucleic acid nucleotides. In some embodiments, the oligonucleotide or region thereof comprises alternating locked nucleic acid nucleotides and 2'-O-methyl nucleotides.

In some embodiments, the 5' nucleotide of the oligonucleotide is a deoxyribonucleotide. In some embodiments, the 5' nucleotide of the oligonucleotide is a locked nucleic acid nucleotide. In some embodiments, the nucleotides of the oligonucleotide comprise deoxyribonucleotides flanked by at least one locked nucleic acid nucleotide on each of the 5' and 3' ends of the deoxyribonucleotides. In some embodiments, the nucleotide at the 3' position of the oligonucleotide has a 3' hydroxyl group or a 3' thiophosphate.

In some embodiments, the oligonucleotide or region thereof comprises phosphorothioate internucleoside linkages. In some embodiments, the oligonucleotide or region thereof comprises phosphorothioate internucleoside linkages between at least two nucleotides. In some embodiments, the oligonucleotide or region thereof comprises phosphorothioate internucleoside linkages between all nucleotides.

It should be appreciated that the oligonucleotide can have any combination of modifications as described herein.

Producing Candidate Oligonucleotides

In some embodiments, methods are provided for producing candidate oligonucleotides that are useful for, e.g., enhancing expression of a gene. Generally, the oligonucleotides are complementary to sequences in a target RNA.

Typically, the oligonucleotides are designed by determining a region of a target RNA to remove by cleavage; producing an oligonucleotide that has a region of complementarity that is complementary with a plurality of (e.g., at least 5) contiguous nucleotides of the target RNA; and determining whether administering the oligonucleotide to a cell in which the gene is silenced or downregulated results in induction of expression of the gene and/or reduction or elimination of the target RNA containing the region to be removed.

In some embodiments, methods are provided for obtaining one or more oligonucleotides for increasing expression of a target gene that further involve producing a plurality of different oligonucleotides, in which each oligonucleotide has a region of complementarity that is complementary with a plurality of (e.g., at least 5) contiguous nucleotides in a target RNA; subjecting each of the different oligonucleotides to an assay that assesses whether delivery of an oligonucleotide to a cell harboring the target gene results in increased expression of the target gene in the cell; and obtaining one or more oligonucleotides that increase expression of the target gene in the assay.

Methods for Increasing Gene Expression

In one aspect, the invention relates to methods for increasing gene expression in a cell for research purposes (e.g., to study the function of the gene in the cell). In another aspect, the invention relates to methods for increasing gene expression in a cell for therapeutic purposes. The cells can be in vitro, ex vivo, or in vivo (e.g., in a subject in need thereof, such as a subject who has a disease resulting from reduced expression or activity of a target gene). In some embodiments, methods for increasing gene expression in a cell comprise delivering an oligonucleotide or composition as described herein. In some embodiments, gene expression is increased by at least 5%, 10%, 20%, 30%, 40%, 50%, 60%, 70%, 80%, 90%, 100%, 200% or more greater than gene expression in a control cell or control subject. An appropriate control cell or subject may be a cell, tissue or subject to which an oligonucleotide or composition has not been delivered or to which a negative control has been delivered (e.g., a scrambled oligo, a carrier, etc.). In some embodiments, gene expression includes an increase of protein expression by at least 5%, 10%, 20%, 30%, 40%, 50%, 60%, 70%, 80%, 90%, 100%, 200%, or more, higher than the amount of a protein in the subject (e.g., in a cell or tissue of the subject) before administering an oligonucleotide or composition or in a control subject which has not been administered the oligonucleotide or composition or that has been administered a negative control (e.g., a scrambled oligo, a carrier, etc.).

In some embodiments, methods are provided for treating a disease or condition associated with decreased expression of a target gene, such as a gene provided in Table 1. Exemplary diseases and conditions are provided in Table 6.

TABLE 6

Examples of diseases or conditions

| Gene | Disease or conditions |
|------|----------------------|
| FXN  | Friedreich's Ataxia |
| SMN  | Spinal muscular atrophy (SMA) types I-IV |
| UTRN | Muscular dystrophy (MD) (e.g., Duchenne's muscular dystrophy, Becker's muscular dystrophy, myotonic dystrophy) |

TABLE 6-continued

Examples of diseases or conditions

| Gene | Disease or conditions |
|---|---|
| HEMOGLOBIN | Anemia, microcytic anemia, sickle cell anemia and/or thalassemia (e.g., alpha-thalassemia, beta-thalaseemia, delta-thalessemia), beta-thalaseemia (e.g., thalassemia minor/intermedia/major) |
| ATP2A2 | Cardiac conditions (e.g., congenital heart disease, aortic aneurysms, aortic dissections, arrhythmia, cardiomyopathy, and congestive heart failure), Darier-White disease and Acrokeratosis verruciformi |
| APOA1/ ABCA1 | Dyslipidemia (e.g. Hyperlipidemia) and atherosclerosis (e.g. coronary artery disease (CAD) and myocardial infarction (MI)) |
| PTEN | Cancer, such as, leukemias, lymphomas, myelomas, carcinomas, metastatic carcinomas, sarcomas, adenomas, nervous system cancers and genito-urinary cancers. In some embodiments, the cancer is adult and pediatric acute lymphoblastic leukemia, acute myeloid leukemia, adrenocortical carcinoma, AIDS-related cancers, anal cancer, cancer of the appendix, astrocytoma, basal cell carcinoma, bile duct cancer, bladder cancer, bone cancer, osteosarcoma, fibrous histiocytoma, brain cancer, brain stem glioma, cerebellar astrocytoma, malignant glioma, ependymoma, medulloblastoma, supratentorial primitive neuroectodermal tumors, hypothalamic glioma, breast cancer, male breast cancer, bronchial adenomas, Burkitt lymphoma, carcinoid tumor, carcinoma of unknown origin, central nervous system lymphoma, cerebellar astrocytoma, malignant glioma, cervical cancer, childhood cancers, chronic lymphocytic leukemia, chronic myelogenous leukemia, chronic myeloproliferative disorders, colorectal cancer, cutaneous T-cell lymphoma, endometrial cancer, ependymoma, esophageal cancer, Ewing family tumors, extracranial germ cell tumor, extragonadal germ cell tumor, extrahepatic bile duct cancer, intraocular melanoma, retinoblastoma, gallbladder cancer, gastric cancer, gastrointestinal stromal tumor, extracranial germ cell tumor, extragonadal germ cell tumor, ovarian germ cell tumor, gestational trophoblastic tumor, glioma, hairy cell leukemia, head and neck cancer, hepatocellular cancer, Hodgkin lymphoma, non-Hodgkin lymphoma, hypopharyngeal cancer, hypothalamic and visual pathway glioma, intraocular melanoma, islet cell tumors, Kaposi sarcoma, kidney cancer, renal cell cancer, laryngeal cancer, lip and oral cavity cancer, small cell lung cancer, non-small cell lung cancer, primary central nervous system lymphoma, Waldenstrom macroglobulinema, malignant fibrous histiocytoma, medulloblastoma, melanoma, Merkel cell carcinoma, malignant mesothelioma, squamous neck cancer, multiple endocrine neoplasia syndrome, multiple myeloma, mycosis fungoides, myelodysplastic syndromes, myeloproliferative disorders, chronic myeloproliferative disorders, nasal cavity and paranasal sinus cancer, nasopharyngeal cancer, neuroblastoma, oropharyngeal cancer, ovarian cancer, pancreatic cancer, parathyroid cancer, penile cancer, pharyngeal cancer, pheochromocytoma, pineoblastoma and supratentorial primitive neuroectodermal tumors, pituitary cancer, plasma cell neoplasms, pleuropulmonary blastoma, prostate cancer, rectal cancer, rhabdomyosarcoma, salivary gland cancer, soft tissue sarcoma, uterine sarcoma, Sezary syndrome, non-melanoma skin cancer, small intestine cancer, squamous cell carcinoma, squamous neck cancer, supratentorial primitive neuroectodermal tumors, testicular cancer, throat cancer, thymoma and thymic carcinoma, thyroid cancer, transitional cell cancer, trophoblastic tumors, urethral cancer, uterine cancer, uterine sarcoma, vaginal cancer, vulvar cancer, or Wilms tumor |
| BDNF | Amyotrophic lateral sclerosis (ALS, also known as Lou Gehrig's disease), Alzheimer's Disease (AD), and Parkinson's Disease (PD), Neurodegeneration |
| MECP2 | Rett Syndrome, MECP2-related severe neonatal encephalopathy, Angelman syndrome, or PPM-X syndrome |
| FOXP3 | Diseases or disorders associated with aberrant immune cell (e.g., T cell) activation, e.g., autoimmune or inflammatory diseases or disorders. Examples of autoimmune diseases and disorders that may be treated according to the methods disclosed herein include, but are not limited to, Acute Disseminated Encephalomyelitis (ADEM), Acute necrotizing hemorrhagic leukoencephalitis, Addison's disease, Agammaglobulinemia, Alopecia areata, Amyloidosis, Ankylosing spondylitis, Anti-GBM/Anti-TBM nephritis, Antiphospholipid syndrome (APS), Autoimmune angioedema, Autoimmune aplastic anemia, Autoimmune dysautonomia, Autoimmune hepatitis, Autoimmune hyperlipidemia, Autoimmune immunodeficiency, Autoimmune inner ear disease (AIED), Autoimmune myocarditis, Autoimmune oophoritis, Autoimmune pancreatitis, Autoimmune retinopathy, Autoimmune thrombocytopenic purpura (ATP), Autoimmune thyroid disease, Autoimmune urticaria, Axonal & neuronal neuropathies, Balo disease, Behcet's disease, Bullous pemphigoid, Cardiomyopathy, Castleman disease, Celiac disease, Chagas disease, Chronic inflammatory demyelinating polyneuropathy (CIDP), Chronic recurrent multifocal ostomyelitis (CRMO), Churg-Strauss syndrome, Cicatricial |

TABLE 6-continued

Examples of diseases or conditions

| Gene | Disease or conditions |
|---|---|
| | pemphigoid/benign mucosal pemphigoid, inflammatory bowel disease (e.g., Crohn's disease or Ulcerative colitis), Cogans syndrome, Cold agglutinin disease, Congenital heart block, Coxsackie myocarditis, CREST disease, Essential mixed cryoglobulinemia, Demyelinating neuropathies, Dermatitis herpetiformis, Dermatomyositis, Devic's disease (neuromyelitis optica), Discoid lupus, Dressler's syndrome, Endometriosis, Eosinophilic esophagitis, Eosinophilic fasciitis, Erythema nodosum, Experimental allergic encephalomyelitis, Evans syndrome, Fibrosing alveolitis, Giant cell arteritis (temporal arteritis), Giant cell myocarditis, Glomerulonephritis, Goodpasture's syndrome, Granulomatosis with Polyangiitis (GPA) (formerly called Wegener's Granulomatosis), Graves' disease, Guillain-Barre syndrome, Hashimoto's encephalitis, Hashimoto's thyroiditis, Hemolytic anemia, Henoch-Schonlein purpura, Herpes gestationis, Hypogammaglobulinemia, Idiopathic thrombocytopenic purpura (ITP), IgA nephropathy, IgG4-related sclerosing disease, Immunoregulatory lipoproteins, Inclusion body myositis, Interstitial cystitis, IPEX (Immunodysregulation, Polyendocrinopathy, and Enteropathy, X-linked) syndrome, Juvenile arthritis, Juvenile diabetes (Type 1 diabetes), Juvenile myositis, Kawasaki syndrome, Lambert-Eaton syndrome, Leukocytoclastic vasculitis, Lichen planus, Lichen sclerosus, Ligneous conjunctivitis, Linear IgA disease (LAD), systemic lupus erythematosus (SLE), chronic Lyme disease, Meniere's disease, Microscopic polyangiitis, Mixed connective tissue disease (MCTD), Mooren's ulcer, Mucha-Habermann disease, Multiple sclerosis, Myasthenia gravis, Myositis, Narcolepsy, Neuromyelitis optica (Devic's), Neutropenia, Ocular cicatricial pemphigoid, Optic neuritis, Palindromic rheumatism, PANDAS (Pediatric Autoimmune Neuropsychiatric Disorders Associated with Streptococcus), Paraneoplastic cerebellar degeneration, Paroxysmal nocturnal hemoglobinuria (PNH), Parry Romberg syndrome, Parsonnage-Turner syndrome, Pars planitis (peripheral uveitis), Pemphigus, Peripheral neuropathy, Perivenous encephalomyelitis, Pernicious anemia, POEMS syndrome, Polyarteritis nodosa, Type I, II, & III autoimmune polyglandular syndromes, Polymyalgia rheumatica, Polymyositis, Postmyocardial infarction syndrome, Postpericardiotomy syndrome, Progesterone dermatitis, Primary biliary cirrhosis, Primary sclerosing cholangitis, Psoriasis, Psoriatic arthritis, Idiopathic pulmonary fibrosis, Pyoderma gangrenosum, Pure red cell aplasia, Raynauds phenomenon, Reactive Arthritis, Reflex sympathetic dystrophy, Reiter's syndrome, Relapsing polychondritis, Restless legs syndrome, Retroperitoneal fibrosis, Rheumatic fever, Rheumatoid arthritis, Sarcoidosis, Schmidt syndrome, Scleritis, Scleroderma, Sjogren's syndrome, Sperm & testicular autoimmunity, Stiff person syndrome, Subacute bacterial endocarditis (SBE), Susac's syndrome, Sympathetic ophthalmia, Takayasu's arteritis, Temporal arteritis/Giant cell arteritis, Thrombocytopenic purpura (TTP), Tolosa-Hunt syndrome, Transverse myelitis, Type 1 diabetes, Undifferentiated connective tissue disease (UCTD), Uveitis, Vasculitis, Vesiculobullous dermatosis, Vitiligo, and Wegener's granulomatosis (also called Granulomatosis with Polyangiitis (GPA)). Further examples of autoimmune disease or disorder include inflammatory bowel disease (e.g., Crohn's disease or Ulcerative colitis), IPEX syndrome, Multiple sclerosis, Psoriasis, Rheumatoid arthritis, SLE or Type 1 diabetes. Examples of inflammatory diseases or disorders that may be treated according to the methods disclosed herein include, but are not limited to, Acne Vulgaris, Appendicitis, Arthritis, Asthma, Atherosclerosis, Allergies (Type 1 Hypersensitivity), Bursitis, Colitis, Chronic Prostatitis, Cystitis, Dermatitis, Glomerulonephritis, Inflammatory Bowel Disease, Inflammatory Myopathy (e.g., Polymyositis, Dermatomyositis, or Inclusion-body Myositis), Inflammatory Lung Disease, Interstitial Cystitis, Meningitis, Pelvic Inflammatory Disease, Phlebitis, Psoriasis, Reperfusion Injury, Rheumatoid Arthritis, Sarcoidosis, Tendonitis, Tonsilitis, Transplant Rejection, and Vasculitis. In some embodiments, the inflammatory disease or disorder is asthma. |
| THRB | Thyroid hormone resistance, mixed dyslipidemia, dyslipidemia, hypercholesterolemia, metabolic complications arising from high-fat diets, such as Non-Alcoholic Fatty Liver Disease (NAFLD) and Non-Alcoholic Steatohepatitis (NASH), and other liver conditions |
| NR1H4 | Byler disease, cholestasis, cholestasis intrahepatic, dyslipidemia, biliary cirrhosis primary, fragile x syndrome, hypercholesterolemia, atherosclerosis, biliary atresia |
| HAMP | Hemochromatosis (juvenile), hemochromatosis, iron overload, hereditary hemochromatosis, anemia, inflammation, thalassemia |

Typically, the methods involve administering to a subject an effective amount of an oligonucleotide for increasing expression of the gene. In some embodiments, the disease is associated with the presence of a repeat sequence in the target RNA, such as is Angelman syndrome, myotonic dystrophy type 1, Friedreich's ataxia, fragile x syndrome, or Prader-Willi syndrome.

It is understood that any reference to uses of compounds throughout the description contemplates use of the compound in preparation of a pharmaceutical composition or medicament for use in the treatment of a condition or a disease. Thus, as one non-limiting example, this aspect of the invention includes use of such oligonucleotides in the preparation of a medicament for use in the treatment of a disease or disorder as described herein.

Formulation, Delivery, And Dosing

The oligonucleotides described herein can be formulated for administration to a subject for treating a condition or disease, e.g., associated with decreased levels of a target gene. It should be understood that the formulations, compositions and methods can be practiced with any of the oligonucleotides disclosed herein.

The formulations may conveniently be presented in unit dosage form and may be prepared by any methods well known in the art of pharmacy. The amount of active ingredient (e.g., an oligonucleotide or compound of the invention) which can be combined with a carrier material to produce a single dosage form will vary depending upon the host being treated, the particular mode of administration, e.g., intradermal or inhalation. The amount of active ingredient which can be combined with a carrier material to produce a single dosage form will generally be that amount of the compound which produces a therapeutic effect, e.g. tumor regression.

Pharmaceutical formulations of this invention can be prepared according to any method known to the art for the manufacture of pharmaceuticals. Such formulations can contain sweetening agents, flavoring agents, coloring agents and preserving agents. A formulation can be admixtured with nontoxic pharmaceutically acceptable excipients which are suitable for manufacture. Formulations may comprise one or more diluents, emulsifiers, preservatives, buffers, excipients, etc. and may be provided in such forms as liquids, powders, emulsions, lyophilized powders, sprays, creams, lotions, controlled release formulations, tablets, pills, gels, on patches, in implants, etc.

A formulated single stranded oligonucleotide composition can assume a variety of states. In some examples, the composition is at least partially crystalline, uniformly crystalline, and/or anhydrous (e.g., less than 80, 50, 30, 20, or 10% water). In another example, the single stranded oligonucleotide is in an aqueous phase, e.g., in a solution that includes water. The aqueous phase or the crystalline compositions can, e.g., be incorporated into a delivery vehicle, e.g., a liposome (particularly for the aqueous phase) or a particle (e.g., a microparticle as can be appropriate for a crystalline composition). Generally, the single stranded oligonucleotide composition is formulated in a manner that is compatible with the intended method of administration.

In some embodiments, the composition is prepared by at least one of the following methods: spray drying, lyophilization, vacuum drying, evaporation, fluid bed drying, or a combination of these techniques; or sonication with a lipid, freeze-drying, condensation and other self-assembly.

A single stranded oligonucleotide preparation can be formulated or administered (together or separately) in combination with another agent, e.g., another therapeutic agent or an agent that stabilizes a single stranded oligonucleotide, e.g., a protein that complexes with single stranded oligonucleotide. Still other agents include chelators, e.g., EDTA (e.g., to remove divalent cations such as $Mg^{2+}$), salts, RNAse inhibitors (e.g., a broad specificity RNAse inhibitor such as RNAsin) and so forth.

In one embodiment, the single stranded oligonucleotide preparation includes another single stranded oligonucleotide, e.g., a second single stranded oligonucleotide that modulates expression of a second gene or a second single stranded oligonucleotide that modulates expression of the first gene. Still other preparation can include at least 3, 5, ten, twenty, fifty, or a hundred or more different single stranded oligonucleotide species. Such single stranded oligonucleotides can mediated gene expression with respect to a similar number of different genes. In one embodiment, the single stranded oligonucleotide preparation includes at least a second therapeutic agent (e.g., an agent other than an oligonucleotide).

Route of Delivery

A composition that includes a single stranded oligonucleotide can be delivered to a subject by a variety of routes. Exemplary routes include: intravenous, intradermal, topical, rectal, parenteral, anal, intravaginal, intranasal, pulmonary, ocular, and oral. The term "therapeutically effective amount" is the amount of oligonucleotide present in the composition that is needed to provide the desired level of target gene expression in the subject to be treated to give the anticipated physiological response. The term "physiologically effective amount" is that amount delivered to a subject to give the desired palliative or curative effect. The term "pharmaceutically acceptable carrier" means that the carrier can be administered to a subject with no significant adverse toxicological effects to the subject.

The single stranded oligonucleotide molecules of the invention can be incorporated into pharmaceutical compositions suitable for administration. Such compositions typically include one or more species of single stranded oligonucleotide and a pharmaceutically acceptable carrier. As used herein the language "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

The pharmaceutical compositions of the present invention may be administered in a number of ways depending upon whether local or systemic treatment is desired and upon the area to be treated. Administration may be topical (including ophthalmic, vaginal, rectal, intranasal, transdermal), oral or parenteral. Parenteral administration includes intravenous drip, subcutaneous, intraperitoneal or intramuscular injection, or intrathecal or intraventricular administration.

The route and site of administration may be chosen to enhance targeting. For example, to target muscle cells, intramuscular injection into the muscles of interest would be a logical choice. Lung cells might be targeted by administering the single stranded oligonucleotide in aerosol form. The vascular endothelial cells could be targeted by coating a balloon catheter with the single stranded oligonucleotide and mechanically introducing the oligonucleotide.

Topical administration refers to the delivery to a subject by contacting the formulation directly to a surface of the subject. The most common form of topical delivery is to the skin, but a composition disclosed herein can also be directly applied to other surfaces of the body, e.g., to the eye, a mucous membrane, to surfaces of a body cavity or to an internal surface. As mentioned above, the most common topical delivery is to the skin. The term encompasses several routes of administration including, but not limited to, topical and transdermal. These modes of administration typically include penetration of the skin's permeability barrier and efficient delivery to the target tissue or stratum. Topical administration can be used as a means to penetrate the epidermis and dermis and ultimately achieve systemic delivery of the composition. Topical administration can also be used as a means to selectively deliver oligonucleotides to the epidermis or dermis of a subject, or to specific strata thereof, or to an underlying tissue.

Formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable. Coated condoms, gloves and the like may also be useful.

Transdermal delivery is a valuable route for the administration of lipid soluble therapeutics. The dermis is more permeable than the epidermis and therefore absorption is much more rapid through abraded, burned or denuded skin. Inflammation and other physiologic conditions that increase blood flow to the skin also enhance transdermal adsorption. Absorption via this route may be enhanced by the use of an oily vehicle (inunction) or through the use of one or more penetration enhancers. Other effective ways to deliver a composition disclosed herein via the transdermal route include hydration of the skin and the use of controlled release topical patches. The transdermal route provides a potentially effective means to deliver a composition disclosed herein for systemic and/or local therapy. In addition, iontophoresis (transfer of ionic solutes through biological membranes under the influence of an electric field), phonophoresis or sonophoresis (use of ultrasound to enhance the absorption of various therapeutic agents across biological membranes, notably the skin and the cornea), and optimization of vehicle characteristics relative to dose position and retention at the site of administration may be useful methods for enhancing the transport of topically applied compositions across skin and mucosal sites.

Both the oral and nasal membranes offer advantages over other routes of administration. For example, oligonucleotides administered through these membranes may have a rapid onset of action, provide therapeutic plasma levels, avoid first pass effect of hepatic metabolism, and avoid exposure of the oligonucleotides to the hostile gastrointestinal (GI) environment. Additional advantages include easy access to the membrane sites so that the oligonucleotide can be applied, localized and removed easily.

In oral delivery, compositions can be targeted to a surface of the oral cavity, e.g., to sublingual mucosa which includes the membrane of ventral surface of the tongue and the floor of the mouth or the buccal mucosa which constitutes the lining of the cheek. The sublingual mucosa is relatively permeable thus giving rapid absorption and acceptable bioavailability of many agents. Further, the sublingual mucosa is convenient, acceptable and easily accessible.

A pharmaceutical composition of single stranded oligonucleotide may also be administered to the buccal cavity of a human being by spraying into the cavity, without inhalation, from a metered dose spray dispenser, a mixed micellar pharmaceutical formulation as described above and a propellant. In one embodiment, the dispenser is first shaken prior to spraying the pharmaceutical formulation and propellant into the buccal cavity.

Compositions for oral administration include powders or granules, suspensions or solutions in water, syrups, slurries, emulsions, elixirs or non-aqueous media, tablets, capsules, lozenges, or troches. In the case of tablets, carriers that can be used include lactose, sodium citrate and salts of phosphoric acid. Various disintegrants such as starch, and lubricating agents such as magnesium stearate, sodium lauryl sulfate and talc, are commonly used in tablets. For oral administration in capsule form, useful diluents are lactose and high molecular weight polyethylene glycols. When aqueous suspensions are required for oral use, the nucleic acid compositions can be combined with emulsifying and suspending agents. If desired, certain sweetening and/or flavoring agents can be added.

Parenteral administration includes intravenous drip, subcutaneous, intraperitoneal or intramuscular injection, intrathecal or intraventricular administration. In some embodiments, parental administration involves administration directly to the site of disease (e.g. injection into a tumor).

Formulations for parenteral administration may include sterile aqueous solutions which may also contain buffers, diluents and other suitable additives. Intraventricular injection may be facilitated by an intraventricular catheter, for example, attached to a reservoir. For intravenous use, the total concentration of solutes should be controlled to render the preparation isotonic.

Any of the single stranded oligonucleotides described herein can be administered to ocular tissue. For example, the compositions can be applied to the surface of the eye or nearby tissue, e.g., the inside of the eyelid. For ocular administration, ointments or droppable liquids may be delivered by ocular delivery systems known to the art such as applicators or eye droppers. Such compositions can include mucomimetics such as hyaluronic acid, chondroitin sulfate, hydroxypropyl methylcellulose or poly(vinyl alcohol), preservatives such as sorbic acid, EDTA or benzylchronium chloride, and the usual quantities of diluents and/or carriers. The single stranded oligonucleotide can also be administered to the interior of the eye, and can be introduced by a needle or other delivery device which can introduce it to a selected area or structure.

Pulmonary delivery compositions can be delivered by inhalation by the patient of a dispersion so that the composition, preferably single stranded oligonucleotides, within the dispersion can reach the lung where it can be readily absorbed through the alveolar region directly into blood circulation. Pulmonary delivery can be effective both for systemic delivery and for localized delivery to treat diseases of the lungs.

Pulmonary delivery can be achieved by different approaches, including the use of nebulized, aerosolized, micellular and dry powder-based formulations. Delivery can be achieved with liquid nebulizers, aerosol-based inhalers, and dry powder dispersion devices. Metered-dose devices are preferred. One of the benefits of using an atomizer or inhaler is that the potential for contamination is minimized because the devices are self-contained. Dry powder dispersion devices, for example, deliver agents that may be readily formulated as dry powders. A single stranded oligonucleotide composition may be stably stored as lyophilized or spray-dried powders by itself or in combination with suitable powder carriers. The delivery of a composition for inhalation can be mediated by a dosing timing element which can include a timer, a dose counter, time measuring device, or a time indicator which when incorporated into the device enables dose tracking, compliance monitoring, and/ or dose triggering to a patient during administration of the aerosol medicament.

The term "powder" means a composition that consists of finely dispersed solid particles that are free flowing and capable of being readily dispersed in an inhalation device and subsequently inhaled by a subject so that the particles reach the lungs to permit penetration into the alveoli. Thus, the powder is said to be "respirable." Preferably the average particle size is less than about 10 µm in diameter preferably with a relatively uniform spheroidal shape distribution. More preferably the diameter is less than about 7.5 µm and most preferably less than about 5.0 µm. Usually the particle size distribution is between about 0.1 µm and about 5 µm in diameter, particularly about 0.3 µm to about 5 µm.

The term "dry" means that the composition has a moisture content below about 10% by weight (% w) water, usually below about 5% w and preferably less it than about 3% w. A dry composition can be such that the particles are readily dispersible in an inhalation device to form an aerosol.

The types of pharmaceutical excipients that are useful as carrier include stabilizers such as human serum albumin (HSA), bulking agents such as carbohydrates, amino acids and polypeptides; pH adjusters or buffers; salts such as sodium chloride; and the like. These carriers may be in a crystalline or amorphous form or may be a mixture of the two.

Suitable pH adjusters or buffers include organic salts prepared from organic acids and bases, such as sodium citrate, sodium ascorbate, and the like; sodium citrate is preferred. Pulmonary administration of a micellar single stranded oligonucleotide formulation may be achieved through metered dose spray devices with propellants such as tetrafluoroethane, heptafluoroethane, dimethylfluoropropane, tetrafluoropropane, butane, isobutane, dimethyl ether and other non-CFC and CFC propellants.

Exemplary devices include devices which are introduced into the vasculature, e.g., devices inserted into the lumen of a vascular tissue, or which devices themselves form a part of the vasculature, including stents, catheters, heart valves, and other vascular devices. These devices, e.g., catheters or stents, can be placed in the vasculature of the lung, heart, or leg.

Other devices include non-vascular devices, e.g., devices implanted in the peritoneum, or in organ or glandular tissue, e.g., artificial organs. The device can release a therapeutic substance in addition to a single stranded oligonucleotide, e.g., a device can release insulin.

In one embodiment, unit doses or measured doses of a composition that includes single stranded oligonucleotide are dispensed by an implanted device. The device can include a sensor that monitors a parameter within a subject. For example, the device can include pump, e.g., and, optionally, associated electronics.

Tissue, e.g., cells or organs can be treated with a single stranded oligonucleotide, ex vivo and then administered or implanted in a subject. The tissue can be autologous, allogeneic, or xenogeneic tissue. E.g., tissue can be treated to reduce graft v. host disease. In other embodiments, the tissue is allogeneic and the tissue is treated to treat a disorder characterized by unwanted gene expression in that tissue. E.g., tissue, e.g., hematopoietic cells, e.g., bone marrow hematopoietic cells, can be treated to inhibit unwanted cell proliferation. Introduction of treated tissue, whether autologous or transplant, can be combined with other therapies. In some implementations, the single stranded oligonucleotide treated cells are insulated from other cells, e.g., by a semipermeable porous barrier that prevents the cells from leaving the implant, but enables molecules from the body to reach the cells and molecules produced by the cells to enter the body. In one embodiment, the porous barrier is formed from alginate.

In one embodiment, a contraceptive device is coated with or contains a single stranded oligonucleotide. Exemplary devices include condoms, diaphragms, IUD (implantable uterine devices, sponges, vaginal sheaths, and birth control devices.

Dosage

In one aspect, the invention features a method of administering a single stranded oligonucleotide (e.g., as a compound or as a component of a composition) to a subject (e.g., a human subject). In one embodiment, the unit dose is between about 10 mg and 25 mg per kg of bodyweight. In one embodiment, the unit dose is between about 1 mg and 100 mg per kg of bodyweight. In one embodiment, the unit dose is between about 0.1 mg and 500 mg per kg of bodyweight. In some embodiments, the unit dose is more than 0.001, 0.005, 0.01, 0.05, 0.1, 0.5, 1, 2, 5, 10, 25, 50 or 100 mg per kg of bodyweight.

The defined amount can be an amount effective to treat or prevent a disease or condition, e.g., a disease or condition associated with the target gene. The unit dose, for example, can be administered by injection (e.g., intravenous or intramuscular), an inhaled dose, or a topical application.

In some embodiments, the unit dose is administered daily. In some embodiments, less frequently than once a day, e.g., less than every 2, 4, 8 or 30 days. In another embodiment, the unit dose is not administered with a frequency (e.g., not a regular frequency). For example, the unit dose may be administered a single time. In some embodiments, the unit dose is administered more than once a day, e.g., once an hour, two hours, four hours, eight hours, twelve hours, etc.

In one embodiment, a subject is administered an initial dose and one or more maintenance doses of a single stranded oligonucleotide. The maintenance dose or doses are generally lower than the initial dose, e.g., one-half less of the initial dose. A maintenance regimen can include treating the subject with a dose or doses ranging from 0.0001 to 100 mg/kg of body weight per day, e.g., 100, 10, 1, 0.1, 0.01, 0.001, or 0.0001 mg per kg of bodyweight per day. The maintenance doses may be administered no more than once every 1, 5, 10, or 30 days. Further, the treatment regimen may last for a period of time which will vary depending upon the nature of the particular disease, its severity and the overall condition of the patient. In some embodiments the dosage may be delivered no more than once per day, e.g., no more than once per 24, 36, 48, or more hours, e.g., no more than once for every 5 or 8 days. Following treatment, the patient can be monitored for changes in his condition and for alleviation of the symptoms of the disease state. The dosage of the oligonucleotide may either be increased in the event the patient does not respond significantly to current dosage levels, or the dose may be decreased if an alleviation of the symptoms of the disease state is observed, if the disease state has been ablated, or if undesired side-effects are observed.

The effective dose can be administered in a single dose or in two or more doses, as desired or considered appropriate under the specific circumstances. If desired to facilitate repeated or frequent infusions, implantation of a delivery device, e.g., a pump, semi-permanent stent (e.g., intravenous, intraperitoneal, intracisternal or intracapsular), or reservoir may be advisable.

In some embodiments, the oligonucleotide pharmaceutical composition includes a plurality of single stranded oligonucleotide species. In another embodiment, the single stranded oligonucleotide species has sequences that are non-overlapping and non-adjacent to another species with respect to a naturally occurring target sequence (e.g., a target RNA). In another embodiment, the plurality of single stranded oligonucleotide species is specific for different target RNAs. In another embodiment, the single stranded oligonucleotide is allele specific. In some cases, a patient is treated with a single stranded oligonucleotide in conjunction with other therapeutic modalities.

Following successful treatment, it may be desirable to have the patient undergo maintenance therapy to prevent the recurrence of the disease state, wherein the compound of the invention is administered in maintenance doses, ranging from 0.0001 mg to 100 mg per kg of body weight.

The concentration of the single stranded oligonucleotide composition is an amount sufficient to be effective in treating or preventing a disorder or to regulate a physiological condition in humans. The concentration or amount of single stranded oligonucleotide administered will depend on the parameters determined for the agent and the method of administration, e.g. nasal, buccal, pulmonary. For example, nasal formulations may tend to require much lower concentrations of some ingredients in order to avoid irritation or burning of the nasal passages. It is sometimes desirable to dilute an oral formulation up to 10-100 times in order to provide a suitable nasal formulation.

Certain factors may influence the dosage required to effectively treat a subject, including but not limited to the severity of the disease or disorder, previous treatments, the general health and/or age of the subject, and other diseases present. Moreover, treatment of a subject with a therapeutically effective amount of a single stranded oligonucleotide can include a single treatment or, preferably, can include a series of treatments. It will also be appreciated that the effective dosage of a single stranded oligonucleotide used for treatment may increase or decrease over the course of a particular treatment. For example, the subject can be monitored after administering a single stranded oligonucleotide composition. Based on information from the monitoring, an additional amount of the single stranded oligonucleotide composition can be administered.

Dosing is dependent on severity and responsiveness of the disease or condition to be treated, with the course of treatment lasting from several days to several months, or until a cure is effected or a diminution of disease state is achieved. Optimal dosing schedules can be calculated from measurements of target gene expression levels in the body of the patient. Persons of ordinary skill can easily determine optimum dosages, dosing methodologies and repetition rates. Optimum dosages may vary depending on the relative potency of individual compounds, and can generally be estimated based on EC50s found to be effective in in vitro and in vivo animal models. In some embodiments, the animal models include transgenic animals that express a human target gene. In another embodiment, the composition for testing includes a single stranded oligonucleotide that is complementary, at least in an internal region, to a sequence that is conserved between the target gene in the animal model and the target gene in a human.

In one embodiment, the administration of the single stranded oligonucleotide composition is parenteral, e.g. intravenous (e.g., as a bolus or as a diffusible infusion), intradermal, intraperitoneal, intramuscular, intrathecal, intraventricular, intracranial, subcutaneous, transmucosal, buccal, sublingual, endoscopic, rectal, oral, vaginal, topical, pulmonary, intranasal, urethral or ocular. Administration can be provided by the subject or by another person, e.g., a health care provider. The composition can be provided in measured doses or in a dispenser which delivers a metered dose. Selected modes of delivery are discussed in more detail below.

Kits

In certain aspects of the invention, kits are provided, comprising a container housing a composition comprising a single stranded oligonucleotide. In some embodiments, the composition is a pharmaceutical composition comprising a single stranded oligonucleotide and a pharmaceutically acceptable carrier. In some embodiments, the individual components of the pharmaceutical composition may be provided in one container. Alternatively, it may be desirable to provide the components of the pharmaceutical composition separately in two or more containers, e.g., one container for single stranded oligonucleotides, and at least another for a carrier compound. The kit may be packaged in a number of different configurations such as one or more containers in a single box. The different components can be combined, e.g., according to instructions provided with the kit. The components can be combined according to a method described herein, e.g., to prepare and administer a pharmaceutical composition. The kit can also include a delivery device.

The present invention is further illustrated by the following Examples, which in no way should be construed as further limiting. The entire contents of all of the references (including literature references, issued patents, published patent applications, and co-pending patent applications) cited throughout this application are hereby expressly incorporated by reference.

EXAMPLES

The invention is further described in the following examples, which do not limit the scope of the invention described in the claims.

Example 1: Hybrid Oligos that Target FXN 3'UTR

Oligo Design

Oligonucleotides were designed to target the 3'UTR of the Frataxin gene (FXN). The oligonucleotide sequence and modification ("formatted") patterns are provided in Table 3 below. Table 4 provides a description of the nucleotide analogs, modifications and intranucleotide linkages used for certain oligonucleotides described in Table 3 and Table 5.

TABLE 3

Exemplary hybrid oligos for FXN

| Oligo Name | Gene Organism | Gene Name | Base Sequence | Formatted Sequence |
|---|---|---|---|---|
| FXN-781 m1000 | human | FXN | AATAGGCCAAGGAAGA CAAGTCCAG (SEQ ID NO: 1) | InaAs; InaAs; dTs; dAs; dGs; dGs; dCs; dCs; dAs; dAs; dGs; InaGs; InaAs; omeAs; InaGs; omeAs; InaCs; omeAs; InaAs; omeGs; InaTs; omeCs; InaCs; omeAs; InaG-Sup |
| FXN-782 m1000 | human | FXN | ATAGCTTTTAATGTCCTT AAAACGG (SEQ ID NO: 2) | InaAs; InaTs; dAs; dGs; dCs; dTs; dTs; dTs; dTs; dAs; dAs; InaTs; InaGs; omeTs; InaCs; omeCs; InaTs; omeUs; InaAs; omeAs; InaAs; omeAs; InaCs; omeGs; InaG-Sup |
| FXN-783 m1000 | human | FXN | CACATAGCCCAACTGTC CTCAAAAG (SEQ ID NO: 3) | InaCs; InaAs; dCs; dAs; dTs; dAs; dGs; dCs; dCs; dCs; dAs; InaAs; InaCs; omeTs; InaGs; omeUs; InaCs; omeCs; InaTs; omeCs; InaAs; omeAs; InaAs; omeAs; InaG-Sup |
| FXN-784 m1000 | human | FXN | GCATAAGACATTATAAA AGATAAGG (SEQ ID NO: 4) | InaGs; InaCs; dAs; dTs; dAs; dAs; dGs; dAs; dCs; dAs; dTs; InaTs; InaAs; InaTs; InaAs; omeAs; InaAs; omeAs; InaGs; omeAs; InaTs; omeAs; InaAs; omeGs; InaG-Sup |

TABLE 4

A listing of oligonucleotide modifications.

| Symbol | Feature Description |
|---|---|
| bio | 5' biotin |
| dAs | DNA w/3' thiophosphate |
| dCs | DNA w/3' thiophosphate |
| dGs | DNA w/3' thiophosphate |
| dTs | DNA w/3' thiophosphate |
| dG | DNA |
| enaAs | ENA w/3' thiophosphate |
| enaCs | ENA w/3' thiophosphate |
| enaGs | ENA w/3' thiophosphate |
| enaTs | ENA w/3' thiophosphate |
| fluAs | 2'-fluoro w/3' thiophosphate |
| fluCs | 2'-fluoro w/3' thiophosphate |
| fluGs | 2'-fluoro w/3' thiophosphate |
| fluUs | 2'-fluoro w/3' thiophosphate |
| lnaAs | LNA w/3' thiophosphate |
| lnaCs | LNA w/3' thiophosphate |
| lnaGs | LNA w/3' thiophosphate |
| lnaTs | LNA w/3' thiophosphate |
| omeAs | 2'-OMe w/3' thiophosphate |
| omeCs | 2'-OMe w/3' thiophosphate |
| omeGs | 2'-OMe w/3' thiophosphate |
| omeTs | 2'-OMe w/3' thiophosphate |
| lnaAs-Sup | LNA w/3' thiophosphate at 3' terminus |
| lnaCs-Sup | LNA w/3' thiophosphate at 3' terminus |
| lnaGs-Sup | LNA w/3' thiophosphate at 3' terminus |
| lnaTs-Sup | LNA w/3' thiophosphate at 3' terminus |
| lnaA-Sup | LNA w/3' OH at 3' terminus |
| lnaC-Sup | LNA w/3' OH at 3' terminus |
| lnaG-Sup | LNA w/3' OH at 3' terminus |
| lnaT-Sup | LNA w/3' OH at 3' terminus |
| omeA-Sup | 2'-OMe w/3' OH at 3' terminus |
| omeC-Sup | 2'-OMe w/3' OH at 3' terminus |
| omeG-Sup | 2'-OMe w/3' OH at 3' terminus |
| omeU-Sup | 2'-OMe w/3' OH at 3' terminus |
| dAs-Sup | DNA w/3' thiophosphate at 3' terminus |
| dCs-Sup | DNA w/3' thiophosphate at 3' terminus |
| dGs-Sup | DNA w/3' thiophosphate at 3' terminus |
| dTs-Sup | DNA w/3' thiophosphate at 3' terminus |
| dA-Sup | DNA w/3' OH at 3' terminus |
| dC-Sup | DNA w/3' OH at 3' terminus |
| dG-Sup | DNA w/3' OH at 3' terminus |
| dT-Sup | DNA w/3' OH at 3' terminus |
| bio | 5' biotin |
| dAs | DNA w/3' thiophosphate |
| dCs | DNA w/3' thiophosphate |
| dGs | DNA w/3' thiophosphate |
| dTs | DNA w/3' thiophosphate |
| dG | DNA |
| enaAs | ENA w/3' thiophosphate |

The suffix "Sup" in Table 4 indicates that a 3' end nucleotide may, for synthesis purposes, be conjugated to a solid support. It should be appreciated that in general when conjugated to a solid support for synthesis, the synthesized oligonucleotide is released such that the solid support is not part of the final oligonucleotide product.

Figure 2:
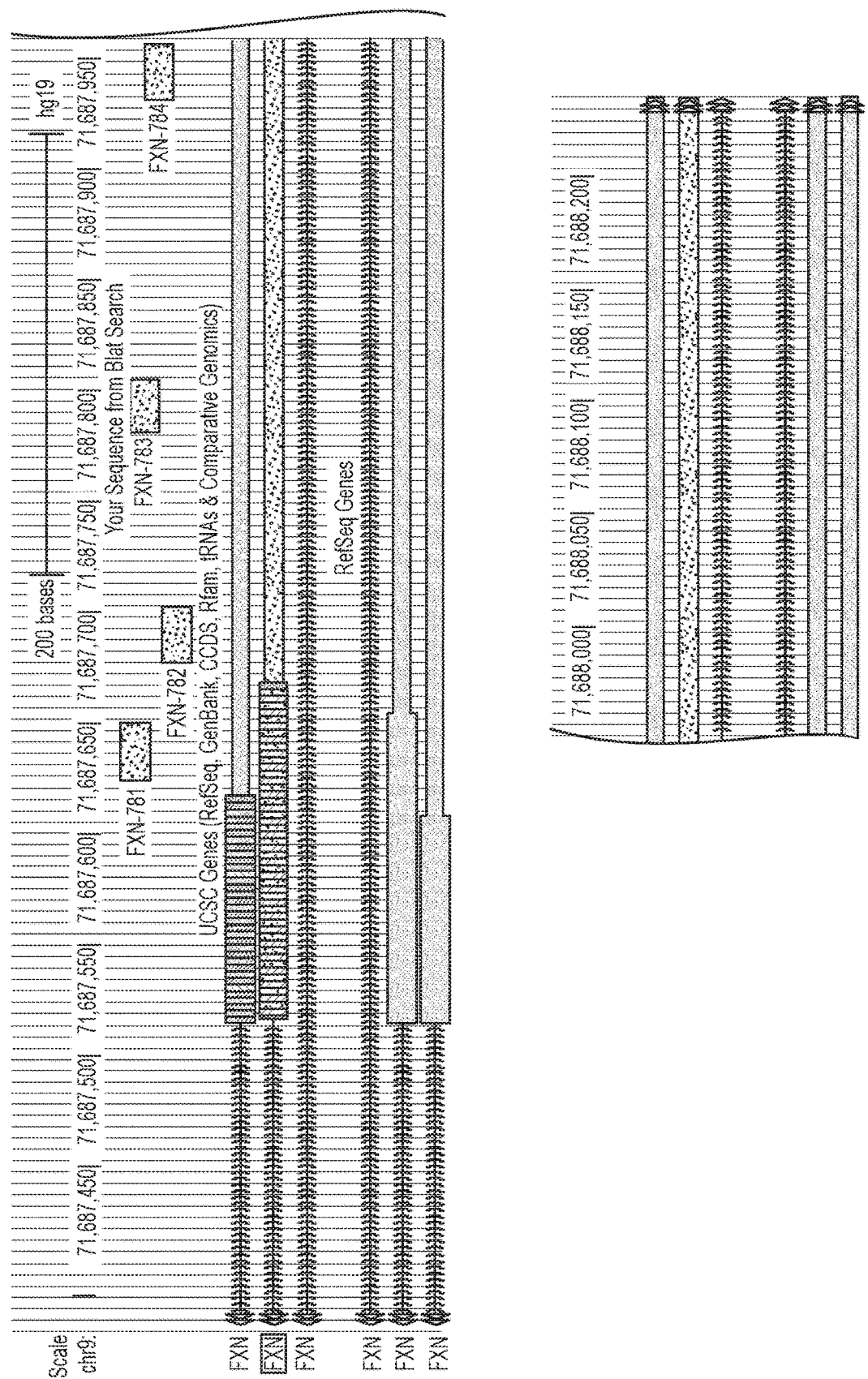
FIG. 2 is a diagram showing the complementarity location of four hybrid oligos designed to target the 3'UTR of FXN.

The 3'UTR of FXN is more than 5 kilobases in length and contains numerous potential and confirmed regulatory sequences, as determined by mapping miRNA database information and other miRNA target sites (see, e.g., microrna.org and Bandiera et al. (2013) Genetic Variations Creating MicroRNA Target Sites in the FXN 3'-UTR Affect Frataxin Expression in Friedreich Ataxia. PLoS ONE 8(1): e54791) onto the 3'UTR (FIGS. 1A-D). Hybrid oligos were designed to selectively cleave off the majority of the 3' UTR, while protecting the remaining cleaved RNA from degradation toward the FXN mRNA coding regions (FIG. 2). The oligos designed were 25mers with 9 DNA bases, 10 LNA and 6 2'Ome bases. The gapmer portion was near the 5' end of the oligo. It was hypothesized that removal of the majority of the 3'UTR would result in upregulation of FXN expression as a result of the removal of the regulatory sequences present in the 3'UTR.

Figure 3:
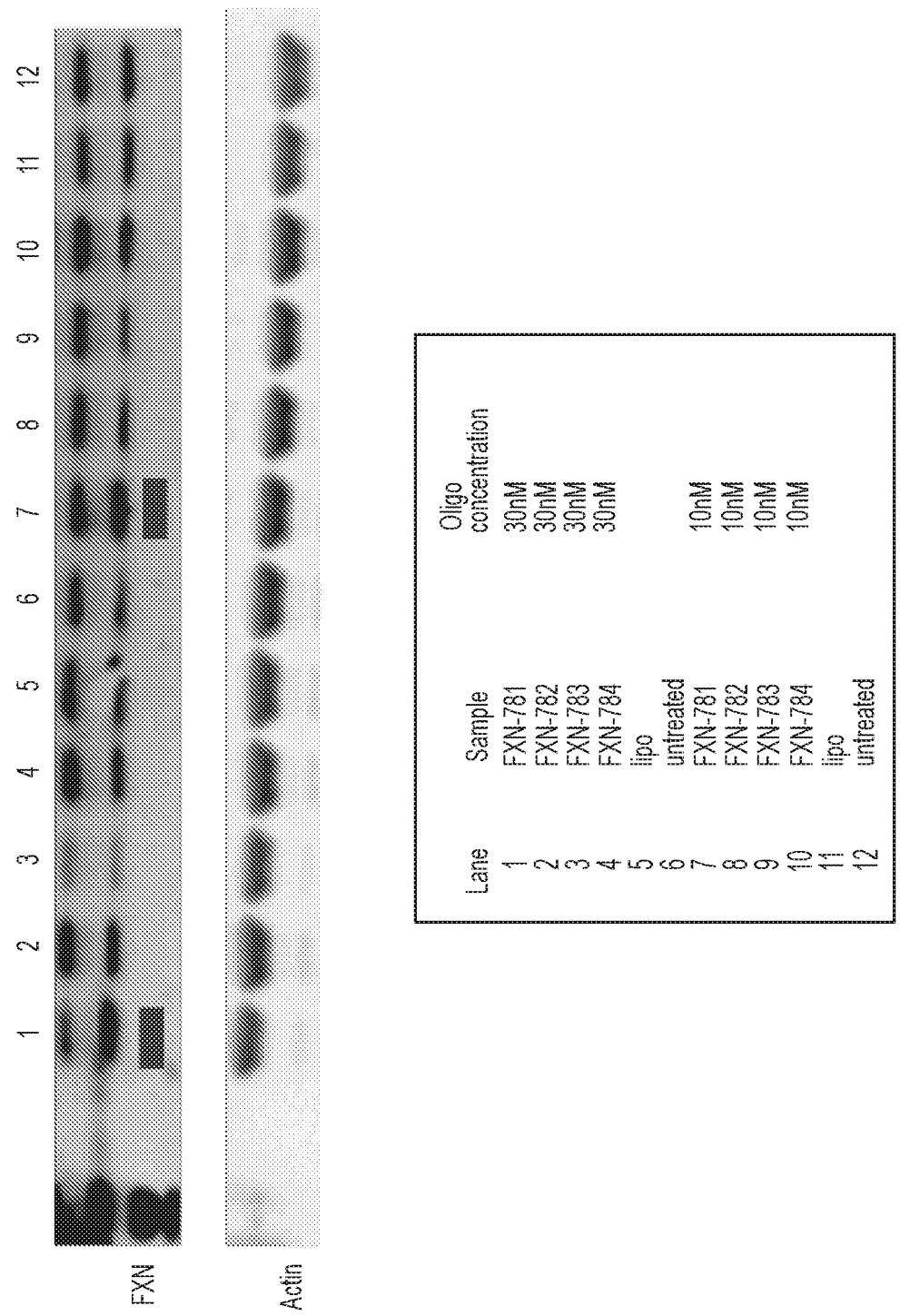
FIG. 3 is a photograph of a Western blot showing the protein levels of FXN in cells treated with FXN oligos or controls in 30 nM or 10 nM oligo concentrations. Boxes indicate lanes where substantial upregulation is observed in this experiment (lanes 1 and 7).

GM03816 cells were transfected with the hybrid oligos at both 30 nM and 10 nM doses. Measurements of FXN protein levels were taken at day 3. FXN-781 showed mature FXN protein upregulation relative to controls (FIG. 3).

Figure 4:
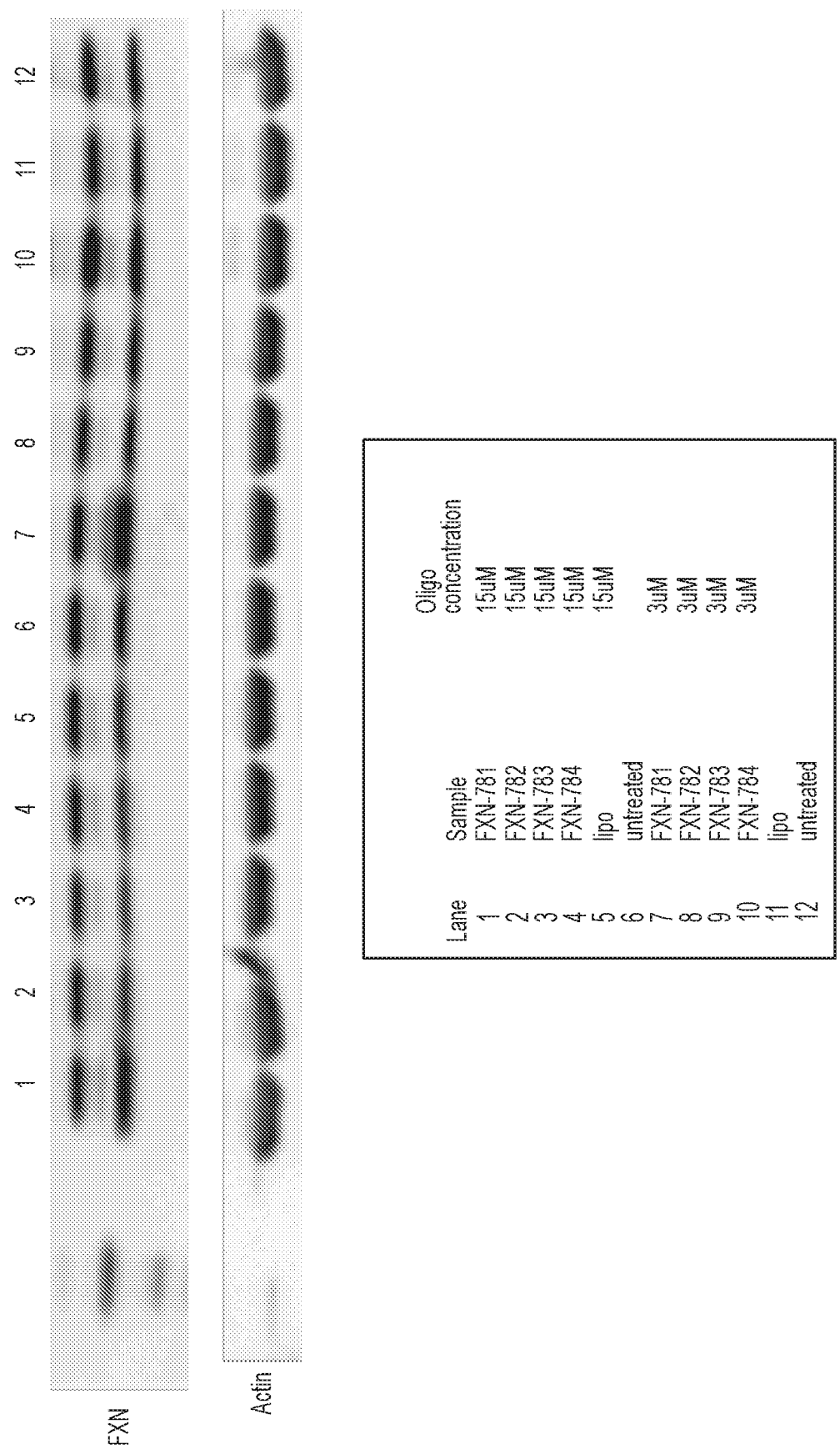
FIG. 4 is a photograph of a Western blot showing the protein levels of FXN in cells treated with FXN oligos or controls in 15 µM or 3 µM concentrations.

Hybrid oligos were delivered to GM15850 lymphoblast cells via gymnotic delivery at both 15 uM and 3 uM doses. Oligo treatment was done at day 1 and day 3. Measurements of FXN protein levels were taken at day 5. FXN-781 show mature FXN protein upregulation relative to controls (FIG. 4).

Figure 5:
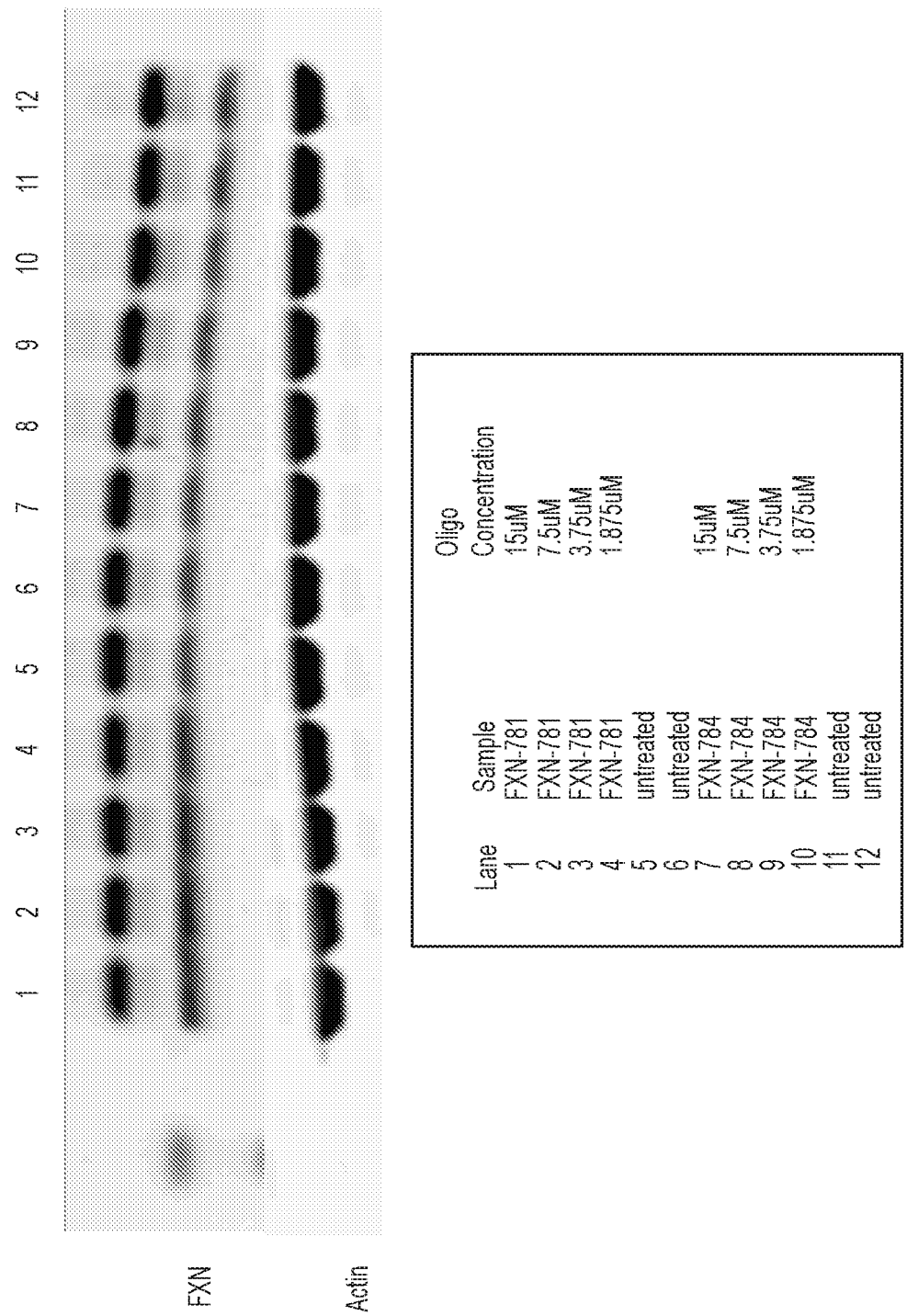
FIG. 5 is a photograph of a Western blot showing the protein levels of FXN in cells treated with FXN oligos or controls in concentrations ranging from 1.875 µM-15 µM.

Next, a dose-response curve was determined by delivering several concentrations of oligos to GM15850 cells via gymnotic delivery. Oligo treatment was done at day 1 and day 3. Measurements of FXN protein levels were taken at day 5. FXN-781 showed potent and dose-responsive mature FXN protein upregulation relative to controls (FIG. 5).

Figure 6:
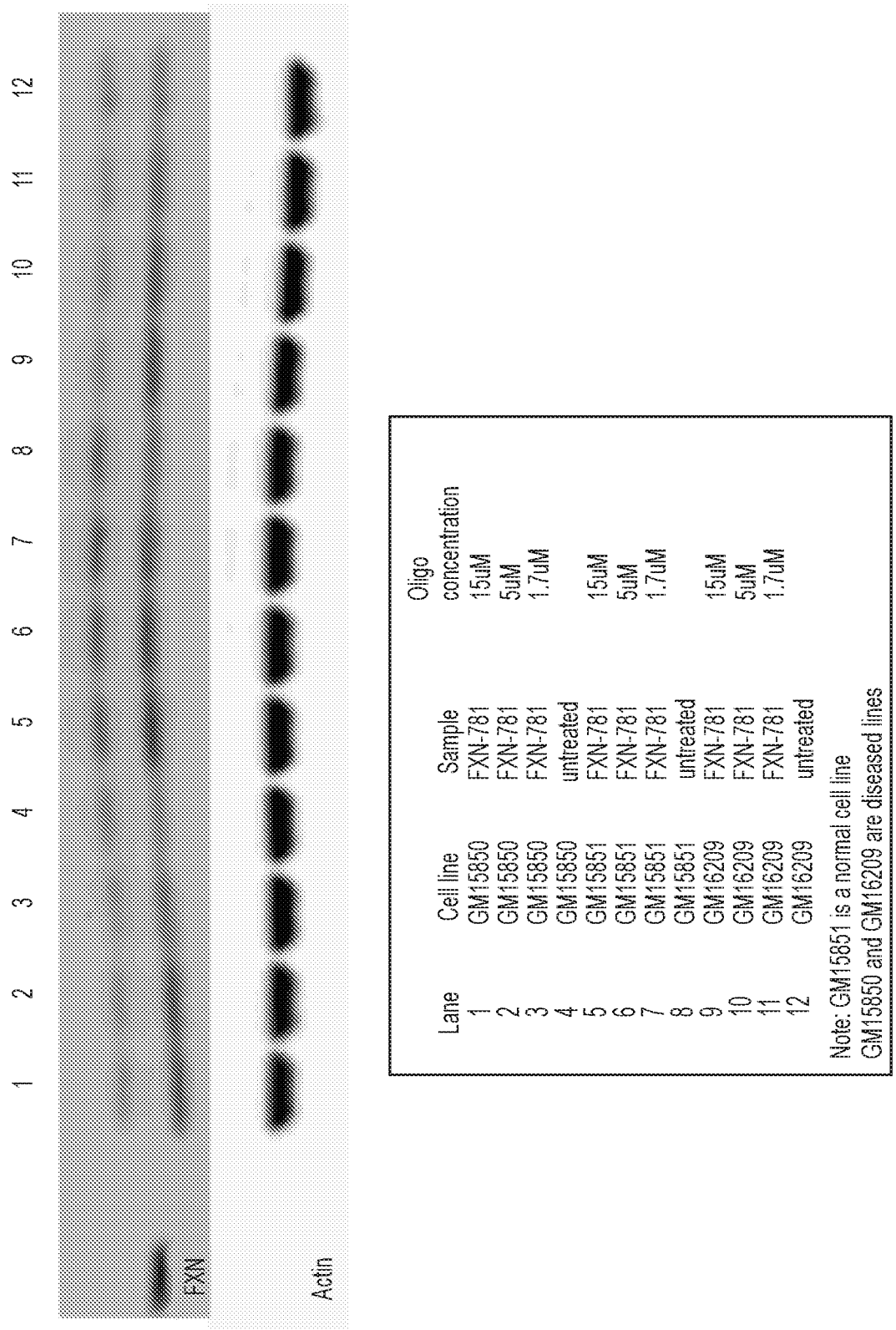
FIG. 6 is a photograph of a Western blot showing the protein levels of FXN in cells treated with FXN oligos or controls in concentrations ranging from 1.7 µM-15 µM.

Subsequently, gymnotic dose response of the FXN-781 oligo was tested in GM15850 and GM16209 diseased, and GM15851 normal lymphoblasts. FXN-781 showed potent and dose-responsive mature FXN protein upregulation relative to controls in two diseased (GM15850 & GM16209) and one normal (GM15851) lymphoblast cells via gymnotic delivery (FIG. 6). Oligo treatment was done at day 1 and day 3. Measurement was taken at day 5.

Figure 7:
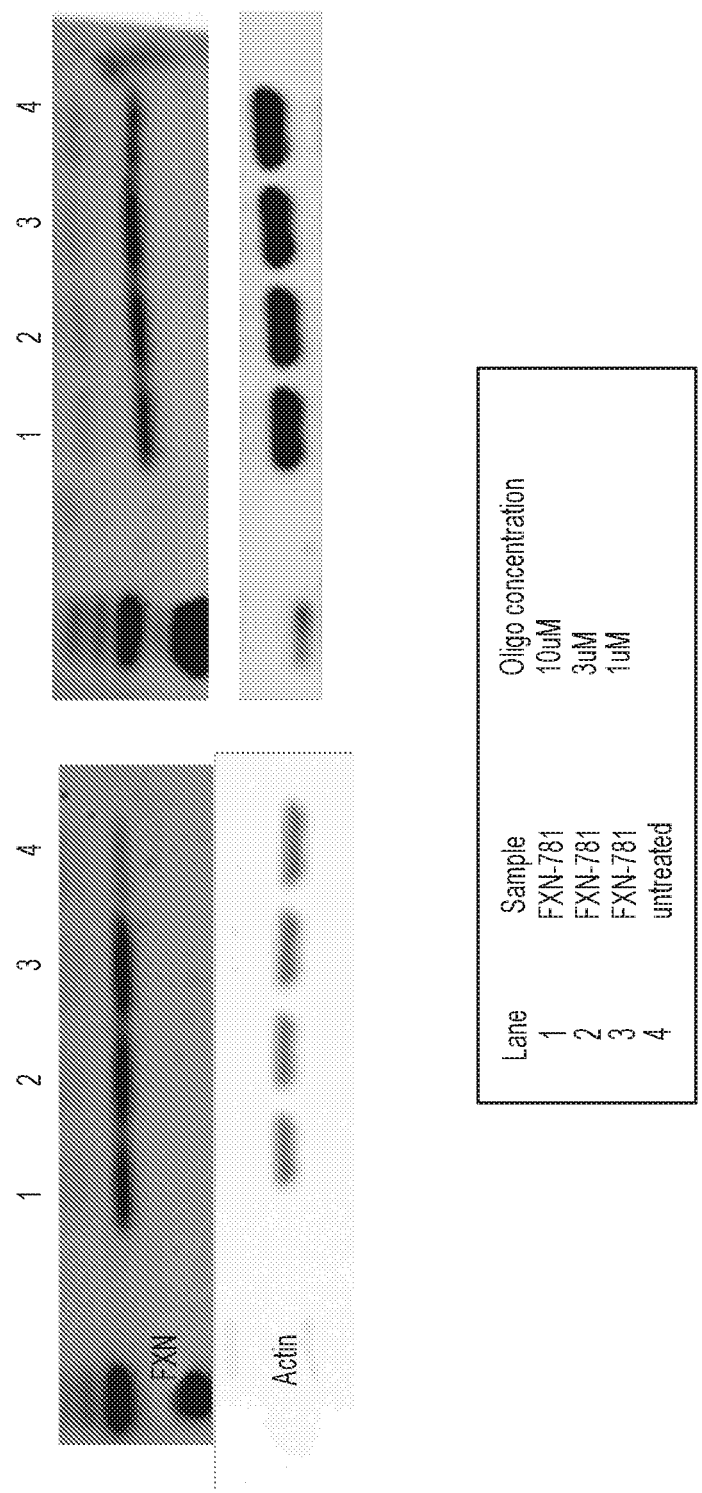
FIG. 7 is a photograph of a Western blot showing the protein levels of FXN in cells treated with FXN oligos or controls in 1 µM, 3 µM, or 10 µM concentrations.

Next, gymnotic treatment of Sarsero fibroblasts with FXN-781 oligo was tested. FXN-781 showed potent mature FXN protein upregulation relative to untreated control in Sarsero skin fibroblasts via gymnotic delivery in two replicates (FIG. 7). Upregulation appeared stronger at 3 uM and 1 uM concentration. Oligo treatment was done at day 1 and day 3. Measurements were taken at day 7.

Figure 8A:
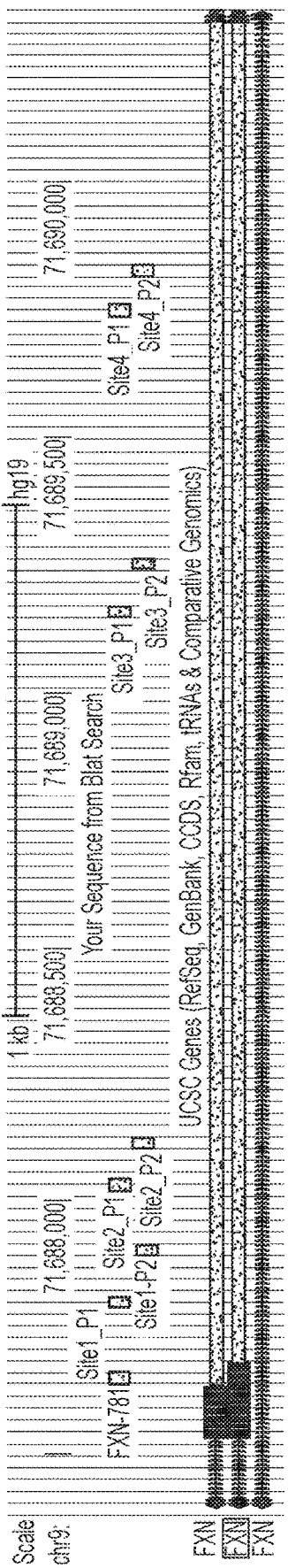
FIG. 8A is a diagram showing the binding sites of primers used to amplify Exons 1-2 and portions of the 3'UTR of FXN.
Figure 8B:
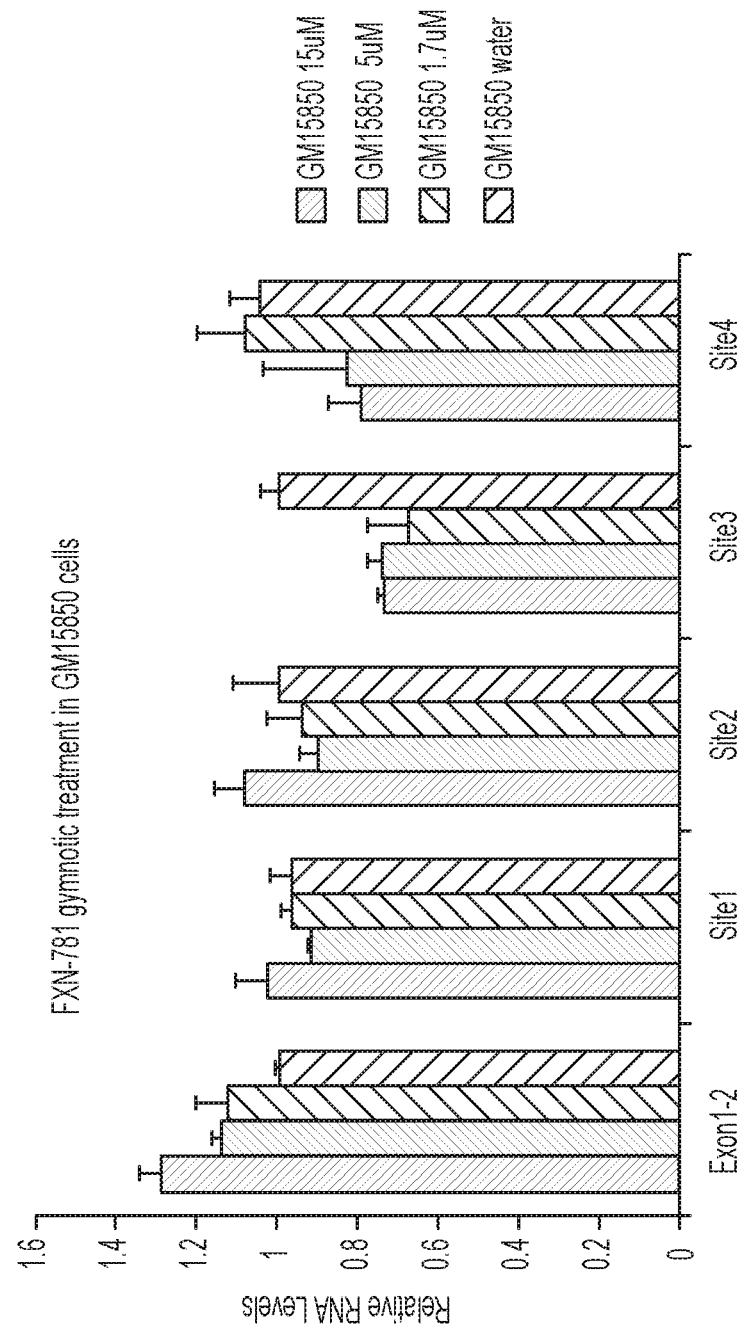
FIG. 8B is a graph showing the levels of FXN exons 1-2 and sites 1-4 in the 3'UTR in cells treated with FXN oligos or a control.

Lastly, RNA analyses were performed in the GM15850 cell line after gymnotic delivery of FXN-781 or water. FXN-781 caused a slight increase in FXN mRNA levels when measured with Exon 1-2 Taqman primers (FIGS. 8A and B). When RNA levels measured with Taqman primers targeting different 3' UTR regions on the 5th exon, up to 30% downregulation was observed (FIGS. 8A and B). This suggests that there may be RNA degradation that is shortening the 3' UTR in a fraction of FXN mRNA molecules, meaning that the hybrid oligos were performing as intended. This decrease may result in the significant FXN mature protein upregulation described above.

Example 2: Hybrid Oligos that Target APOA1

Below are hybrid oligos designed to target APOA1.

TABLE 5

Exemplary hybrid oligos for APOA1

| Oligo Name | Organism | Gene Name | SEQ ID NO: | Base Sequence | Formatted Sequence |
|---|---|---|---|---|---|
| Apoa1_mus-105 m1000 | Mouse | APOA1 | 5 | AGGTTTATTGTAAGAAAGCCAATGC | InaAs; InaGs; dGs; dTs; dTs; dTs; dAs; dTs; dTs; dGs; dTs; InaAs; InaAs; omeGs; InaAs; omeAs; InaAs; omeGs; InaCs; omeCs; InaAs; omeAs; InaTs; omeGs; InaC-Sup |
| Apoa1_mus-106 m1000 | Mouse | APOA1 | 6 | GGTTTATTGTAAGAAAGCCAATGC | InaGs; InaGs; dTs; dTs; dTs; dAs; dTs; dTs; dGs; dTs; InaAs; InaAs; omeGs; InaAs; omeAs; InaAs; omeGs; InaCs; omeCs; InaAs; omeAs; InaTs; omeGs; InaC-Sup |
| Apoa1_mus-107 m1000 | Mouse | APOA1 | 7 | GTTTATTGTAAGAAAGCCAATGC | InaGs; InaTs; dTs; dTs; dAs; dTs; dTs; dGs; dTs; InaAs; InaAs; omeGs; InaAs; omeAs; InaAs; omeGs; InaCs; omeCs; InaAs; omeAs; InaTs; omeGs; InaC-Sup |
| Apoa1_mus-108 m1000 | Mouse | APOA1 | 8 | TTTATTGTAAGAAAGCCAATGC | InaTs; InaTs; dTs; dAs; dTs; dTs; dGs; dTs; InaAs; InaAs; omeGs; InaAs; omeAs; InaAs; omeGs; InaCs; omeCs; InaAs; omeAs; InaTs; omeGs; InaC-Sup |
| Apoa1_mus-109 m1000 | Mouse | APOA1 | 9 | GGTTTATTGTAAGAAAGCCAATG | InaGs; InaGs; dTs; dTs; dTs; dAs; dTs; dTs; dGs; dTs; InaAs; InaAs; omeGs; InaAs; omeAs; InaAs; omeGs; InaCs; omeCs; InaAs; omeAs; omeUs; InaG-Sup |
| Apoa1_mus-110 m1000 | Mouse | APOA1 | 10 | GGTTTATTGTAAGAAAGCCAAT | InaGs; InaGs; dTs; dTs; dTs; dAs; dTs; dTs; dGs; dTs; InaAs; InaAs; omeGs; InaAs; omeAs; InaAs; omeGs; InaCs; omeCs; InaAs; omeAs; InaT-Sup |
| Apoa1_mus-111 m1000 | Mouse | APOA1 | 11 | GGTTTATTGTAAGAAAGCCAA | InaGs; InaGs; dTs; dTs; dTs; dAs; dTs; dTs; dGs; dTs; InaAs; InaAs; omeGs; InaAs; omeAs; InaAs; omeGs; InaCs; omeCs; omeAs; InaA-Sup |
| Apoa1_mus-112 m1000 | Mouse | APOA1 | 12 | TTTATTGTAAGAAAGCCAATG | InaTs; InaTs; dTs; dAs; dTs; dTs; dGs; dTs; InaAs; InaAs; omeGs; InaAs; omeAs; InaAs; omeGs; InaCs; omeCs; InaAs; omeAs; omeUs; InaG-Sup |

TABLE 5-continued

Exemplary hybrid oligos for APOA1

| Oligo Name | Organism | Gene Name | SEQ ID NO: | Base Sequence | Formatted Sequence |
|---|---|---|---|---|---|
| Apoa1_mus-<br>113_m1000 | Mouse | APOA113 | TTTATTGTAAGAA<br>AGCCAAT | InaTs; InaTs; dTs; dAs; dTs; dTs; dGs; dTs; InaAs; InaAs; omeGs; InaAs; omeAs; InaAs; omeGs; InaCs; omeCs; InaAs; omeAs; InaT-Sup |
| Apoa1_mus-<br>114_m1000 | Mouse | APOA114 | TTTATTGTAAGAA<br>AGCCAA | InaTs; InaTs; dTs; dAs; dTs; dTs; dGs; dTs; InaAs; InaAs; omeGs; InaAs; omeAs; InaAs; omeGs; InaCs; omeCs; omeAs; InaA-Sup |
| Apoa1_mus-<br>115_m1000 | Mouse | APOA115 | TGGAAAGGTTTAT<br>TGTAAGAAAGCC | InaTs; InaGs; dGs; dAs; dAs; dAs; dGs; dGs; dTs; dTs; dTs; InaAs; InaTs; omeUs; InaGs; omeUs; InaAs; omeAs; InaGs; omeAs; InaAs; omeAs; InaGs; omeCs; InaC-Sup |
| Apoa1_mus-<br>116_m1000 | Mouse | APOA116 | GGAAAGGTTTATT<br>GTAAGAAAGCC | InaGs; InaGs; dAs; dAs; dAs; dGs; dGs; dTs; dTs; dTs; InaAs; InaTs; omeUs; InaGs; omeUs; InaAs; omeAs; InaGs; omeAs; InaAs; omeAs; InaGs; omeCs; InaC-Sup |
| Apoa1_mus-<br>117_m1000 | Mouse | APOA117 | GAAAGGTTTATTG<br>TAAGAAAGCC | InaGs; InaAs; dAs; dAs; dGs; dGs; dTs; dTs; dTs; InaAs; InaTs; omeUs; InaGs; omeUs; InaAs; omeAs; InaGs; omeAs; InaAs; omeAs; InaGs; omeCs; InaC-Sup |
| Apoa1_mus-<br>118_m1000 | Mouse | APOA118 | AAAGGTTTATTGT<br>AAGAAAGCC | InaAs; InaAs; dAs; dGs; dGs; dTs; dTs; dTs; InaAs; InaTs; omeUs; InaGs; omeUs; InaAs; omeAs; InaGs; omeAs; InaAs; omeAs; InaGs; omeCs; InaC-Sup |
| Apoa1_mus-<br>119_m1000 | Mouse | APOA119 | GGAAAGGTTTATT<br>GTAAGAAAGC | InaGs; InaGs; dAs; dAs; dAs; dGs; dGs; dTs; dTs; dTs; InaAs; InaTs; omeUs; InaGs; omeUs; InaAs; omeAs; InaGs; omeAs; InaAs; omeAs; omeGs; InaC-Sup |
| Apoa1_mus-<br>120_m1000 | Mouse | APOA120 | GGAAAGGTTTATT<br>GTAAGAAAG | InaGs; InaGs; dAs; dAs; dAs; dGs; dGs; dTs; dTs; dTs; InaAs; InaTs; omeUs; InaGs; omeUs; InaAs; omeAs; InaGs; omeAs; InaAs; omeAs; InaG-Sup |
| Apoa1_mus-<br>121_m1000 | Mouse | APOA121 | GGAAAGGTTTATT<br>GTAAGAAA | InaGs; InaGs; dAs; dAs; dAs; dGs; dGs; dTs; dTs; dTs; InaAs; InaTs; omeUs; InaGs; omeUs; InaAs; omeAs; InaGs; omeAs; omeAs; InaA-Sup |
| Apoa1_mus-<br>122_m1000 | Mouse | APOA122 | AAAGGTTTATTGT<br>AAGAAAGC | InaAs; InaAs; dAs; dGs; dGs; dTs; dTs; dTs; InaAs; InaTs; omeUs; InaGs; omeUs; InaAs; omeAs; InaGs; omeAs; InaAs; omeAs; omeGs; InaC-Sup |
| Apoa1_mus-<br>123_m1000 | Mouse | APOA123 | AAAGGTTTATTGT<br>AAGAAAG | InaAs; InaAs; dAs; dGs; dGs; dTs; dTs; dTs; InaAs; InaTs; omeUs; InaGs; omeUs; InaAs; omeAs; InaGs; omeAs; InaAs; omeAs; InaG-Sup |

TABLE 5-continued

Exemplary hybrid oligos for APOA1

| Oligo Name | Organism | Gene Name | SEQ ID NO: | Base Sequence | Formatted Sequence |
|---|---|---|---|---|---|
| Apoa1_mus-124_m1000 | Mouse | APOA1 | 24 | AAAGGTTTATTGTAAGAAA | InaAs; InaAs; dAs; dGs; dGs; dTs; dTs; dTs; InaAs; InaTs; omeUs; InaGs; omeUs; InaAs; omeAs; InaGs; omeAs; omeAs; InaA-Sup |

The foregoing written specification is considered to be sufficient to enable one skilled in the art to practice the invention. The present invention is not to be limited in scope by examples provided, since the examples are intended as a single illustration of one aspect of the invention and other functionally equivalent embodiments are within the scope of the invention. Various modifications of the invention in addition to those shown and described herein will become apparent to those skilled in the art from the foregoing description and fall within the scope of the appended claims. The advantages and objects of the invention are not necessarily encompassed by each embodiment of the invention.

What is claimed is:

1. A composition comprising:
   (i) a first single stranded oligonucleotide having the general formula:

$(X_m^1\text{-}X_n^2\text{-}X_o^3)$, wherein each instance of $X^1$, $X^3$ is independently a modified nucleotide or unmodified ribonucleotide, wherein m and o are independently integers in a range of 1 to 10, reflecting the number of instances of $X^1$ and $X^3$, respectively, linked consecutively together through internucleotide linkages, wherein each instance of $X^2$ is a deoxyribonucleotide, wherein n is an integer in a range of 6 to 20, reflecting the number of instances of $X^2$ linked consecutively together through internucleotide linkages; and
   (ii) a second single stranded oligonucleotide of 4 to 40 nucleotides in length having the general formula:

$(X_p^4\text{-}X_q^5)_r$, wherein each instance of $X^4$ is a modified nucleotide or unmodified ribonucleotide, wherein each instance of $X^5$ is a deoxyribonucleotide, wherein p and q are independently 0 or 1, reflecting the number of instances of $X^4$ and $X^5$, respectively, wherein at least one of $X^4$ and $X^5$ is present and at least one of p and q is 1 in each instance of the unit, $(X_p^4\text{-}X_q^5)$, wherein r is an integer from 2 to 20 reflecting the number of instances of the unit, $(X_p^4\text{-}X_q^5)$, linked together through internucleotide linkages, wherein the second single stranded oligonucleotide does not contain a sequence of more than 5 consecutive deoxyribonucleotides, and wherein the symbol "-" denotes an internucleotide linkage,
   wherein the first single stranded oligonucleotide is linked to the second single stranded oligonucleotide through an internucleotide linkage in the following orientation:

$5'(X_m^1\text{-}X_n^2\text{-}X_o^3)\text{-}(X_p^4\text{-}X_q^5)_r3'$;

wherein the first single stranded oligonucleotide comprises a cleavage promoting region and the second single stranded oligonucleotide comprises a protecting region, wherein the cleavage promoting region is a gapmer and the protecting region is a mixmer, and
   wherein the first single stranded oligonucleotide and the second single stranded oligonucleotide are complementary to a target mRNA and selectively cleave the target mRNA, wherein the first single stranded oligonucleotide and the second single stranded oligonucleotide are complementary to adjacent sites of the target mRNA, wherein the first oligonucleotide comprises a region of complementarity that is complementary with a portion of the 3' UTR of the target mRNA; and wherein the portion of the 3' UTR of the target mRNA is 5' to one or more miRNA binding elements or a repeat region of the target mRNA.

2. The composition of claim 1, wherein at least one of $X^1$, $X^3$ or $X^4$ is a 2'-modified nucleotide.

3. The composition of claim 1, comprising at least one $X^4$ that is a 2'-modified nucleotide.

4. The composition of claim 1, comprising at least one $X^4$ that is a 2'-O-methyl nucleotide, wherein at least one of $X^1$ or $X^3$ is a 2'-O,4'-C— methylene bridged nucleotide.

5. The composition of claim 1, wherein the nucleotides of $X^1$, $X^3$ and/or $X^4$ are ribonucleotides.

6. The composition of claim 1, wherein the first single stranded oligonucleotide and the second single stranded oligonucleotide are complementary to adjacent sites of a FXN mRNA.

7. The composition of claim 1, wherein the n is 6 to 12 deoxyribonucleotides in the first single stranded oligonucleotide.

8. The composition of claim 1, wherein the m and o are independently 1 to 8 modified nucleotides or unmodified ribonucleotides in the first single stranded oligonucleotide.

9. The composition of claim 1, wherein the first single stranded oligonucleotide comprises 8 to 28 deoxyribonucleotides, modified nucleotides, and/or unmodified ribonucleotides.

10. The composition of claim 1, wherein the r is 2 to 10 instances of the unit $(X_p^4\text{-}X_q^5)$.

11. The composition of claim 1, wherein the second single stranded oligonucleotide comprises 4 to 20 deoxyribonucleotides, modified nucleotides, and/or unmodified ribonucleotides.

12. The composition of claim 1, wherein the first single stranded oligonucleotide is complementary with 8 to 40 consecutive nucleotides of the target mRNA.

13. The composition of claim 1, wherein the second single stranded oligonucleotide is complementary with 8 to 40 consecutive nucleotides of the target mRNA.

14. The composition of claim 1, wherein the portion of the 3' UTR of the target mRNA is 5' to the repeat region of the target mRNA, and wherein the repeat region comprises repeating CUG triplets.

15. The composition of claim 1, wherein the first single stranded oligonucleotide and the second single stranded oligonucleotide each comprise at least one modified internucleoside linkage.

16. The composition of claim 15, wherein the at least one modified internucleoside linkage is a phosphorothioate internucleoside linkage.

17. The composition of claim 1, wherein each internucleoside linkage in the first single stranded oligonucleotide and the second single stranded oligonucleotide is a modified internucleoside linkage.

18. The composition of claim 17, wherein the modified internucleoside linkage is a phosphorothioate internucleoside linkage.

19. The composition of claim 1, wherein the GC content of the first single stranded oligonucleotide or the second single stranded oligonucleotide is 30-60%.

20. The composition of claim 1, wherein the portion of the 3' UTR of the target mRNA is 5' to one or more miRNA binding elements of the target mRNA.

* * * * *

```
                        SEQUENCE LISTING

<160> NUMBER OF SEQ ID NOS: 25

<210> SEQ ID NO 1
<211> LENGTH: 25
<212> TYPE: DNA
<213> ORGANISM: Homo sapiens

<400> SEQUENCE: 1
aataggccaa ggaagacaag tccag                                         25

<210> SEQ ID NO 2
<211> LENGTH: 25
<212> TYPE: DNA
<213> ORGANISM: Homo sapiens

<400> SEQUENCE: 2
atagcttttc atgtccttaa aacgg                                         25

<210> SEQ ID NO 3
<211> LENGTH: 25
<212> TYPE: DNA
<213> ORGANISM: Homo sapiens

<400> SEQUENCE: 3
cacatagccc aactgtcctc aaaag                                         25

<210> SEQ ID NO 4
<211> LENGTH: 25
<212> TYPE: DNA
<213> ORGANISM: Homo sapiens

<400> SEQUENCE: 4
gcataagaca ttataaaaga taagg                                         25

<210> SEQ ID NO 5
<211> LENGTH: 25
<212> TYPE: DNA
<213> ORGANISM: Mus musculus

<400> SEQUENCE: 5
aggtttattg taagaaagcc aatgc                                         25

<210> SEQ ID NO 6
```

<211> LENGTH: 24
<212> TYPE: DNA
<213> ORGANISM: Mus musculus

<400> SEQUENCE: 6
ggtttattgt aagaaagcca atgc                                              24

<210> SEQ ID NO 7
<211> LENGTH: 23
<212> TYPE: DNA
<213> ORGANISM: Mus musculus

<400> SEQUENCE: 7
gtttattgta agaaagccaa tgc                                               23

<210> SEQ ID NO 8
<211> LENGTH: 22
<212> TYPE: DNA
<213> ORGANISM: Mus musculus

<400> SEQUENCE: 8
tttattgtaa gaaagccaat gc                                                22

<210> SEQ ID NO 9
<211> LENGTH: 23
<212> TYPE: DNA
<213> ORGANISM: Mus musculus

<400> SEQUENCE: 9
ggtttattgt aagaaagcca atg                                               23

<210> SEQ ID NO 10
<211> LENGTH: 22
<212> TYPE: DNA
<213> ORGANISM: Mus musculus

<400> SEQUENCE: 10
ggtttattgt aagaaagcca at                                                22

<210> SEQ ID NO 11
<211> LENGTH: 21
<212> TYPE: DNA
<213> ORGANISM: Mus musculus

<400> SEQUENCE: 11
ggtttattgt aagaaagcca a                                                 21

<210> SEQ ID NO 12
<211> LENGTH: 21
<212> TYPE: DNA
<213> ORGANISM: Mus musculus

<400> SEQUENCE: 12
tttattgtaa gaaagccaat g                                                 21

<210> SEQ ID NO 13
<211> LENGTH: 20
<212> TYPE: DNA
<213> ORGANISM: Mus musculus

<400> SEQUENCE: 13
tttattgtaa gaaagccaat                                                   20

-continued

```
<210> SEQ ID NO 14
<211> LENGTH: 19
<212> TYPE: DNA
<213> ORGANISM: Mus musculus

<400> SEQUENCE: 14
tttattgtaa gaaagccaa                                                19

<210> SEQ ID NO 15
<211> LENGTH: 25
<212> TYPE: DNA
<213> ORGANISM: Mus musculus

<400> SEQUENCE: 15
tggaaaggtt tattgtaaga aagcc                                         25

<210> SEQ ID NO 16
<211> LENGTH: 24
<212> TYPE: DNA
<213> ORGANISM: Mus musculus

<400> SEQUENCE: 16
ggaaaggttt attgtaagaa agcc                                          24

<210> SEQ ID NO 17
<211> LENGTH: 23
<212> TYPE: DNA
<213> ORGANISM: Mus musculus

<400> SEQUENCE: 17
gaaaggttta ttgtaagaaa gcc                                           23

<210> SEQ ID NO 18
<211> LENGTH: 22
<212> TYPE: DNA
<213> ORGANISM: Mus musculus

<400> SEQUENCE: 18
aaaggtttat tgtaagaaag cc                                            22

<210> SEQ ID NO 19
<211> LENGTH: 23
<212> TYPE: DNA
<213> ORGANISM: Mus musculus

<400> SEQUENCE: 19
ggaaaggttt attgtaagaa agc                                           23

<210> SEQ ID NO 20
<211> LENGTH: 22
<212> TYPE: DNA
<213> ORGANISM: Mus musculus

<400> SEQUENCE: 20
ggaaaggttt attgtaagaa ag                                            22

<210> SEQ ID NO 21
<211> LENGTH: 21
<212> TYPE: DNA
<213> ORGANISM: Mus musculus

<400> SEQUENCE: 21
ggaaaggttt attgtaagaa a                                             21
```

```
<210> SEQ ID NO 22
<211> LENGTH: 21
<212> TYPE: DNA
<213> ORGANISM: Mus musculus

<400> SEQUENCE: 22
aaaggtttat tgtaagaaag c                                              21

<210> SEQ ID NO 23
<211> LENGTH: 20
<212> TYPE: DNA
<213> ORGANISM: Mus musculus

<400> SEQUENCE: 23
aaaggtttat tgtaagaaag                                                20

<210> SEQ ID NO 24
<211> LENGTH: 19
<212> TYPE: DNA
<213> ORGANISM: Mus musculus

<400> SEQUENCE: 24
aaaggtttat tgtaagaaa                                                 19

<210> SEQ ID NO 25
<211> LENGTH: 6200
<212> TYPE: RNA
<213> ORGANISM: Homo sapiens

<400> SEQUENCE: 25
ugcccagccc cguuuuaagg acauuaaaag cuaucaggcc aagaccccag cuucauuaug       60
cagcugaggu cuguuuuug uuguuguugu uguuuauuuu uuuuauuccu gcuuuugagg      120
acaguugggc uaugugucac agcucuguag aaagaaugug uugccuccua ccuugccccc     180
aaguucugau uuuuaauuuc uauggaagau uuuuuggauu gucggauuuc ucccucaca      240 ugauaccccu uaucuuuuau aaugucuuau gccuauaccu gaauauaaca accuuuaaaa     300
aagcaaaaua auaagaagga aaaauuccag gagggaaaau gaauugcucu cacucuucau     360
ucuuugaagg auuuacugca agaaguacau gaagagcagc uggucaaccu gcucacuguu     420
cuaucuccaa augagacaca uuaaagggua gccuacaaau guuucaggc uucuuucaaa      480 guguaagcac uucugagcuc uuuagcauug aagugcgaa agcaacucac acgggaagau      540
cauuucuuau uugugcucug ugacugccaa ggugaggccu gcacugggu guccagggag      600 accuagugcu guuucuccca cauauucaca uacgugucug uguauaua uauuuuuca        660 auuuaaaggu uaguauggaa ucagcugcua caagaaugca aaaaaucuuc caaagacaag     720
aaaagaggaa aaaagccgu uucaugagc ugagugaugu agcguaacaa acaaaaucau       780
ggagcugagg aggugccuug uaaacaugaa ggggcagaua aaggaaggag auacucaugu     840
ugauaaagag agcccugguc cuagacauag uucagccaca aaguaguugu cccuuugugg     900
acaaguuucc caaauucccu ggaccucugc uucccauu guuaaaugag agaauagagu       960
augguugauu cccagcauuc aguggccug ucaagcaacc uaacaggcua guucuaauuc     1020
ccuauugggu agaugagggg augacaaaga acaguuuua agcuauauag gaaacauugu     1080 uauuggugu gcccuaucgu gauucaguu gaauucaugu gaaauaaua gccauccuug       1140 gccuggcgcg guggcucaca ccuguaaucc cagcacuuuu ggaggccaag gugggugggau   1200 caccugaggu caggaguuca agaccagccu ggccaacaug augaaacccc gucucuacua    1260
```

```
aaaauacaaa aaauuagccg ggcaugaugg caggugccug uaaucccagc uacuugggag    1320
gcugaagcgg aagaaucgcu ugaacccaga gguggagguu gcagugagcc gagaucgugc    1380
cauugcacug uaaccugggu gacugagcaa aacucugucu caaaauaaua auaacaauau    1440
aauaauaaua auagccaucc uuuauuguac ccuuacuggg uuaaucguau uauaccacau    1500
uaccucauuu uaauuuuuac ugaccugcac uuuauacaaa gcaacaagcc uccaggacau    1560
uaaaauucau gcaaaguuau gcucauguua uauuauuuuc uuacuaaag aaggauuuau     1620 uaguggcugg gcauggugc gugcaccugu aaucccaggu acucaggagg cugagacggg     1680
agaauugcuu gacccaggc ggaggagguu acagugaguc gagaucguac cugagcgaca     1740
gagcgagacu ccgucucaaa aaaaaaaaa aggaggguuu auuaaugaga aguuuguauu     1800
aauauguagc aaaggcuuuu ccaaugggug aauaaaaaca cauuccauua agucaagcug    1860
ggagcagugg cauauaccua ucccagc ugcacaggag gcugagacag gaggauugcu       1920
ugaagccagg aauggagau cagccuggc aacacagcaa gaaccuaucu cuuaaaaaaa      1980 gaaaaaaaa ccuauuaaua auaaaacagu auaaacaaaa gcuaaauagg uaaaauauuu     2040
uuucugaaau aaaauuauuu uuugagucug auggaaaugu uuaagugcag uaggccagug    2100
ccagugagaa aauaaauaac aucauacaug uuuguaugug uuugcaucuu gcuucuacug    2160
aaaguuucag ugcaccccac uuacuuagaa cucggugaca ugauguacuc cuuuaucugg    2220
gacacagcac aaaagaggua gcagugggg cugcucugac augaaagugg aaguuaagga    2280
aucugggcuc uuauggggu cuugugggcc agcccuucag gccuauuuua cuuucauuuu    2340
acauauagcu cuaauugguu ugauuaucuc guucccaagg caguggaga uccccauuua    2400 aggaaagaaa aggggccugg cacagguggu caugccugua aucccagcac uuugggaggc   2460
ugaggcaagu guaucaccug aggucaggag uucaagacca gccuggccaa cauggcaaaa    2520
ucccgucucu acuaaaaaua uuaaaaaauu ggcugggcgu ggugguucgu gccuauaauu    2580
ucagcuacuc aggaggcuga ggcaggagaa ucgcuuaac cugggggg gaggucugcag     2640 ugagacgaga ucaugccacu ucacuccagc cuggccaaca gagccauacu ccgucucaaa    2700
uaaauaaaua aauaaauaaa gggacuucaa acacaugaac agcagccagg ggaagaauca    2760
aaaucauauu cugucaagca aacuggaaaa guaccacugu guguaccaau agccucccca    2820
ccacagaccc ugggagcauc gccucauuua ugguguggcc cagucaucca ugugaaggau    2880
gaguuuccag gaaagguua uuaaauauuc acugaacau acuggaggag gugaggaauu     2940
gcauaauaca aucuuagaaa acuuuuuuuu ccccuuucua uuuuugaga caggaucuca    3000 cuuggcacu caggcuggag gacaguggua caaucaaagc ucauggcagc cucgaccucc    3060
cuggccuugg gcaauccucc cacaggugug caccuccaua gcuggcuaau ugguguauuu   3120
uuuguagaga ugggguuuca ccauguugcc caggcugguc ucuaacacuu aggcucaagu   3180
gauccaccug ccucguccuc ccaagaugcu gggauuacag gugugugcca caggguuuca   3240
ucagaaagcu uuucuauua uuuuaccuu cuugaguggg uagaaccuca gccacauaga    3300
aaauaaaaug uucuggcaug acuuauuuag cucucuggaa uuacaaagaa ggaaugaggu    3360
guguaaaaga gaaccugggu uuugaauca caaauuuaga auuuaaucga aacucugccu    3420
cuuacuuguu uguagacacu gacagugggcc ucauguuuuu uuuuuuuuua aucuauaaaa   3480
uggagauauc uaacauguug agccugggcc cacaggcaaa gcacaauccu gaugugaaa     3540 guacucaguu caugacaacu guuguucuca caugcauagc auaauuucau auucacauug    3600
```

```
gaggacuucu cccaaaauau ggaugacguu cccuacucaa ccugaacuu aaucaaaaua    3660
cucaguuuac uuaacuucgu auuagauucu gauucccugg aaccauuuau cgugugccuu    3720
accaugcuua uauuuacuu gaucuuuugc auaccuucua aaacuauuuu agccaauuua    3780
aaauuugaca guuugcauua aauuauaggu uuacaauaug cuuuauccag cuauaccugc    3840
cccaaauucu gacagaugcu uuugccaccu cuaaaggaag acccauguuc auagugaugg    3900
aguuugugug gacuaaccau gcaagguugc caaggaaaaa ucgcuuuacg cuuccaaggu    3960
acacacuaag augaaaguaa uuuuaguccg uguccaguug gauucuuggc acauaguuau    4020
cuucugcuag aacaaacuaa aacagcuaca ugccagcaag ggagaaaggg aaggagggg     4080
caaaguuuug aaauuucaug uaaauuuaug cguucaaaaa cgacgaguuc augacuuugu    4140
guauagagua agaaaugccu uuucuuuuuu gagacagagu cuugcucugu cacccaggcu    4200
ggagugcagu ggcacgaucu gggcucacua caaccuccgc cuccggguu caagcaauuc      4260
ucugccucag ccucccgagu agcugggauu acaggugccu gccaccacac ccggcuaauu    4320
uuuguauuuu uaguagagac gggguuucac caucauggcc aggcugguc ugaacuccug      4380
accuaguaau ccaccugccu ccgccuccca aagugcuggg auuacaggcg ugagccacug    4440
cacccagcca gaaaugccuu cuaaucuuug guuuaucuua auuagccagg acacuuggag    4500
ugcaucccga aguaccugau caguggcccc uuuggaaugu guaaaacuca gcucacuuau    4560
aucccugcau ccgcuacaga gacagaaucc aagcucauau guuccaucuu cucuggcugu    4620
auaguuaag gaauggaagg caccagaaca gauuuauuga aauguuuauu agcugaagau      4680
uuauuuagac aguugaggaa aacaucagca cccagcagua aaauuggcuc ucaaagauuu    4740
ucuucuccug uggaaaguca gaccucugag gccccaucca gguagaagua cuagugcaag    4800
aagggccucu gcguccacu ugguuucug ugaucgugg gaacauugu aacgccacau         4860
cuugaccuca aauuguuuag cuccuggcca gacacggugg cucacaccug uaaucccagc    4920
acuuugagag gcugaggcag guggaucacc ugagguuagg aguucgaggc cagccuggc     4980
aacauuguaa aaccccgccu cuacuaaaaa uacaaaaau agcuggccgu aguggcgcac     5040
gccuguuauc ccagcuacuc gggaggcuga ggcaggagaa uugcuugaac cugggguggu   5100
gagguugcag ugagccgaga uuacaccacu gcacuccagc cugggugaca agagggaaac   5160
uccauuaaaa aaauguaauu cccgugucug ccaucuuaag uguaaaggug gcuaaauuau    5220
auagaaaaau aagacaauau cauuucccaa uuacauuccu uccuaccgc acucuaugau      5280
gcuagcugag auuuuuccaa aagaaaaugg cuuaaauaaa acccuaagag aaagaaaaac    5340
uuuaaauccc uccaaagcuc aaaaguaaua gaaacagaug aguuggagu caggauuucu     5400
cguaagauu gccuaggcug uuacugcac aucuccaggu gccacuguug acagagauua       5460
uaacuacaau gugaagugaa uggugccacu gacaguuaug caaaccgucc agagcauagc    5520
caccugaucc ugcugggauu ccucuugcca guccaucagc aguucccuu gaaaguuuca      5580
ccaaacaucc cuuaaaucug cccucuccug cccgucccca guggaggucc ucaucauuuu    5640
ucaccugcau uuuugcagga gcuucuuau auccaccuuc cuccuuuucu cucagcccau      5700
caucuagcua cacagucucc agguaagcu ucagaaagg caaucucuug ucuguaaaac       5760
cuaagcagga ccaaggccaa guucuuagc cugaaaaaug ugcuuuucug acugaacugu      5820
ucaggcacug acucuacaua uaauugcu uucuacccc cucacacuca acacuuugac       5880
uccagcaauc ccaaaucccc agaucccaaa gugugcugug cuauuuucac guggcucuca    5940
gacuuggcca gugcuguuuc cauuuugguc uuuauuccccc acaucucugc cugggggua    6000
```

```
gauucuaccc ugaaaaaugu ucuuggcaca gccuugcaaa cuccuccucc acucagccuc    6060
ugccuggaug cccuugauug uuccaugucc ucagcauacc auguuugucu uucccagcac    6120
ugaccuacca ugugucaccc cugcuuggcu guaccuucca ugaggcuagg acuauguguc    6180
uccuuuguug acugcuguug                                                6200
```